United States Patent
Kristensen et al.

(10) Patent No.: US 11,963,986 B2
(45) Date of Patent: Apr. 23, 2024

(54) PROBIOTIC SUPPLEMENT FOR METABOLIC HEALTH

(71) Applicant: Novozymes A/S, Bagsvaerd (DK)

(72) Inventors: Nanna Ny Kristensen, Bagsvaerd (DK); Alexandra Mattern, Berlin (DE); Delphine Marie Anne Saulnier, Berlin (DE); Jeffrey Schultchen, Berlin (DE); Teis Jensen, Bagsvaerd (DK); Benjamin Anderschou Holbech Jensen, Québec (CA)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/287,719

(22) PCT Filed: Oct. 24, 2019

(86) PCT No.: PCT/EP2019/079027
§ 371 (c)(1),
(2) Date: Apr. 22, 2021

(87) PCT Pub. No.: WO2020/084051
PCT Pub. Date: Apr. 30, 2020

(65) Prior Publication Data
US 2021/0393712 A1  Dec. 23, 2021

(30) Foreign Application Priority Data
Oct. 24, 2018  (EP) .................................... 18202187

(51) Int. Cl.
*A61K 35/747* (2015.01)
*A23L 33/00* (2016.01)
*A23L 33/135* (2016.01)

(52) U.S. Cl.
CPC .......... *A61K 35/747* (2013.01); *A23L 33/135* (2016.08); *A23L 33/30* (2016.08)

(58) Field of Classification Search
None
See application file for complete search history.

(56) References Cited

U.S. PATENT DOCUMENTS

| | | | |
|---|---|---|---|
| 7,846,711 B2 * | 12/2010 | Boettner | A61P 1/04 435/252.9 |
| 7,901,926 B2 | 3/2011 | Yu et al. | |
| 8,298,526 B2 * | 10/2012 | Leu | C12N 1/20 424/93.1 |
| 2007/0148149 A1 | 6/2007 | Boettner et al. | |
| 2009/0208469 A1 | 8/2009 | Alenfall et al. | |
| 2011/0300117 A1 | 12/2011 | Leu et al. | |
| 2012/0020942 A1 | 1/2012 | Bottner et al. | |
| 2014/0079676 A1 | 3/2014 | Olmstead | |
| 2014/0147427 A1 | 5/2014 | Arya et al. | |
| 2015/0196608 A1 | 7/2015 | Chen et al. | |
| 2015/0250835 A1 | 9/2015 | Huang et al. | |
| 2015/0374764 A1 | 12/2015 | Robins et al. | |
| 2016/0279181 A1 | 9/2016 | Hoshiko | |

FOREIGN PATENT DOCUMENTS

| | | |
|---|---|---|
| CN | 101325960 A | 12/2008 |
| CN | 101384700 A | 3/2009 |
| CN | 102935092 A | 2/2013 |
| CN | 104968780 A | 10/2015 |
| CN | 107375344 | 11/2017 |
| EP | 2543379 A1 | 6/2010 |
| GB | 201400407 | 2/2014 |
| KR | 101864347 | 5/2018 |
| WO | 2007125558 A1 | 11/2007 |
| WO | 2017097984 A1 | 6/2017 |

OTHER PUBLICATIONS

Peijun Tian et al. "Antidiabetic (type 2) effects of Lactobacillus G15 and Q14 in rats through regulation of intestinal permeability and microbiota". Food and Function. 2016, 7, pp. 3789-3797.*
Hill et al., 2014, Nature reviews 11, 506-514.
Holz et al., 2015, Probiotics and Antimicro. proteins 7(2), 91-100.
Maragkoudakis et al, 2006, International dairy journal 16(3), 189-199.
Wei et al., 2015, Journal of Functional foods 18, 473-486.
Maragkoudakis et al., International Journal of Food Microbiology, 2010, S91-S97, 141.
Wang et al., Acta Microbiologica Sinica, 2017, 1287-1297, 58(7)—Incl EnAb.

* cited by examiner

*Primary Examiner* — Vera Afremova
(74) *Attorney, Agent, or Firm* — Eric J. Fechter

(57) ABSTRACT

The application discloses *Lactobacillus* strains having a beneficial effect on the metabolic health on a mammalian subject. Further disclosed is compositions comprising such strains and the use thereof for improving the metabolic health or for lowering the blood glucose level in a mammalian subject.

19 Claims, 35 Drawing Sheets

A. TEER ratio in the absence of pro-inflammatory stimuli

B. TEER ratio in the presence of pro-inflammatory stimuli

|  | Disease Control | Healthy Control |
|---|---|---|
| Disease Control | NA | 10.0 |
| Healthy Control | 10.0 | NA |
| HH04 | 11.5 | 5.2 |
| HH05 | 6.7 | 8.8 |

Study overview

E

F

US 11,963,986 B2

PROBIOTIC SUPPLEMENT FOR METABOLIC HEALTH

Cross-Reference to Related Applications

This application is a 35 U.S.C. 371 national application of PCT/EP2019/079027, filed Oct. 24, 2019, which claims priority or the benefit from European Patent Application 18202187.3, filed Oct. 24, 2018. The contents of these applications are fully incorporated herein by reference.

REFERENCE TO A DEPOSIT OF BIOLOGICAL MATERIAL

This application contains a reference to a deposit of biological material, which deposit is incorporated herein by reference. For complete information see last paragraph of the description.

FIELD OF THE INVENTION

The present invention relates to bacterial strains, cell components, metabolites and secreted molecules thereof having the ability of improving the metabolic health of a mammalian subject. The application also relates to composition comprising such bacterial strains and the use of such compositions to improve the metabolic health of a mammalian subject.

BACKGROUND OF THE INVENTION

In recent years, it has been shown several times that bacteria have an important and significant impact on the health of mammalians, in particular human beings, and it has been realized that a beneficial microbiota in the gastrointestinal tract is important for the proper nutrition and wellbeing.

Intake of microbial cultures or strains, also termed probiotics, has now been recognized as a way to improve the health of individuals using the microbial cultures or strains. In this connection and throughout the description and claims the terms probiotics, microbial cultures and microbial strains are understood in the generally accepted way as "live microorganisms, which when administered in adequate amounts, confer a health benefit to the host" (http://www-.nature.com/articles/nrgastro.2014.66?foxtrotcallback=true).

Microbial strains can be used both for improving an unsatisfactory health status in an individual and for preventing that the unsatisfactory health situation arises.

The beneficial property of probiotics depends on the property of the microbial strain that form the probiotics and it is therefore important to provide new microbial strains having beneficial properties that allows the strains to be used as probiotics.

SUMMARY OF THE INVENTION

In a first aspect, the invention relates to a Lactobacillus strain having the ability of improving the metabolic health, such as alleviating prediabetes, of a mammalian subject. In a further or alternative aspect, the Lactobacillus strain of the invention has the ability to lower the blood glucose level in a mammalian subject. The Lactobacillus strain of the invention may e.g. be a strain deposited at DSMZ-"German Collection of Microorganisms and Cell Cultures" under the deposit numbers: DSM 17648, DSM 32851, DSM 32853, DSM 32910 and/or DSM 32911.

In a second aspect, the invention relates to a composition comprising one or more Lactobacillus strains of the invention, preferably formulated in discrete dosage formulations.

In a third aspect, the invention relates to the use one or more Lactobacillus strains of the invention or a composition comprising one or more Lactobacillus strains of the invention for the improvement of the metabolic health, such as alleviating prediabetes, in mammalian subject, for maintaining of normal blood glucose level and/or reducing postprandial glycemic response in an individual, preventing or alleviating insulin resistance, or for preventing or reducing weight gain in an individual having a high fat and/or high sugar diet.

Finally, in a fourth aspect the invention relates to a method for screening for a Lactobacillus strain having the ability of improving the metabolic health, such as alleviating prediabetes, of a mammalian subject.

Ratio of phosphorylated (activated) Akt protein levels to total Akt protein levels in liver tissue of insulin-stimulated mice quantified by Western blot. A-B) Each bar represents mean value of 10-12 mice per group. C) Each bar represents mean value of 3-4 mice per group. More details about the study can be found in example 11.

Figure 36:
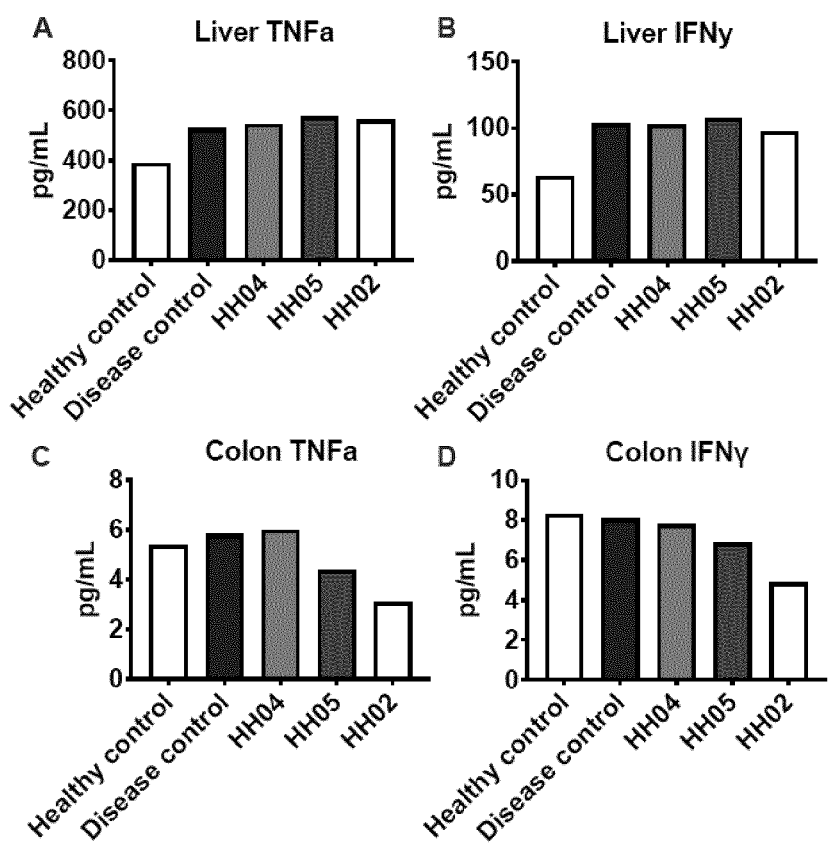

FIG. 36 shows results of *Lactobacillus* strain effect on liver and colon tissue inflammation in a diet-induced obesity mouse model. A) Tumor necrosis factor alpha (TNFα) levels in liver tissue and B) Cytokine Interferon γ (IFNγ) levels in liver tissue. C) Tumor necrosis factor alpha (TNFα) levels in colon tissue. D) Cytokine Interferon γ (IFNγ) levels in colon tissue. A-D) Each bar represents mean value of 10-12 mice per group. More details about the study can be found in example 11.

Figure 37:
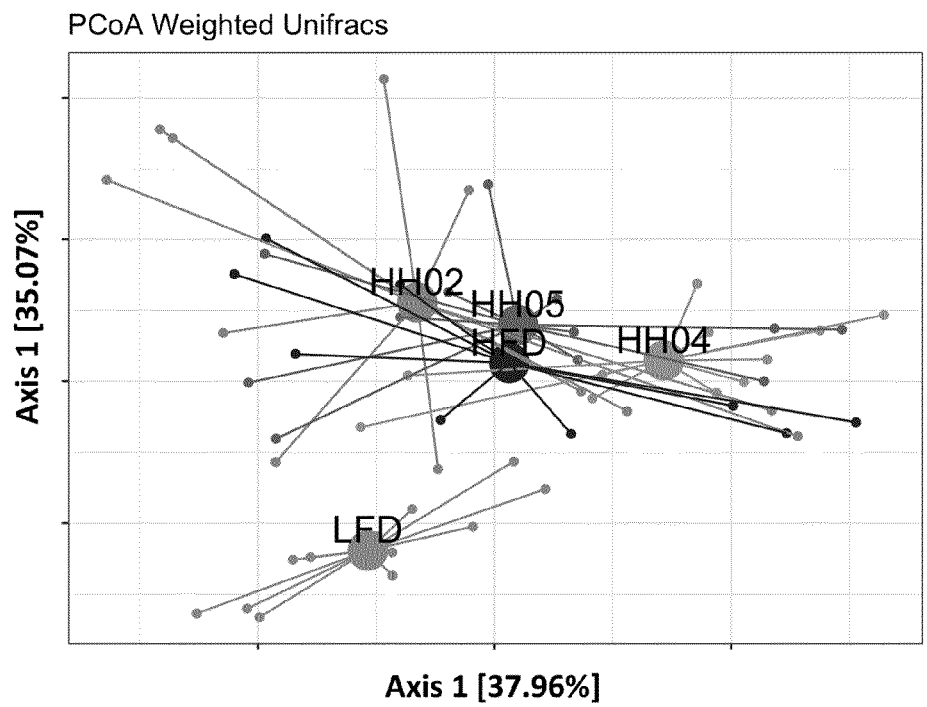

FIG. 37 shows results of *Lactobacillus* strain effect on gut microbiota composition in a diet-induced obesity mouse model. Principal coordinate analysis (PCoA) using weighted unifrac distances clutering the fecal microbiota composition from the end of the study within the indicated groups. Larger points indicate group mean of 10-12 mice per group. More details about the study can be found in example 11.

Figure 38:
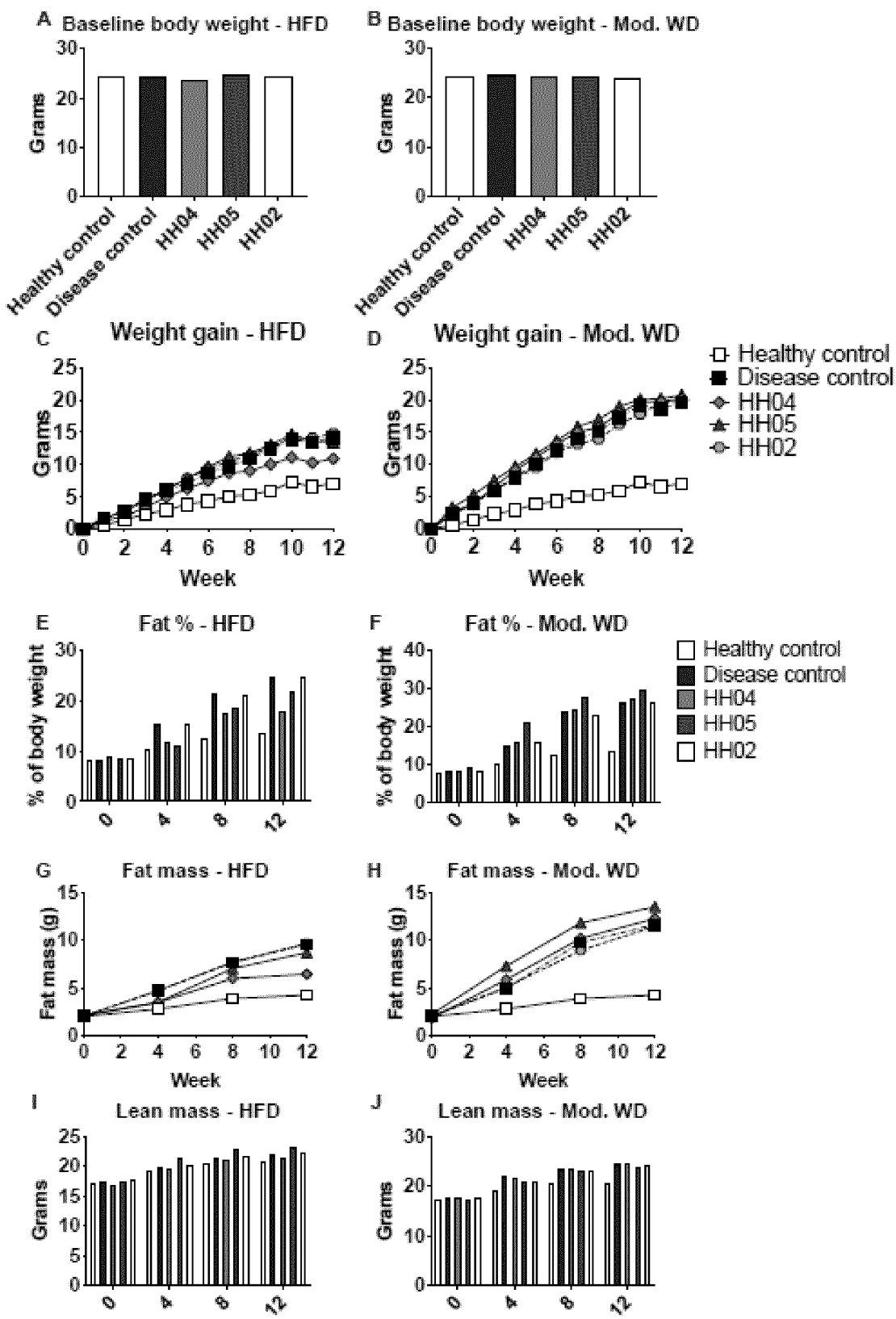

FIG. 38 shows the effect of HH04, HH05, and HH02 on weight development and body composition two diet-induced obesity mouse (DIO) models. Mean of 8-9 mice per group are shown A) Weight after randomization for mice fed either LFD or HFD. B) Weight after randomization for mice fed either LFD or modified WD. C) Weight development in individual groups fed LFD or HFD post initiation of experimental diets and gavage treatment. D) As C, but in groups fed LFD or mod. WD. E) Fat mass as % of total body weight obtained from Magnetic Resonance scans at the depicted time points in groups fed LFD or HFD. F) As E, but groups fed either LFD or mod. WD. G) Fat mass development as grams depicted as group mean with connecting lines for groups fed either LFD or HFD. H) As G, but for groups fed LFD or mod. WD. I) Lean mass as gram obtained from Magnetic Resonance scans at the depicted time points for groups fed LFD or HFD. J) As I, but for groups fed LFD or mod. WD. A-J) More details can be found in example 12.

Figure 39:
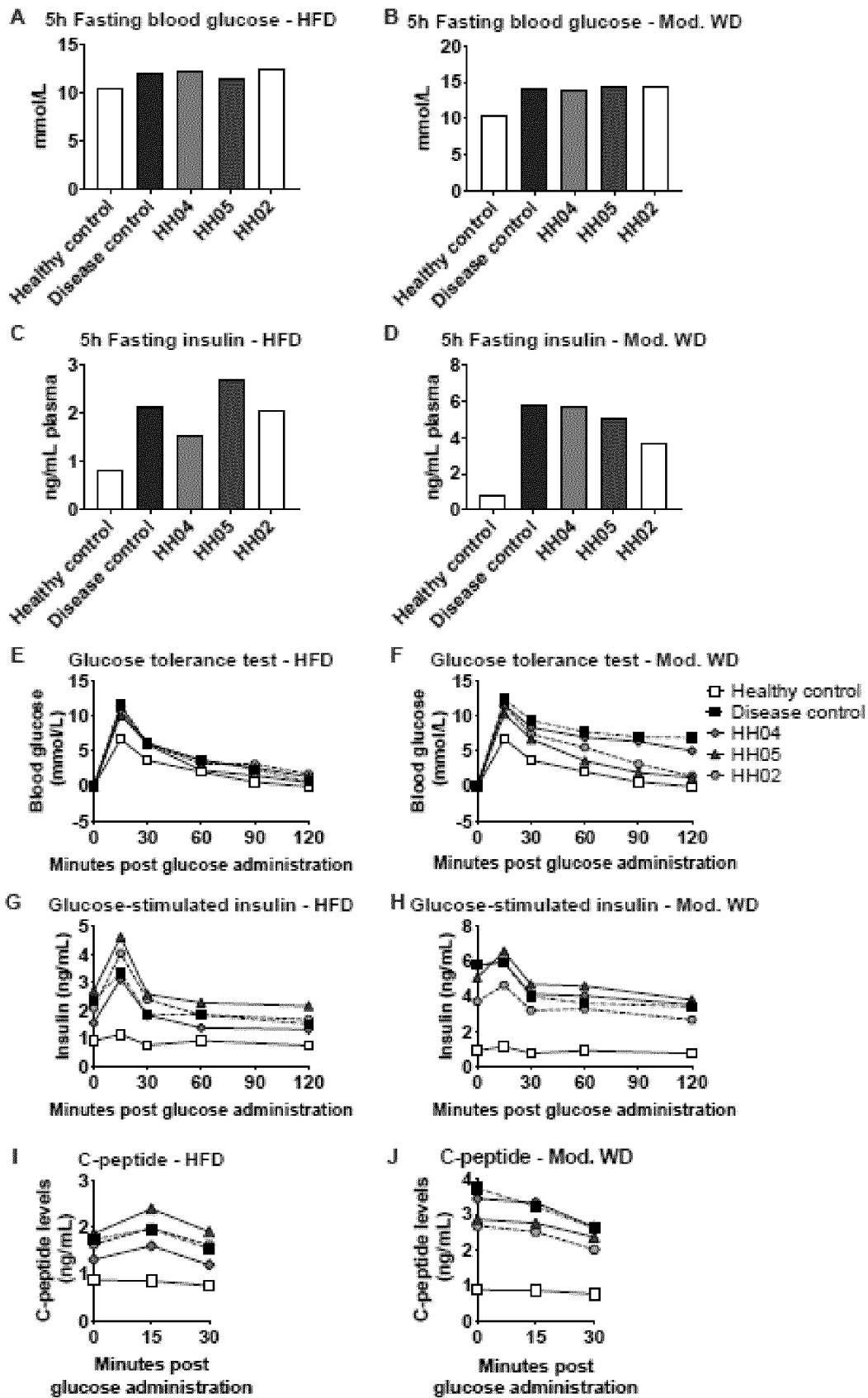

FIG. 39 shows the effect of *Lactobacillus* strains of HH04, HH05, and HH02 on glucose regulation. A) 5 h fasted blood glucose after 10 weeks of modified LFD or HFD feeding and daily gavage treatments. B) As A, but for groups fed LFD or mod. WD. C) 5 h fasting insulin levels after 10 weeks of LFD or HFD feeding and daily gavage treatments. D) As C, but for LFD or mod. WD feeding. E) Change in blood glucose values from fasting values during oral glucose tolerance test after 10 weeks of daily gavage treatment and feeding of either LFD or HFD. F) As E, but depicting LFD or mod. WD fed groups. G) Plasma levels of the endogenous insulin response to the glucose challenge in groups fed LFD or HFD. H) As G, but depicting groups fed LFD or mod. WD. I) C-peptide levels in plasma during the challenge in groups fed LFD or HFD. J) As I, but groups fed LFD or mod. WD. A-J) Bars mean of 8-9 mice per group. More details about the study can be found in example 12.

DETAILED DESCRIPTION OF THE INVENTION

*Lactobacillus* Strains

The present invention relates to *Lactobacillus* strains, cell components, metabolites and/or any secreted molecules thereof, having the ability of improving the metabolic health, such as alleviating prediabetes, of a mammalian subject.

When used herein the term "*Lactobacillus* strain" or "*Lactobacillus* strains" shall mean one or more *Lactobacillus* strains alone or in combination with cell components, metabolites and/or any secreted molecules thereof.

The term "prediabetes" is used for the condition in a subject in which not all of the symptoms required to diagnose diabetes are present, but e.g. blood sugar is abnormally high. As used herein prediabetes includes conditions resulting in symptoms such as e.g. insulin resistance, high blood glucose, low-grade inflammation and/or impaired gut barrier function, i.e. where the gut barrier function is diminished in function.

In one aspect, the *Lactobacillus* strain of the invention survives in the gastrointestinal (GI) tract.

The term "survive in the gastrointestinal (GI) tract" is herein used to mean that the strain is active after passing the GI tract. Survival in the intestinal tract is e.g. determined by identifying the strain in fecal samples of a subject who has been administered the strain such as by oral intake.

The *Lactobacillus* strains of the invention may have the ability of improving one or more prediabetes symptoms such as e.g. insulin resistance, high-blood glucose, low-grade inflammation and/or gut barrier function. One or more *Lactobacillus* strains of the invention or a composition comprising such may in one aspect improve the postprandial glycemic response of a subject, and/or alleviate insulin resistance of a subject.

The *Lactobacillus* strains of the invention may also or alternatively have the ability of improving one or more type 2 diabetes symptoms such as e.g. insulin resistance, high-blood glucose, low-grade inflammation and/or gut barrier function. One or more *Lactobacillus* strains of the invention may in one aspect improve the postprandial glycemic response of a subject, and/or alleviate insulin resistance of a subject. Thus, in one embodiment one or more *Lactobacillus* strains of the invention or a composition comprising such improve the postprandial glycemic response and/or alleviate insulin resistance of a subject having type 2 diabetes.

The *Lactobacillus* strains of the invention may also have the ability of lowering the blood sugar concentration and/or reduce weight gain in an individual receiving a high fat and/or sugar diet wherein one or more *Lactobacillus* strains of the invention is present in the gastrointestinal tract. It should be understood that the *Lactobacillus* strains of the invention have the ability to lower the blood sugar level in individuals having a higher than normal blood sugar level due the particular diet. It is not suspected that the *Lactobacillus* strains of the invention can reduce the blood sugar level below normal blood sugar levels. Thus, one or more *Lactobacillus* strains of the invention can, if present in the gastrointestinal tract of an individual, reduce the weight gain of an individual ingesting a high fat diet, compared with the situation where same individual without the presence of one or more *Lactobacillus* strains of the invention present in the gastrointestinal tract, intaking same diet The *Lactobacillus* strains of the invention may further have the ability of improving microbial dysbiosis induced by a high-fat or westernized diet in the gastrointestinal tract of mammals, in particular human beings. This has the consequence that when present in the gastrointestinal microbiota the *Lactobacillus* strains of the invention have the ability to protect the intestines against conditions and diseases that usually would lead to severe disturbance of the normal gastrointestinal functions. For example, one or more *Lactobacillus* strains of the invention may protect the subject against conditions such as colitis.

The *Lactobacillus* strains of the invention may exert an anti-inflammatory effect on mammalian cells e.g. expressed as a high IL10/IL12 ratio of mammalian cells exposed to one or more *Lactobacillus* strains of the invention in presence of a pro-inflammatory stimulus. In one embodiment, the *Lactobacillus* strains of the invention exert an anti-inflammatory effect on mammalian cells. In a further embodiment, one or more *Lactobacillus* strains of the invention result in a high IL10/IL12 ratio in mammalian cells exposed to the *Lactobacillus* strains in presence of a pro-inflammatory stimulus.

In one embodiment, the *Lactobacillus* strains are selected among *Lactobacillus* strains, *Lactobacillus reuteri* strains or strains belonging to the *Lactobacillus casei* group. Strains belonging to the *Lactobacillus casei* group include *L. casei, L. paracasei* and *L. rhamnosus* strains; preferably *Lactobacillus paracasei* strains, *Lactobacillus paracasei* subsp. *tolerans* or *Lactobacillus paracasei* subsp *paracasei* strains.

Particular preferred strains are selected among the *Lactobacillus* strains deposited at DSMZ-"German Collection of Microorganisms and Cell Cultures" under the deposit numbers: DSM 17648, DSM 32851, DSM 32853, DSM 32910 or DSM 32911.

The *Lactobacillus* strains of the invention may be obtained in any manner known per se, such as cultivating them in suitable media, preferably in such a way and using such media that the microbial preparations thus obtained are suitable for administration to humans and/or animals, and especially are able to colonize the desired parts of the gastrointestinal tract.

Cultivation of the *Lactobacillus* strains of the invention may be performed in standard fermentation equipment suitable for fermenting *Lactobacillus* strains, as will be known in the art.

After cultivation, the *Lactobacillus* strains of the invention are recovered from the fermentation broth and turned into a composition of the invention using techniques known in the art, or alternatively the complete fermentation broth may be turned into the composition according to the invention.

Screening

The *Lactobacillus* strains having the ability of improving the metabolic health, such as alleviating prediabetes, of a mammalian subject may be selected from a pool of candidate strains by one or more screening steps/methods used for screening for the desired properties of the strains.

The one or more screening methods can be selected among screening methods which screen for properties such as immunomodulatory properties, cell adhesion, improvement of gut barrier function, reduction of lipid accumulation in adipocytes, Minimal Inhibitory Concentration (MIC) and/or gastrointestinal survival (GI survival).

Preferred screening methods include, but are not limited to:

PBMC screening, where peripheral blood monocytoid cells are recovered from one or more donors such as two or more, three or more, four or more or five or more, and incubated with a bacterial strain for a given period, whereafter the immunomodulatory profile of the strain is determined by analyzing the impact of the incubation on the level of cytokine production, e.g. Interferon gamma (IFNγ); Interleukin 10 (IL10); IL12; IL13; IL17, IL1B, IL2, IL4, IL5; IL6; IL8, Lipocalin; monocyte chemoattractant protein 1 (MCP-1): Osteopontin and TNFα.

TEER assay (Trans-Epithelial Electrical Resistance as e.g. described in B. Srinivasen et al. (2015). J Lab Autom 2015, 20: 107-126), with or without addition of pro-inflammatory factors having biological activity such as pro-inflammatory cytokines or lipopolysaccharide (LPS).

Dendritic cell (DC) assay, where DCs recovered from one or more donors, such as two or more, three or more, four or more or five or more donors, are matured into inflammatory DCs by incubation with pro-inflammatory stimulus such as cytokines, LPS, TNFα, IFNγ; followed by incubation with a *Lactobacillus* strain for a given period and measurement of cytokines. In a preferred embodiment, DCs are also preincubated with the *Lactobacillus* strain before the pro-inflammatory stimulus is added. *Lactobacillus* strains having the ability of improving the metabolic health, such as alleviating prediabetes, should reduce the IL12 level and the level of anti-inflammatory (or the ratio between antiinflammatory/proinflammatory) cytokines should be higher, compared with strains not having this property.

Adipocytes assay (as described by Zhang et al 2016, Scientific reports 6, 36083), where 3T3-L1 cells are differentiated into matured adipocytes for 10 days, and at a specific time co-incubated with a *Lactobacillus* strain for a given period, and measurements of lipid formation using Oil red O staining of intracellular accumulated lipid as well as gene expression of adipogenesis related genes and pro-inflammatory markers genes by qPCR.

L-cell assay where the human L-cell line, NCI-H716 is grown media containing 10% fetal bovine serum and 1% penicillin/streptomycin, is seeded (passage between 12-20) in the incubator at 37° C./5% $CO_2$ on precoated plate in 24-well plates (200.000 cells/well) and allowed to differentiate for 48 hours, before to be washed twice with Krebs Ringer Buffer containing bovine serum albumin (BSA, 0.2%), and finally co-incubated with diluted supernatants or media controls for 2 h for the glucagon-like peptide 1 (GLP-1) release assay in the incubator at 37° C./5% $CO_2$. Phorbol 12-myristate 13-acetate (10 μM), and Triton X-100 (0.2%) re included each test as GLP-1 positive control and for total release of GLP-1, respectively. All test samples contain 25 μM of a dipeptidyl peptidase-4 inhibitor. Following incubation all supernatants re removed and stored at −20° C. until analyzed for GLP-1. The cells are analyzed for viability. Supernatants are analyzed for GLP-1 using an active GLP-1 ELISA kit.

Bile salt hydrolase assay where *Lactobacillus* strains were incubated in MRS medium (De Man, Rogosa and Sharpe) for 24 h at 37° C. in the presence of bile salts: Glycocholate, Taurocholate, Glycochenodeoxycholate, Taurochenodeoxycholate, Glycodeoxycholate and Taurodeoxycholate. Bile salts were present in 1.56 mg/mL, 0.56 mg/mL, 1.51 mg/mL, 0.54 mg/mL, 1.51 mg/mL and 0.33 mg/mL, respectively. A reference containing the bile salts in absence of any bacteria was used. After incubation, the supernatant was harvested by centrifugation. Samples were extracted with acetic methanol and analyzed on reverse phase (RP) liquid chromatography mass spectroscopy (LCMS) with high mass resolution. The method was set up to quantify all six above mentioned bile salts. The conversion of conjugated bile salts (CBS) expressed in percent were calculated according to the formula CBS [%]=100[%]−(A*100[%]/B). A is the amount of bile salts after 24 h of incubation in presence of bacteria, while B is the amount of bile salts after 24 h of incubation in absence of any bacteria. The higher the CBS value, the more bile salts were converted.

MIC assay: MIC assay (as described by EFSA Panel on additive or products or substances used in animal feeds and endorsed by public consultation on May 2017) where *Lactobacillus* and control strains were grown and dispensed on different serially diluted antibiotics. Breakpoint for each antibiotic were calculated on 3 different replicate experiment. In addition, absence of transferable resistance genes in the genome of the strains were performed using Resfinder analysis (Zanktari et al, 2012, J. Antimicrob. Chemotherapy, PMID 22782487).

In a preferred embodiment, the *Lactobacillus* strains of the invention are selected in a screening protocol comprising at least one screening method selected among PBMC screening, TEER assay, DC assay, adipocytes assay, MIC assay, L-cell assay and Bile salt hydrolase assay.

In another preferred embodiment, the *Lactobacillus* strains of the invention are selected in a screening protocol comprising at least two screening methods selected among PBMC screening, TEER assay, DC assay, adipocytes assay, MIC assay, L-cell assay and Bile salt hydrolase assay.

In another preferred embodiment, the *Lactobacillus* strains of the invention are selected in a screening protocol comprising the steps: PBMC screening, TEER assay, DC assay, L-cell assay and Bile salt hydrolase assay;
- where the IL10/IL12 ratio is above 10 in a PBMC assay e.g. above 20, above 30 or above 50 in a PBMC assay when calculated as an average using PBMCs from at least 3 healthy donors;
- where the *Lactobacillus* strains are capable of increasing the TEER ratio in a TEER assay with a factor of at least 1.15, wherein the TEER ratio is calculated as the quotient of the TEER value after 24 hours of incubation of the Caco2 cells with the *Lactobacillus* strains, to 0 hour in reference to the medium control's TEER value after 24 hours of incubation to 0 hour;
- where the *Lactobacillus* strains are capable of reducing the IL12 level with at least 10%, e.g. at least 20% in a DC assay stimulated by a pro-inflammatory cocktail, in comparison with pro-inflammatory stimulated controls; and
- where the strains perform at least on the same level as strain HH05 in both the bile salt and L-cell assay assay.

In a particular preferred embodiment, the *Lactobacillus* strains of the invention is selected in a screening protocol comprising the steps: PBMC screening, TEER assay, DC assay and L-cell assay.

In one embodiment, the TEER assay used in the invention is with or without addition of proinflammatory factors having biological activity such as pro-inflammatory cytokines or LPS. In another embodiment, the TEER assay used in the invention is with addition of pro-inflammatory factors having biological activity such as pro-inflammatory cytokines or LPS. In an alternative embodiment, the TEER assay used in the invention is without addition of pro-inflammatory factors having biological activity such as pro-inflammatory cytokines or lipopolysaccharide (LPS). In another alternative embodiment, two TEER assay are used in the screening protocol, wherein one TEER assay is without addition of pro-inflammatory factors having biological activity such as pro-inflammatory cytokines or LPS and the other TEER assay is with addition of proinflammatory factors having biological activity such as pro-inflammatory cytokines or LPS. In one embodiment, the TEER assay with addition of pro-inflammatory factors having biological activity is a TEER assay with pro-inflammatory cytokine.

Compositions

The invention further relates to compositions comprising one or more *Lactobacillus* strains of the invention. The composition comprises at least $10^3$ viable cells per grams of the composition, preferably at least $10^4$, $10^5$, $10^6$, $10^7$, $10^8$, $10^9$, $10^{10}$, $10^{11}$, $10^{12}$ or $10^{13}$ viable cells per gram of the composition. In preferred embodiments, the composition comprises $10^6$-$10^{14}$ viable cells per gram of the composition, preferably $10^7$-$10^{13}$ viable cells per gram of the composition.

The one or more *Lactobacillus* strains may be dried, such as freeze-dried or spray dried. When microorganisms are dried, such as freeze-dried, it is important that methods that secure a satisfactory high viable cell number is used and that activities of the selected strains are preserved. Such techniques are known in the art and such methods known in the art are also applicable in the present invention.

Dried, such as freeze-dried preparations may contain suitable adjuvants known per se, for example cryoprotectants such as nutriose, maltose or prebiotics (e.g. galactooligosaccharides). It is preferred to use cryoprotectants that have no or low energetic value or have a very low glycemic index.

The composition may further comprise further ingredients known from the art of preparing foods and food supplements, e.g. selected among fillers, nutrients, preservatives, stabilizing agents, flavouring and colouring agents.

The composition may be in form of powder, paste or gel, and filled into sachet, tablets or capsules. It is preferred that the composition is formulated in discrete dosage formulations such as sachets, tablets or capsules for easy administration.

The composition may be a food supplement, or in the form of a food or food composition. Alternatively, the composition may be in the form of a pharmaceutical composition. In one aspect, the composition is a food, a food composition or a food supplement that comprises one or more *Lactobacillus* strains and optionally one or more acceptable excipients. In another aspect, the composition is a pharmaceutical composition that comprises one or more *Lactobacillus* strains and one or more pharmaceutically acceptable excipients. In one aspect, the pharmaceutical composition is administered together with a drug such as e.g. metformin. In another embodiment, the pharmaceutical composition further comprises a drug such as e.g. metformin.

When the preparation of the invention is in the form of a food supplement, it can be in a form for separate administration, such as a capsule, a tablet, a powder or a similar form, containing preferably a unit dose of the microorganisms, containing $10^7$-$10^{13}$ cells/dose, preferably $10^{10}$-$10^{11}$ cells/dose.

The food supplement can also be in the form of a powder or a similar form, which is added to, or mixed with, a suitable food (composition) or a suitable liquid or solid carrier, for the preparation of a food which is ready for consumption.

For instance, the food supplement can be in the form of a freeze-dried powder, which is reconstituted using a suitable liquid, such as water, oral rehydration solution, milk, fruit juice, or similar drinkable liquids. It can also be in the form of a powder which is mixed with solid foods, or foods with a high water content, such as fermented milk products, for example yoghurt.

The composition of the invention can also be in the form of a food which is ready for consumption. Such a food can for instance be prepared by adding a supplement of the invention as described above to a food or food base known per se; adding the microorganisms (separately or as a mixture) in the amounts required for administration to a food or food base known per se; or by cultivating the required bacteria in a food medium until a food containing the amount of bacteria required for administration is obtained. The food medium is preferably such that it already forms part of the food or will form part of the food after fermentation.

In this respect, food or food base can be either fermented or non-fermented.

The composition of the invention can be foods for oral consumption, for instance a total food or an infant formula.

The composition can further contain prebiotic compounds, in particular, fibers that produce butyrate/butyric acid or propionate/propionic acid upon fermentation; macronutrients containing amino acids such as proteins; and specific vitamins, minerals and/or trace elements. With respect to the latter, and as can be seen from the examples, the presence of increased or moderately high amounts of vitamin A, K, $B_{12}$, biotin, Mg, Cr and Zn can be advantageous, as can the presence of folic acid and omega 3 fatty acids.

The food supplement may further comprise fibers e.g. an amount of at least 0.5 g fiber per 100 g of the total preparation.

As the fibers, the preparation preferably contains a resistant starch or another butyrate generator, as well as a suitable propionate generator such as gums or soy polysaccharides, in the amounts indicated above. Short chain fatty acids such as butyric acid and propionic acid can also be used as such, preferably in a suitably encapsulated form, or as a physiological equivalent thereof, such as sodium propionate, in an amount of at least 0.1 g per 100 g of the total composition.

Amino acids/peptides, vitamins, minerals and trace elements may also be included e.g. in form of yeast extract.

The composition, in particular if the composition is in the form of a total food, can also contain peptides and/or proteins, in particular proteins that are rich in glutamate and glutamine, lipids, carbohydrates, vitamins, minerals and trace elements. The use of glutamine/glutamate precursors, in amounts corresponding to 0.6-3 g glutamine/100 g product, as well as of small polypeptides that have a high content of glutamines, is preferred. Alternatively, proteins that are rich in glutamine, such as milk proteins, wheat proteins or hydrolysates thereof, can be added.

The compositions of the invention may be lactose-free, halal, vegan and/or kosher.

Use

The one or more *Lactobacillus* strains of the invention or a composition comprising the one or more *Lactobacillus* strains of the invention are preferably each administered in an amount of $10^7$-$10^{13}$ cells/day, preferably $10^{10}$-$10^{11}$ cells/day. The cells may be administered as one single dosage or it may be divided in 2 or to up to 10 doses per day, both for adults as well as children.

The compositions are administered orally, typically in connection with a meal.

The one or more *Lactobacillus* strains or the compositions of the invention should be administered daily as long as the individual receiving it has a need therefore, or as long as the individual receiving it wishes to befit from the properties of the *Lactobacillus* strains of the invention, e.g. as long as the individual wishes to stop, reduce or limit weight gains resulting from intake of a too rich diet, and/or improve its postprandial glycemic response, and/or alleviate its insulin resistance.

The term "insulin resistance" is the diminished ability of cells to respond to the action of insulin as transporting glucose (sugar) from the bloodstream into cells. Insulin resistance may e.g. be measured by oral glucose tolerance test and/or glucose stimulated insulin secretion or by measuring fasting insulin and blood glucose.

The term "alleviate insulin resistance" or "alleviating insulin resistance" is used to describe insulin resistance in a subject who has received one or more *Lactobacillus* strains compared to insulin resistance in the same subject who has not received the *Lactobacillus* strains.

Thus, in a preferred embodiment, the one or more *Lactobacillus* strains or compositions of the invention are administered daily for a non-specified period, which in principle could continue for several years.

The *Lactobacillus* strains of the invention have a positive influence on the gastrointestinal tract. For this purpose, the compositions comprising one or more *Lactobacillus* strains can further contain health improving compounds known per se, such as medicaments etc. In particular, the compositions may contain compounds which have a beneficial influence on the gastro-intestinal tract, such as glutamine/glutamate or precursors thereof.

The one or more *Lactobacillus* strains or compositions of the invention can be used for alleviating prediabetes, alleviating or improving type 2 diabetes, improving insulin resistance, improving liver health, reducing gut inflammation, improving gut barrier function, lowering the blood glucose level, and/or preventing or reducing weight gain from a high fat diet in a mammalian subject.

The term "liver health" is herein used for evaluation of liver state (*Lactobacillus* strain treated compared to non-treated disease or healthy controls) by assessing expression of cytokines, triglycerides, cholesterol and/or the liver related enzymes ALT and/or AKT in liver tissue and/or by measuring the liver related enzymes ALT and/or AKT in plasma, serum and/or blood samples and/or by measuring liver weight and/or by evaluating liver state on histological examinations of liver tissue.

The term "gut inflammation" is herein used for when inflammatory factors like pro-inflammatory cytokines are produced in the intestine and/or if a disrupted gut barrier function causes a leaky gut. Gut inflammation and leaky gut can be assessed by measuring cytokine concentrations in intestinal samples and/or plasma samples and/or by measuring LPS in plasma.

The term "gut barrier" is herein used for the ability of the intestinal mucosa to ensure adequate containment of undesirable luminal contents within the intestine while preserving the ability to absorb nutrients. Gut barrier function can be assessed in vitro by measuring TEER across a gut epithelial cell layer and in vivo by measuring LPS levels in plasma samples and/or by in vivo sulfonic assay.

The term "blood glucose level" is herein used for the concentration of glucose in the blood as e.g. measured by enzymatic based assay. Blood glucose concentration is maintained by the body within a narrow range. This tight regulation is referred to as glucose homeostasis. Insulin, which lowers blood sugar, or GLP-1 which enhance insulin secretion, are ones of the most well known of the hormones involved in blood glucose regulation.

The one or more *Lactobacillus* strains or compositions of the invention can be used for improving the metabolic health, such as alleviating prediabetes and/or type 2 diabetes, of an individual. In one aspect of the invention, the one or more *Lactobacillus* strains or compositions are used for improving or alleviating one or more prediabetes and/or type 2 diabetes symptoms such as e.g. insulin resistance, high-blood glucose, low-grade inflammation and/or gut barrier function. In a further or another aspect, the one or more *Lactobacillus* strains or compositions are used for improving the postprandial glycemic response of a subject, and/or alleviating insulin resistance of a subject. In a yet further or another aspect, the one or more *Lactobacillus* strains or compositions are used for preventing or reducing colitis. In a still further or another aspect, the one or more *Lactobacillus* strains or compositions are used for reducing weight gain in individuals having a high fat and/or high sugar intake. In one particular aspect of the invention, the one or more *Lactobacillus* strains or compositions are used for improving or alleviating two or more prediabetes and/or type 2 diabetes symptoms selected from the group consisting of insulin resistance, high-blood glucose, low-grade inflammation and gut barrier function. In another particular aspect of the invention, the one or more *Lactobacillus* strains or compositions are used for improving or alleviating three or more prediabetes and/or type 2 diabetes symptoms selected from the group consisting of insulin resistance, high-blood glucose, low-grade inflammation and gut barrier function. In yet another particular aspect of the invention, the one or more *Lactobacillus* strains or compositions are used for improving or alleviating the prediabetes and/or type 2 diabetes symptoms: Insulin resistance, high-blood glucose, low-grade inflammation and gut barrier function.

Preferred Embodiments

The invention can also be described by the following numbered embodiments:

Embodiment 1. A *Lactobacillus* strain having the ability of improving the metabolic health, such as alleviating prediabetes, or having the ability to lower the blood glucose level in a mammalian subject.

Embodiment 2. The *Lactobacillus* strain according to embodiment 1, where the strain has the ability of alleviating prediabetes.

Embodiment 3. The *Lactobacillus* strain according to embodiment 1 or 2, where the strain has the ability of improving or alleviating one or more prediabetes symptoms selected from the group consisting of: Insulin resistance, high-blood glucose, low-grade inflammation and gut barrier function.

Embodiment 4. The *Lactobacillus* strain according to any of the preceding embodiments, where the strain has the ability of preventing and/or alleviating type 2 diabetes.

Embodiment 5. The *Lactobacillus* strain according to any of the preceding embodiments, where the strain has the ability of preventing and/or alleviating one or more type 2 diabetes symptoms selected from the group consisting of: Insulin resistance, high-blood glucose, low-grade inflammation and gut barrier function.

Embodiment 6. The *Lactobacillus* strain according to any of the preceding embodiments, where the strain has the ability of improving the postprandial glycemic response of a subject, and/or alleviating insulin resistance of a subject.

Embodiment 7. The *Lactobacillus* strain according to any of the preceding embodiments, where the strain survives in the gastrointestinal (GI) tract.

Embodiment 8. The *Lactobacillus* strain according to any of the preceding embodiments, where the strain is selected in a screening protocol comprising at least one screening method selected among PBMC screening, TEER assay, DC assay, adipocytes assay, L-cell assay, bile salt hydrolase assay and MIC assay.

Embodiment 9. The *Lactobacillus* strain according to any of the preceding embodiments, where the strain is selected in a screening protocol comprising at least two screening methods selected among PBMC screening, TEER assay, DC assay, adipocytes assay, L- cell assay, bile salt hydrolase assay and MIC assay.

Embodiment 10. The *Lactobacillus* strain according to any of the preceding embodiments, where the strain is selected in a screening protocol comprising the methods: PBMC screening, TEER assay, TEER assay with addition of pro-inflammatory cytokine and DC assay.

Embodiment 11. The *Lactobacillus* strain according to any of the preceding embodiments, wherein the IL10/IL12 ratio is above 10 in a PBMC assay e.g. above 20, e.g. above 30, e.g. above 50 calculated as an average using PBMCs from at least 3 healthy donors.

Embodiment 12. The *Lactobacillus* strain according to any of the preceding embodiments, wherein the strain is capable of increasing the TEER ratio in a TEER assay with a factor of at least 1.15, where the TEER ratio is calculated as quotient of the TEER value after 24 hour of incubation of the PBMCs with the *Lactobacillus* strain, to 0 hour in reference to the medium control's TEER value after 24 hour of incubation to 0 hour Embodiment 13. The *Lactobacillus* strain according to any of the preceding embodiments, wherein the strain is capable of reducing the IL12 level with at least 10%, preferably at least 20% in a DC assay stimulated by a pro-inflammatory cocktail, in comparison with proinflammatory stimulated controls.

Embodiment 14. The *Lactobacillus* strain according to any of the preceding embodiments, being a *Lactobacillus reuteri* strain or a *Lactobacillus brevis* strain or belonging to the *Lactobacillus casei* group.

Embodiment 15. The *Lactobacillus* strain according to any of the preceding embodiments, being a *Lactobacillus reuteri* strain or belonging to the *Lactobacillus casei* group.

Embodiment 16. The *Lactobacillus* strain according to any of the preceding embodiments, being a *Lactobacillus reuteri* strain, *Lactobacillus casei* strain, *Lactobacillus paracasei* strain and/or *Lactobacillus rhamnosus* strain.

Embodiment 17. The *Lactobacillus* strain according to embodiment 14 or 15, wherein the *Lactobacillus* strain is of the *Lactobacillus casei* group and is selected from *Lactobacillus* casei, *Lactobacillus paracasei* and *Lactobacillus* rhamnosus.

Embodiment 18. The *Lactobacillus paracasei* strain according to embodiment 17, which is selected from *Lactobacillus paracasei* ssp. *tolerans* and *Lactobacillus paracasei* ssp. *paracasei* strains.

Embodiment 19. The *Lactobacillus* strain according to any of the preceding embodiments, wherein the strain is selected among the strains deposited as DSM 17648, DSM 32910, DSM 32911, DSM 32851 and DSM 32853 and mutants thereof.

Embodiment 20. The *Lactobacillus* strain according to embodiment 19, wherein the mutants are derived from natural evolution.

Embodiment 21. The *Lactobacillus* strain according to embodiment 19, wherein the mutants comprise between 1 to 50 amino acid substitutions, deletions and/or additions, such as between 1 to 40, 1 to 30, 1 to 20, or 1 to 10 amino acid substitutions, deletions and/or additions to the *Lactobacillus* strain deposited as DSM 17648, DSM 32910, DSM 32911, DSM 32851 or DSM 32853.

Embodiment 22. A composition comprising one or more *Lactobacillus* strains according to any of the embodiments 1-21.

Embodiment 23. The composition according to embodiment 22, comprising two or more *Lactobacillus* strains according to any of the embodiments 1 to 21, such as three or more, four or more or five or more *Lactobacillus* strains according to any of the embodiments 1 to 21.

Embodiment 24. The composition according to any of embodiments 22 to 23, wherein the composition comprises the *Lactobacillus* strain deposited as DSM 17648 and one or more *Lactobacillus* strains selected from the strains deposited as DSM 32910, DSM 32911, DSM 32851 and DSM 32853.

Embodiment 25. The composition according to any of embodiments 22 to 23, wherein the composition comprises the *Lactobacillus* strain deposited as DSM 32910 and one or more *Lactobacillus* strains selected from the strains deposited as DSM 17648, DSM 32911, DSM 32851 and DSM 32853.

Embodiment 26. The composition according to any of embodiments 22 to 23, wherein the composition comprises the *Lactobacillus* strain deposited as DSM 32911 and one or more *Lactobacillus* strains selected from the strains deposited as DSM 17648, DSM 32910, DSM 32851 and DSM 32853.

Embodiment 27. The composition according to any of embodiments 22 to 23, wherein the composition comprises the *Lactobacillus* strain deposited as DSM 32851 and one or more *Lactobacillus* strains selected from the strains deposited as DSM 17648, DSM 32910, DSM 32911 and DSM 32853.

Embodiment 28. The composition according to any of embodiments 22 to 23, wherein the composition comprises the *Lactobacillus* strain deposited as DSM 32853 and one or more *Lactobacillus* strains selected from the strains deposited as DSM 17648, DSM 32910, DSM 32911 and DSM 32851.

Embodiment 29. The composition according to any of embodiments 22 to 28, comprising up to five *Lactobacillus* strains according to any of the embodiments 1 to 21 such as up to four, three or two *Lactobacillus* strains according to any of the embodiments 1 to 21.

Embodiment 30. The composition according any of embodiments 22 to 29, wherein the composition further comprises a microbial strain from a different species.

Embodiment 31. The composition according to embodiment 30, wherein the further microbial strain is selected from a *Lactobacillus rhamnosus* strain and a strain belonging to the Akkermansia species.

Embodiment 32. The composition according any of embodiments 22 to 31, where the composition further comprises cell components, metabolites and/or secreted molecules thereof.

Embodiment 33. The composition according to embodiment 32, wherein the cell components, metabolites and/or secreted molecules are from the retentate of the culture after fermentation and centrifugation.

Embodiment 34. The composition according to any of embodiments 22 to 33, wherein the strains are dried such as freeze-dried or spray-dried.

Embodiment 35. The composition according to any of embodiments 22 to 33, wherein the strains are freeze-dried.

Embodiment 36. The composition according to any of embodiments 22 to 35, where the composition comprises $10^6$-$10^{14}$ colony forming units (CFU) per gram of the composition, preferably $10^7$-$10^{13}$, preferably $10^8$-$10^{12}$ CFU per gram.

Embodiment 37. The composition according to any of embodiments 22 to 36, wherein the composition is formulated as unit dosis formulations each comprising $10^6$-$10^{14}$ colony forming units (CFU) per unit, preferably $10^7$-$10^{13}$, preferably $10^6$-$10^{12}$ CFU per unit. Embodiment 38. The composition according to any of embodiments 22 to 37, where the composition comprises between $10^6$ and $10^{14}$, such as between $10^6$ and $10^{13}$ cells, between $10^8$ and $10^{12}$ cells or between $10^9$ and $10^{11}$ cells, where the total number refers to the total amount of living and dead cells.

Embodiment 39. The composition according to any of embodiments 22 to 37, where the composition comprises between $10^6$ and $10^{14}$, such as between $10^6$ and $10^{13}$ cells, between $10^8$ and $10^{12}$ cells or between $10^9$ and $10^{11}$ cells, where the total number refers to the total amount of living cells.

Embodiment 40. The composition according to any of embodiments 22 to 37, where the composition comprises between $10^6$ and $10^{14}$, such as between $10^6$ and $10^{13}$ cells, between $10^8$ and $10^{12}$ cells or between $10^9$ and $10^{11}$ cells, where the total number refers to the total amount of dead cells.

Embodiment 41. The composition according to any of embodiments 22 to 40, wherein the composition is a pharmaceutical composition comprising the *Lactobacillus* strains and one or more pharmaceutically acceptable excipients.

Embodiment 42. The composition according to any of embodiments 22 to 40, wherein the composition is a food, a food supplement or a food composition.

Embodiment 43. The composition according to embodiment 42 which comprises one or more acceptable excipients.

Embodiment 44. The composition according to any of embodiments 42 to 43, wherein the composition is ready for consumption.

Embodiment 45. The composition according to any of embodiments 42 to 44, which comprises further food supplements.

Embodiment 46. The composition according to embodiment 45, wherein the further food supplements are selected from one or more prebiotics, enzymes, vitamins and minerals.

Embodiment 47. The composition according to any of embodiments 22 to 46, where the composition further comprises cell components, metabolites and/or secreted molecules thereof.

Embodiment 48. A dietary supplement comprising one or more *Lactobacillus* strains according to any of the embodiments 1 to 21.

Embodiment 49. The dietary supplement according to embodiment 48, further comprising one or more narratively beneficial ingredients such as prebiotics, enzymes, vitamins and/or minerals.

Embodiment 50. Use of one or more *Lactobacillus* strains according to any of embodiments 1 to 21 or a composition according to any of embodiments 22 to 47, for the improvement of the metabolic health, such as alleviating prediabetes, of a mammalian subject.

Embodiment 51. Use of one or more *Lactobacillus* strains according to any of embodiments 1 to 21 or a composition according to any of embodiments 22 to 47, for alleviating prediabetes, preventing or alleviating type 2 diabetes, alleviating insulin resistance, improving liver health, reducing gut inflammation, improving gut barrier function, lowering the blood glucose level, and/or preventing or reducing weight gain from a high fat diet in a mammalian subject.

Embodiment 52 The use according to embodiment 50 or 51, wherein the use is for alleviating prediabetes, preventing or alleviating type 2 diabetes, alleviating insulin resistance, improving liver health, reducing gut inflammation, and/or improving gut barrier function in a mammalian subject.

Embodiment 53. The use according to any of embodiments 50 to 52, wherein the use is for alleviating insulin resistance, improving liver health, reducing gut inflammation and/or improving gut barrier function in a mammalian subject.

Embodiment 54. Use of one or more *Lactobacillus* strains according to any of embodiments 1 to 21 or a composition according to any of embodiments 22 to 47, for the lowering the blood glucose level in a mammalian subject.

Embodiment 55. Use of one or more *Lactobacillus* strains according to any of embodiments 1 to 21 or a composition according to any of embodiments 22 to 47, for the prevention or reduction of weight gain in an individual having a high fat diet.

Embodiment 56. The use according to any of embodiments 50 to 55, where the mammal is a human.

Embodiment 57. The use according to any of embodiments 50 to 56, where $10^6$-$10^{14}$ colony forming units (CFU) are administered to the mammalian subject on a daily basis, preferably $10^7$-$10^{13}$, preferably $10^8$-$10^{12}$.

Embodiment 58. A method for screening for a *Lactobacillus* strain according to any of the embodiments 1 to 21, using a screening protocol comprising at least one screening method selected among PBMC screening, TEER assay, DC assay, adipocytes assay, L-cell assay, bile salt hydrolase assay and MIC assay.

Embodiment 59. The method according to embodiment 58, using a screening protocol comprising at least two screening methods selected among PBMC screening, TEER assay, DC assay and adipocytes assay.

Embodiment 60. The method according to embodiment 58 or 59, using a screening protocol comprising the screening methods: PBMC screening, TEER assay, TEER assay with addition of pro-inflammatory cytokine and DC assay.

Embodiment 61. The method according to any of embodiments 58 to 60, using a screening protocol comprising the screening methods: PBMC screening, TEER assay, DC assay and L-cell assay.

EXAMPLES

Materials and Methods

Standard media were used for growing *Lactobacillus, Enterococcus, Micrococcus* and *Bifidobacterium* strains, for example a medium providing 15-20 g peptone or tryptone per litre and about 5 g yeast extract per litre. For preparing the media the standard procedure was applied (concentration of components, sterilization, inoculation) and the microorganism was allowed to grow at elevated temperature (e.g. 35-42° C.) for a sufficient time (e.g. 8-48 hours).

Example 1. Screening for Suitable *Lactobacillus* Strains

*Lactobacillus* strains having a beneficial impact on the metabolic health, such as alleviating prediabetes, were found using the screening protocol outlined below.
1. Prescreening: 640 *Lactobacillus* strains were screened by analyzing the IL10/IL12 ratio as an indicator on the immunomodulatory potential of the strains in an PBMC screening assay:

For the Peripheral Blood Mononuclear Cells (PBMC) assay, PBMC from one donor were co-incubated, after 24 hours of acclimatization, for 24 hours with the *Lactobacillus* strains in the absence of further pro-inflammatory stimulus. After the incubation appropriate dilutions of the supernatant containing the cytokines were measured by Luminex Assay (Invitrogen) according to the manufacturer's instructions, and/or ELISA and the IL10/IL12 ratios were determined.

180 strains with an IL10/IL12 ratio >3 were selected in the pre-screening.

2. Screening immunomodulation and gut integrity

The 180 strains selected in the prescreening were subjected to a PBMC confirmatory screening that was identical to the prescreening except that the strains were tested on PBMCs from three different donors in order to confirm the beneficial IL10/IL12 ratio. Besides the IL10/IL12 ratio, 14 other cytokines were measured.

Strains were further subjected to a TEER assessment (Trans-Epithelial Electrical Resistance) w/o addition of any pro-inflammatory stimulus for example TNFα, (as described in B. Srinivasen et al. (2015). J Lab Autom 2015, 20: 107-126), in order to evaluate the impact of the *Lactobacillus* strains on the gut integrity. TEER measurements were made after 0 and 24 hours.

20 strains where the PBMC confirmatory screening confirmed IL10/IL12 ratio >3 and that led to an increase in TEER values were selected for next screening method.

3. Hit confirmation in presence of pro-inflammatory triggers

In this confirmation step 20 strains selected in the TEER assessment without TNFα in step 2, were also subjected to a TEER assessment with TNFα addition.

*Lactobacillus* strains that led to increase in TEER values in comparison with the control without strains were selected.

These strains were further screened in a DC assay. For this test, DC were generated from PBMCs derived from 3 donors. DC were matured into inflammatory DCs by treatment with 0.1 µg/mL LPS+50 ng/ml TNF-α+20 ng/ml IFNγ and incubated for 4 hours. Aliquots of the mature DCs were incubated with each *Lactobacillus* strain in 4 different doses, whereafter cytokine levels were determined using Luminex.

*Lactobacillus* strains that reduced the IL12 induction compared to the control composition without strains were selected.

HH01
Species: *Lactobacillus* reuteri
Confirmed by 16S and WGS
Deposit number: DSM 17648.
HH02
Species: *Lactobacillus* reuteri
Confirmed by 16S and WGS
Deposit number: DSM 32910.
HH03
Species: *Lactobacillus* rhamnosus
Confirmed by 16S and WGS
Deposit number: DSM 32911
HH04
Species: *Lactobacillus paracasei* ssp. *tolerans*
Confirmed by 16S and WGS
Deposit number: DSM 32851
HH05
Species: *Lactobacillus paracasei* ssp. *paracasei*
Confirmed by 16S and WGS
Deposit number: DSM 32853

Example 2. Induction of Cytokines in PBMC

The strains HH01-HH05 selected in example 1 were further characterized in vitro.

$1 \times 10^6$ PBMCs/mL isolated from healthy donors incubated with vehicle or vehicle comprising $1 \times 10^6$ *Lactobacillus* strains/mL HH01-HH05 in a total volume of 1 ml for 24 hours. Cytokines IL12, MCP-1 and osteopontin were measured using Luminex, according to the manufacturer's instructions. As vehicle was used Phosphate Buffered Saline (PBS) pH 7.4 without $MgCl_2$ (Cat. 10010-023, Gibco).

Figure 1:
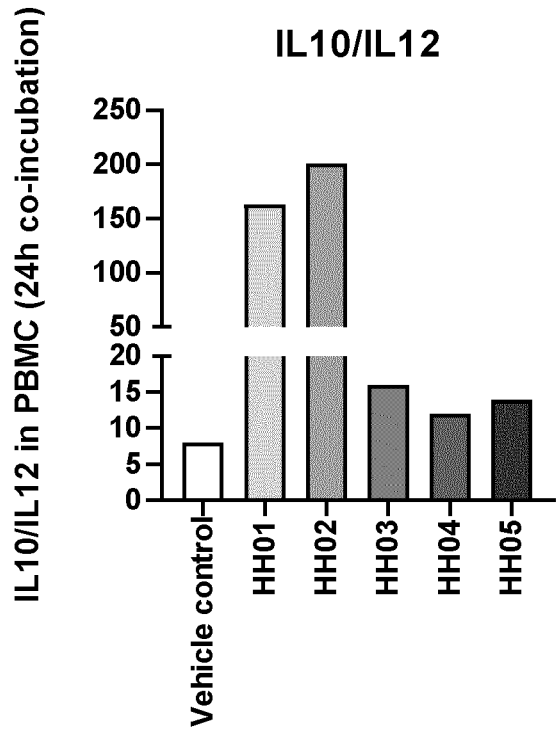
FIG. 1 shows a bar graph representing the ratio of anti-inflammatory cytokine interleukin 10 (IL10) and pro-inflammatory cytokine interleukin 12 (IL12) measured by Luminex or ELISA in the supernatants of peripheral blood mononuclear cells (PBMCs) incubated with Lactobacillus strains for 24 h. Each column represents the mean of 3 experiments performed with healthy PBMC donors. For more details see example 2.
Figure 2:
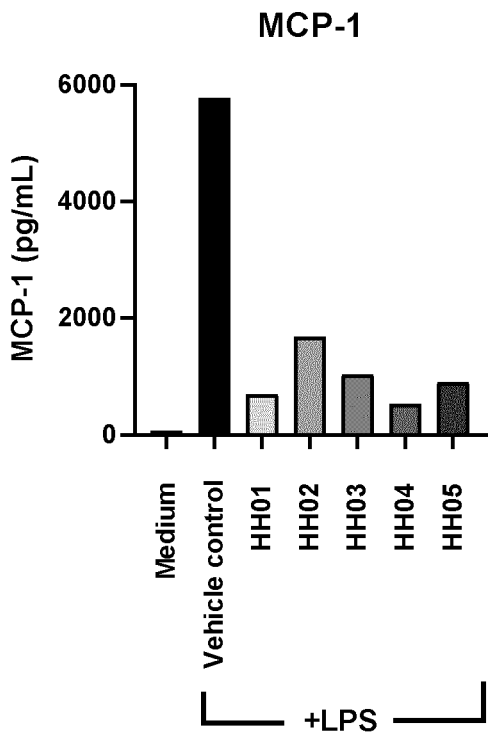
FIG. 2 shows a bar graph representing the pro-inflammatory cytokine monocyte chemoattractant protein 1 (MCP-1) measured by Luminex in the supernatants of PBMCs stimulated with a pro-inflammatory stimulus (lipopolysaccharide) and incubated with Lactobacillus strains for 24 h. Each column represents the mean of 3 experiments performed with healthy PBMC donors. For more details see example 2.

Results:

The strains HH01-HH05 induced an increased IL10/IL12 ratio compared with the vehicle control, confirming that the selected strains have anti-inflammatory properties (FIG. 1). FIG. 2 shows the content of MCP-1 in the supernatant of the PBMCs, stimulated with a proinflammatory stimulus lipopolysaccharide (LPS). The results showed that with vehicle alone high production of MCP-1 was seen, whereas the strains HH01-HH05 reduced the MCP-1 induction significantly, supporting the anti-inflammatory properties of these strains.

Figure 3:
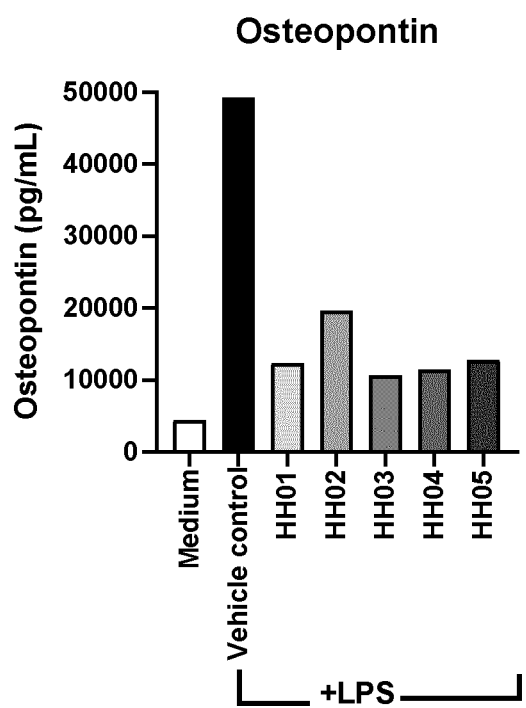
FIG. 3 shows a bar graph representing the pro-inflammatory osteopontin measured by Luminex in the supernatants of PBMCs stimulated with a pro-inflammatory stimulus (lipopolysaccharide) and incubated with Lactobacillus strains for 24 h. Each column represents the mean of 3 experiments performed with healthy PBMC donors. For more details see example 2.

FIG. 3 shows the content of Osteopontin in the supernatant of the PBMCs, stimulated with a pro-inflammatory stimulus (lipopolysaccharide). The results showed that with vehicle alone a high production of Osteopontin was seen, whereas the strains HH01-HH05 reduced the osteopontin induction significantly, confirming the anti-inflammatory properties of these strains.

Example 3. Induction of Cytokines in Dendritic Cells

In a first set of assay, dendritic cells (DCs) were recovered from PBMCs from 3 healthy donors and aliquots were incubated with vehicle or vehicle comprising *Lactobacillus* strains HH01, HH03 or HH05 for 24 hours. The mixtures were centrifuged and the supernatant collected and the MCP-1, Osteopontin and IL12p70 were measured using Luminex, (Invitrogen), according to the manufacturer's instructions.

Figure 4:
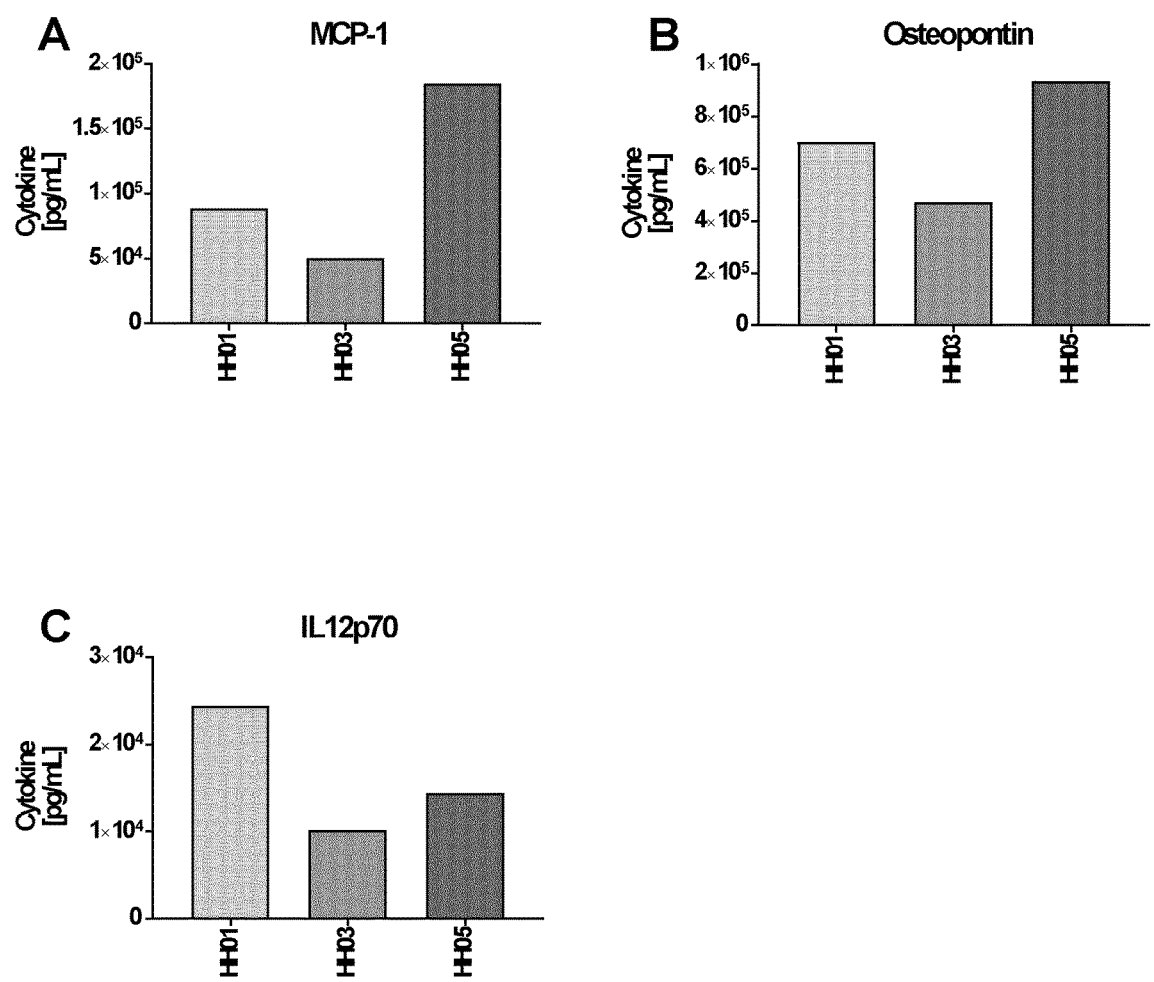
FIG. 4 shows bar graphs showing cytokines secreted by dendritic cells (DC) in a proinflammatory environment. Each column represents the mean of n=1-3. A: MCP-1; B: Osteopontin; C: IL12p70. The supernatant was harvested by centrifugation and used for cytokine analysis using a multiplex assay. For more details see example 3.

In a second set of assays, DC were recovered from PBMCs from 12 healthy donors and aliquots were incubated with vehicle or vehicle comprising *Lactobacillus* strains HH02, HH04 or HH05 for 24 hours. The mixtures were centrifuged and the supernatant collected and the IL10, IL12p70, MCP-1 were measured using Luminex, (Invitrogen), according to the manufacturer's instructions Results:

In the first set of DC assays, results show that the concentrations of the pro-inflammatory cytokines MCP-1, IL12, and osteopontin were the lowest when DC were co-incubated with the *Lactobacillus* strain HH03, compared to strain HH01 and strain HH05 (FIG. 4).

In the second set of DC assays, results show that *Lactobacillus* strains HH01, HH04 and HH05 simulated with the low-grade inflammation cocktails all induced an increased IL10/IL12p70 ratio compared to the control simulated with the low-grade inflammation cocktail alone. In addition, DCs stimulated by low-grade inflammatory cocktail produced MCP-1, but were reduced compared to the cocktail control, confirming that the selected strains have anti-inflammatory properties.

Example 4. Induction of Cytokines in DC Cultures

The strains HH02, HH04 and HH05 selected in example 1 were further characterized in a co-incubation assay with DCs. Selected cytokines were measured after stimulation with a proinflammatory cocktail.

Human PBMCs were isolated from buffy coat (N=12) and CD14+ monocytes were purified by positive selection (CD14 microbeads, Miltenyi Biotech). Monocytes were cultured for 6 days with IL4 (20 ng/mL) and GM-CSF (20 ng/mL) for differentiation into immature DCs (imDCs). For differentiation into mature DCs, $1 \times 10^5$ cells were cultured with selected *Lactobacillus* strains HH02 ($10^6$ *Lactobacillus* strains/mL) and a low-grade inflammation cocktail composed of TNFα (10 ng/mL), IFNγ (10 ng/mL) and LPS (100 ng/mL). The imDCs were stimulated by *Lactobacillus* strains for 4 hours before adding the low-grade inflammation cocktail for additional 16 hours. DC maturation was evaluated following in vitro stimulation by BD Cytometric Bead Array (CBA) to measure DC derived IL10, IL12p70, MCP-1 and IL6. Effect of strains HH02, HH04, HH05 on these cytokines were compared with the control without strain stimulated solely with the proinflammatory cocktail.

Results

Figure 5:
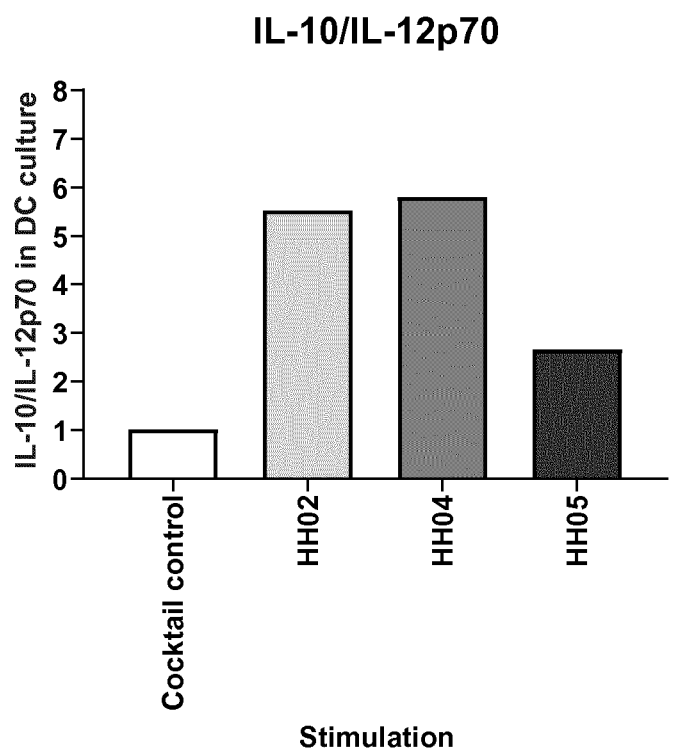
FIG. 5 shows a bar graph representing the ratio of anti-inflammatory cytokine interleukin 10 (IL10) and pro-inflammatory cytokine interleukin 12p70 (IL12p70) measured by BD™ Cytometric Bead Array (CBA) in the supernatants of DC culture incubated with Lactobacillus and low-grade inflammatory cocktail composed of TNFα+IFN-γ+LPS (cocktail). The data is normalized to cocktail control from each donor. DCs were cultured with Lactobacillus for 4 hours before adding cocktail for the remaining 16 hours. Cocktail control is DCs cultured with cocktail for 16 hours. Each column represents the ratio of 12 experiments performed with monocyte derived DCs from individual healthy human PBMC donors.

The results showed that DCs stimulated by low-grade inflammation cocktail produced IL10 and that presence of strains HH02, HH04 and HH05 all increase in IL10 concentration compared to stimulation by cocktail alone, that DCs stimulated by low-grade inflammation cocktail produced IL12p70 and that presence of strains HH02, HH04 and HH05 all increase in IL12p70 concentration compared to stimulation by cocktail alone, and that *Lactobacillus* strains HH01, HH04 and HH05 all induced an increased IL10/IL12p70 ratio compared to the cocktail control (FIG. 5), confirming that the selected strains have anti-inflammatory properties.

Figure 6:
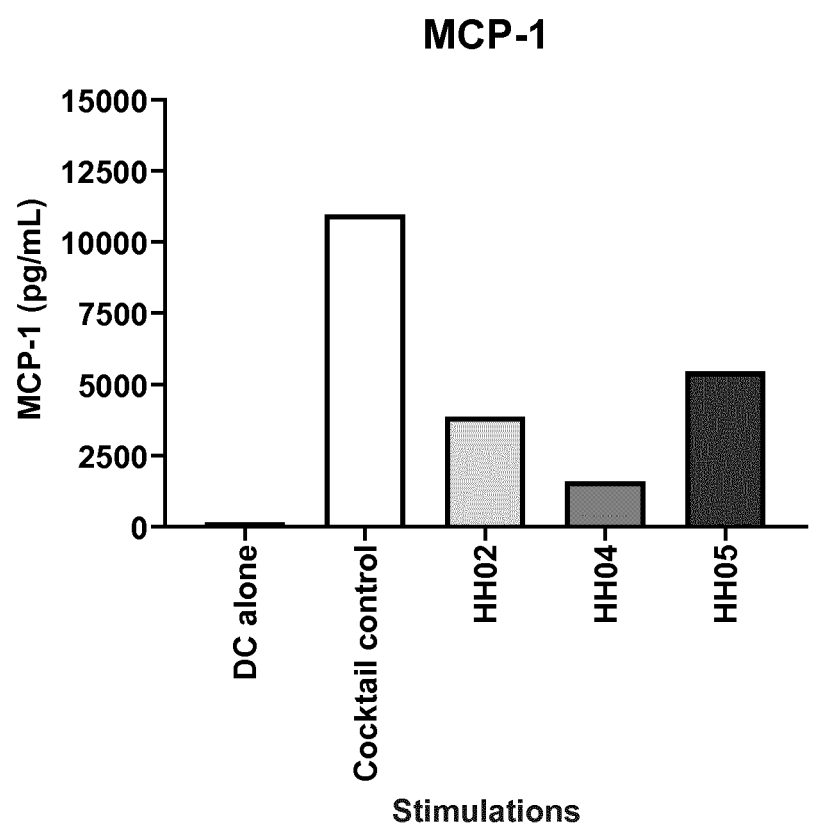
FIG. 6 shows a bar graph representing the mean concentration of monocyte chemotactic protein-1 (MCP-1/CCL2) measured by BD™ Cytometric Bead Array (CBA) in the supernatants of DC culture incubated with Lactobacillus and low-grade inflammatory cocktail composed of TNFα+IFNγ+LPS (cocktail). DCs were cultured with Lactobacillus for 4 hours before adding the cocktail for the remaining 16 hours. Cocktail control is DCs cultured with cocktail for 16 hours. Each column represents the mean of 12 experiments performed with monocyte derived DCs from healthy human PBMC donors.
Figure 7:
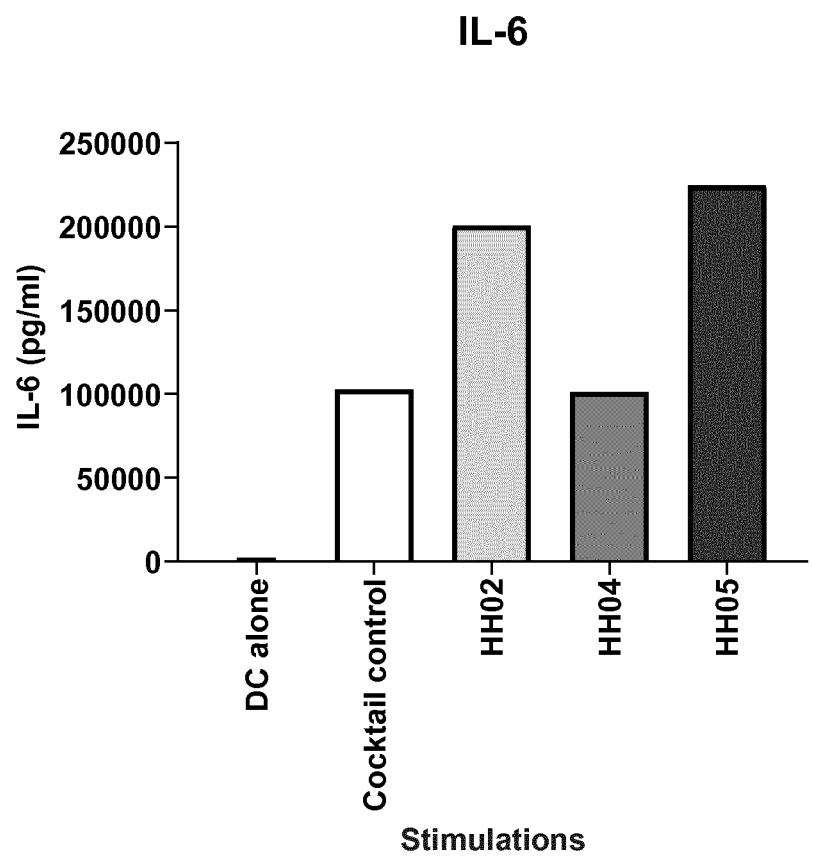
FIG. 7 shows a bar graph representing the mean concentration of cytokine interleukin 6 (IL6) measured by BD Cytometric Bead Array (CBA) in the supernatants of DC culture incubated with *Lactobacillus* and low-grade inflammatory cocktail composed of TNFα+IFNγ+LPS (cocktail). DCs were cultured with *Lactobacillus* for 4 hours before adding the cocktail for the remaining 16 hours. Cocktail control is DCs cultured with cocktail for 16 hours. Each column represents the mean of 12 experiments performed with monocyte derived DCs from healthy human PBMC donors.

Furthermore it was seen, that DCs stimulated by low-grade inflammatory cocktail produced MCP-1, and that presence of *Lactobacillus* strains HH02, HH04 and HH05 all reduced the MCP-1 concentration during culturing (FIG. 6). Additionally, the results showed that DCs stimulated by low-grade inflammation cocktail produced high levels of IL6, and that presence of *Lactobacillus* strains HH04 maintained the IL6 concentration at the level of cocktail control whereas strain HH02 and HH05 increased it (FIG. 7).

Example 5. TEER Assay Performed with *Lactobacillus* Strains HH01-HH05

The TEER assay was performed according to B. Srinivasen et al. (2015). J Lab Autom 2015, 20: 107-126. For this assay CaCo-2 cells, bought at the DSMZ (Deutsche Sammlung von Mikroorganismen and Zellkultur GmbH) running under the order number ACC 169, were used. $2 \times 10^5$ CaCo-2 cells pro mL were seeded and differentiated for 3 weeks. They were incubated for 24 h with vehicle or vehicle containing *Lactobacillus* strains HH01-HH05 in a concentration of $1 \times 10^6$ cells pro mL in the absence of pro-inflammatory stimuli, whereafter the TEER ratios were determined. As vehicle was used Phosphate Buffered Saline pH 7.4 without $MgCl_2$ (Cat. 10010-023, Gibco). A TEER ratio of >1 indicated that the *Lactobacillus* strains were able to strengthen gut barrier function integrity.

CaCo-2 cells were incubated for 24 h with vehicle or vehicle containing *Lactobacillus* strains HH01-HH05 in the presence of pro-inflammatory stimuli in form of 100 ng/mL TNFα, whereafter the TEER ratios were determined. As vehicle was used PBS pH 7.4 without $MgCl_2$ (Cat. 10010-023, Gibco). A TEER ratio of >1 indicated that the *Lactobacillus* strains were able to strengthen the gut barrier function.

Figure 8:
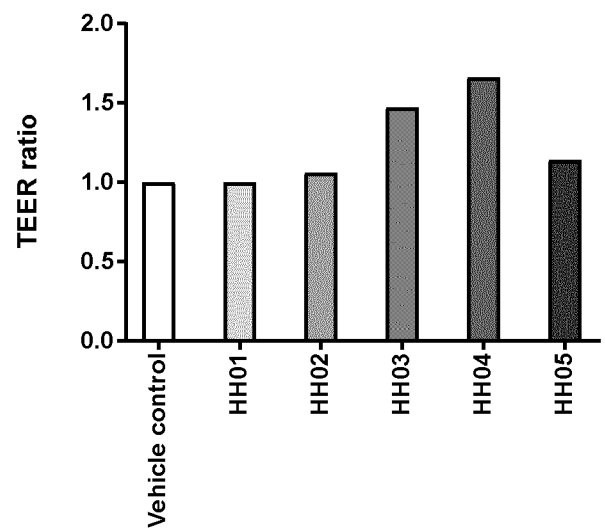
FIG. 8. shows the effect of *Lactobacillus* strains on the strength of the barrier of the epithelial cell line Caco2 at multiplicity of infection (MOI) of 5 after 24 h of incubation. This effect is measured using the transepithelial electrical resistance (TEER) technique and is expressed as TEER ratio. TEER ratio measured A in absence of proinflammatory stimuli and B in the presence of pro-inflammatory stimuli. For more details see example 5.
Figure 8:
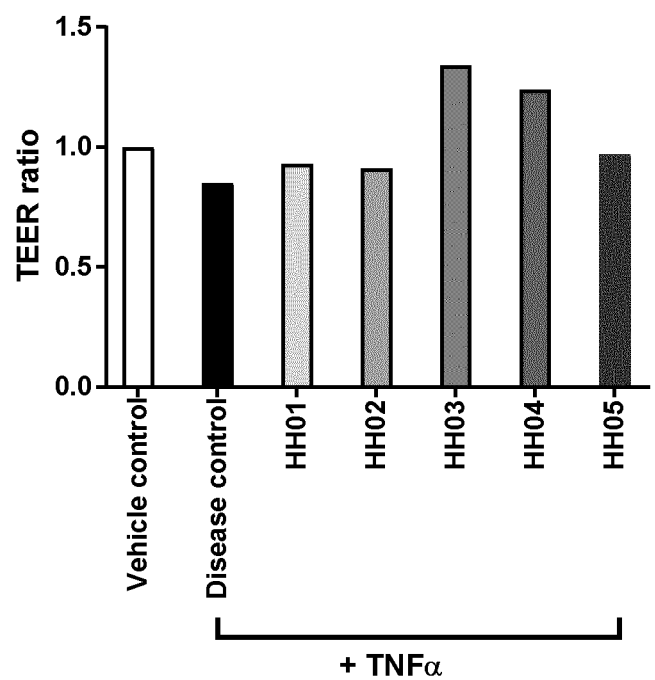

Results:

The TEER data show that the *Lactobacillus* strains HH04 and strain HH03 strengthen the most the intestinal epithelial barrier both in the absence (FIG. 8A) or presence (FIG. 8B) of proinflammatory factors. In presence of pro-inflammatory factors, strains HH01, HH02 and HH05 were also able to increase TEER compare the disease control alone (medium with proinflammatory factors).

Example 6. TEER Assay

Impact of the *Lactobacillus* strains HH02, HH04 and HH05 on the integrity of the epithelial cell line Caco2 barrier in presence of an inflammatory cocktail:

The impact of the *Lactobacillus* strains HH02, HH04 and HH05 on the integrity of the epithelial cell line Caco2 barrier in presence of an inflammatory cocktail was determined using the TEER EVOM2 assay performed in the same way as described under "Example 5. TEER assay" with following modification. An inflammatory cocktail, which contains TNFα-alpha (100 ng/mL) and INFγ-gamma (10 ng/mL), were added on the basolateral side when the co-incubation started.

Figure 9:
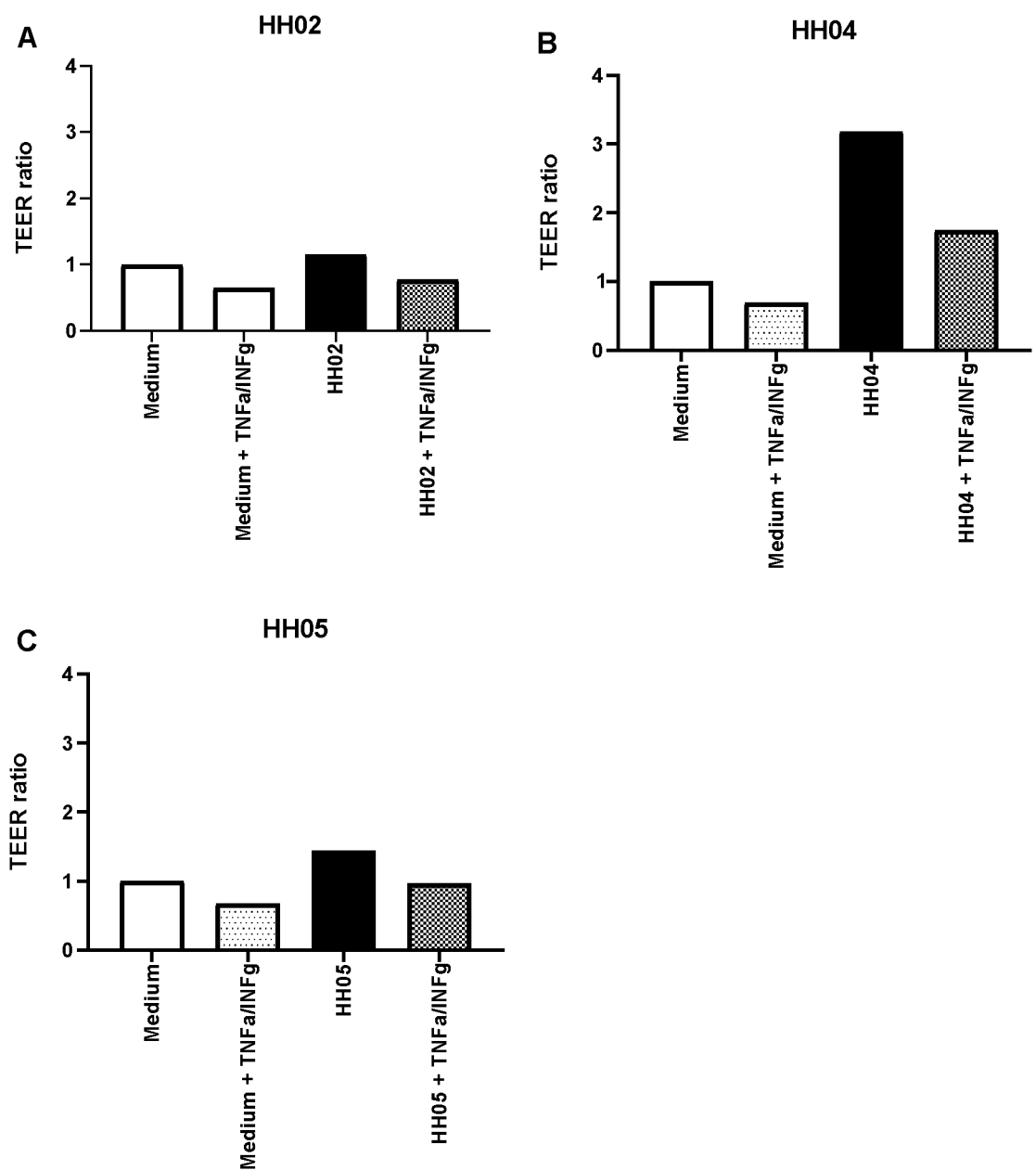
FIG. 9 shows the effect of *Lactobacillus* on the strength of the barrier of the epithelial cell line Caco2 in presence and absence of *Lactobacillus* strains at a MOI of 5 and pro-inflammatory cocktail, which consists of TNF-alpha (TNFα) and INF-gamma (INFγ) after 24 h of incubation. A) TEER ratios of the *Lactobacillus* HH02. Mean of 2-3 per group. B) TEER ratios of the *Lactobacillus* HH04. Mean of 2-3 per group. C) TEER ratios of the *Lactobacillus* HH05. Mean of 2-3 per group.

Results:

The results showed that the inflammatory cocktail decreased the TEER ratio, which is an indication for a weakened integrity of Caco2 barrier. This effect was compensated by the tested strains HH02, HH04 and HH05, most strongly by HH04 (FIG. 9).

Figure 10:
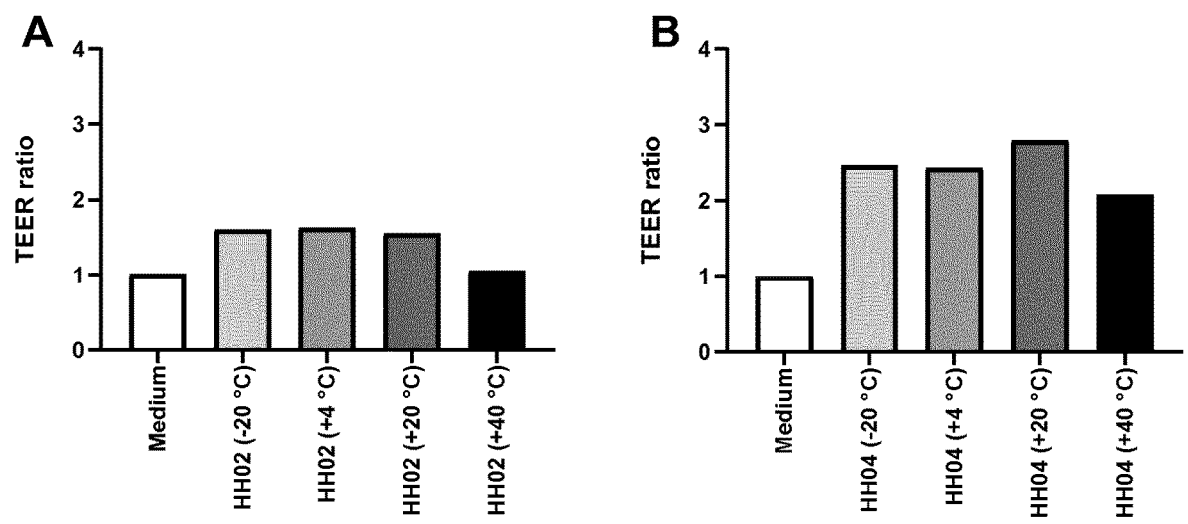
FIG. 10 shows the transepithelial electrical resistance (TEER) of the freeze-dried *Lactobacillus* strains HH02 and HH04, which were stored at −20° C., 4° C., 25° C. and 40° C. for one month after 24 h co-incubation with the epithelial cell Caco2 at a multiplicity of infection (MOI) of 500. A) TEER ratios of the *Lactobacillus* strain HH02. Mean of 3-4 per group. B) TEER ratios of the *Lactobacillus* strain HH04. Mean of 3-4 per group.

TEER Enhancing Ability after One Month of Storage:

The formulated products, which contain either the freeze-dried *Lactobacillus* strains HH02 or HH04 were tested for its TEER enhancing ability after one month of storage at −20° C., 4° C., 25° C. and 40° C. The impact of the formulated products on the integrity of the barrier of the epithelial cell line Caco2 in presence of a formulated product was determined using the TEER EVOM2 assay performed in the same way as described under "Example 5. TEER assay" with following modification. The amount of formulated product, which contains five times more *Lactobacillus* strains than seeded Caco2 cells (multiplicity of infection (MOI) of 500) dissolved in 500 μL of medium on the apical medium Results:

The results showed that the TEER enhancing ability of the formulated products of HH02 and HH04 were stable at the storage temperatures −20° C., 4° C. and 25° C. for at least one month (FIG. 10). A lower TEER activity was seen for the product stored over a month at 40° C.

Impact of the *Lactobacillus* Strains HH02 and HH04 on Epithelial Cell Line Caco2 Barrier Integrity with/without Fructose or Glucose:

The impact of the *Lactobacillus* strains HH02 and HH04 on epithelial cell line Caco2 barrier integrity was determined using the continuous TEER cellZscope assay performed in the same way as described under "Example 5. TEER assay" with following modification. On the apical side, either medium alone, or medium containing 7 mM fructose were added. On the basolateral side, either medium alone, or medium containing 7 mM glucose were added.

Figure 11:
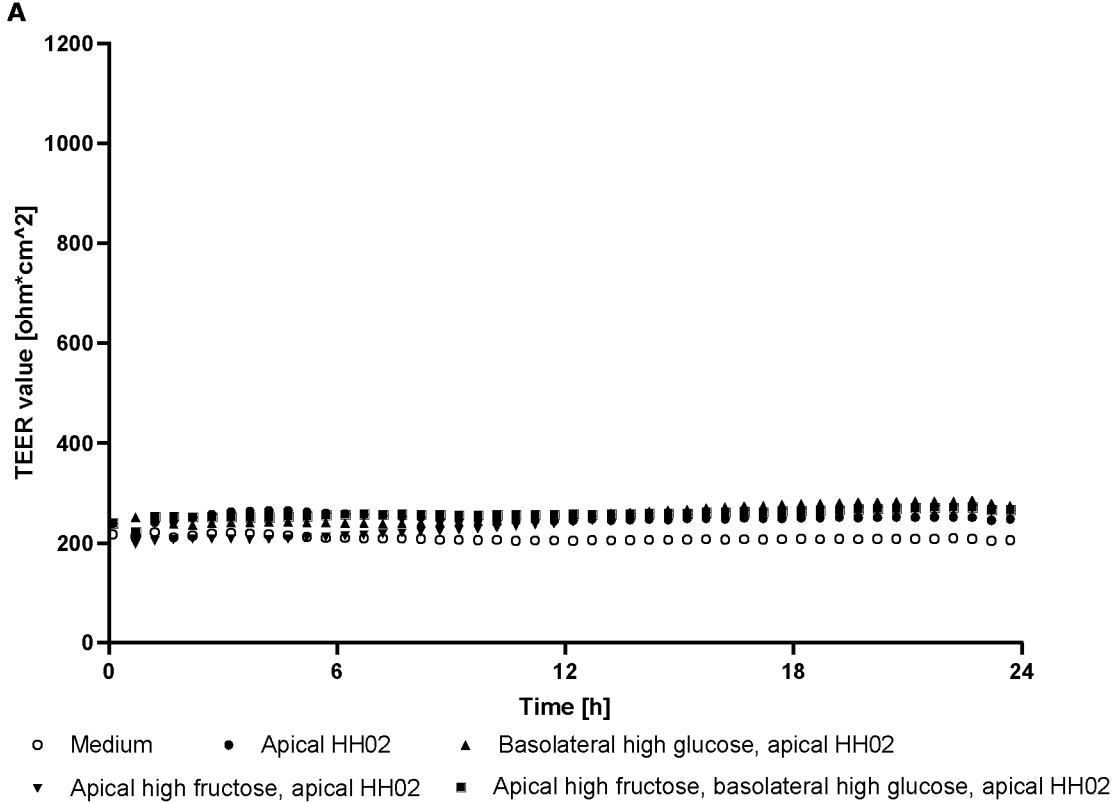
FIG. 11 shows the influence of *Lactobacillus* strains HH02 and HH04 on the transepithelial electrical resistance (TEER) of the epithelial cell line Caco2 at a MOI of 5 in an experimental setting simulating either low (full dot) or high sugar intake (7 mM fructose, reverse full triangle) in the gut, or in situation mimicking systemic high glucose (7 mM glucose, full triangle) on the basolateral side or the combination of both (full square). The medium control is depicted as empty circle. The effect is depicted as continuous TEER value over 24 h incubation time. A) TEER values for the *Lactobacillus* strain HH02. Mean of 1-3 per group. B) TEER values for the *Lactobacillus* strain HH04. Mean of 1-3 per group.
Figure 11:
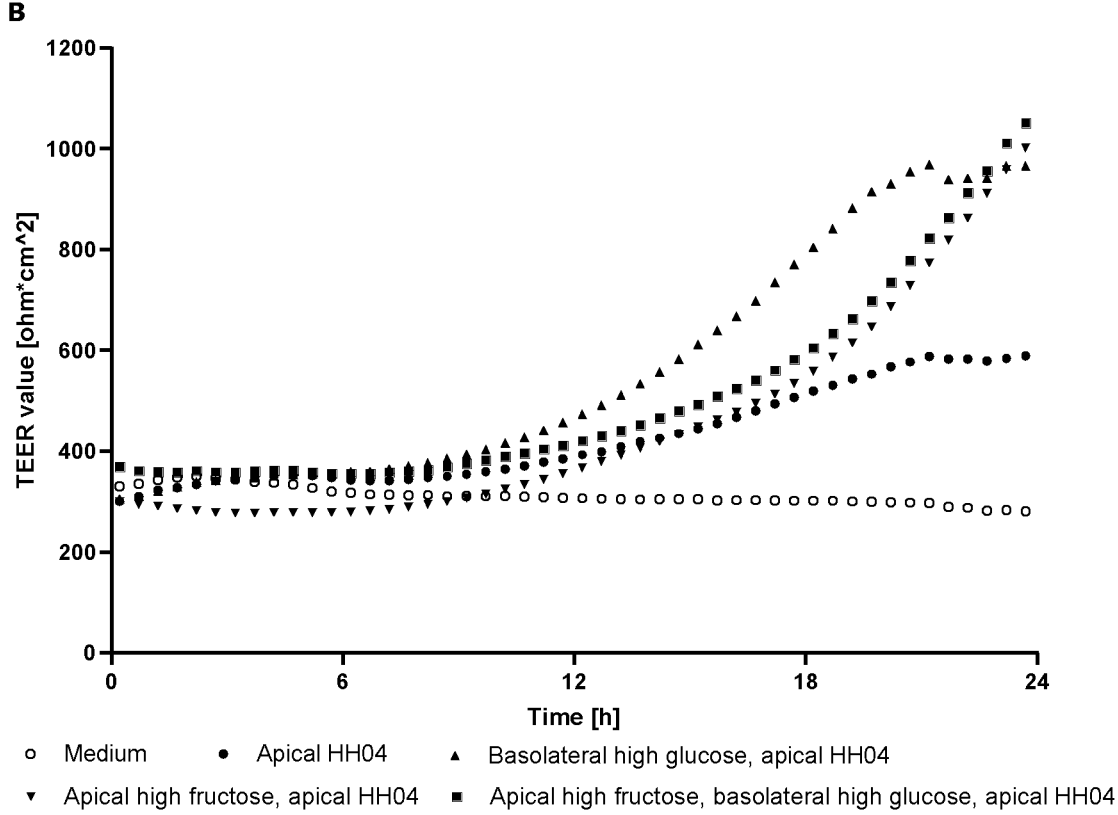

Results:

The results showed that HH02 minimally increase the TEER with little impact by the different concentrations. Presence of high glucose concentration on the basolateral lead to a faster increase in TEER by HH04 compared to conditions where the strain was tested in the presence of standard medium on the basolateral side. This result suggests an enhanced effect from HH04 in subjects suffering from high-blood glucose values compared to the effect in healthy individuals. In presence of high fructose concentration on the apical side, a faster increase in TEER was also observed with HH04 compared to the medium alone. This result suggests an enhanced effect in subjects having high load of fructose in the gut compared to the effect in fasted subjects (FIG. 11).

Example 7. Conversion of Bile Salts

The strains HH01, HH02, HH04 and HH05 were incubated in MRS medium (De Man, Rogosa and Sharpe) for 24 hours at 37 C in the presence of bile salts: Glycocholate, Taurocholate, Glycochenodeoxycholate, Taurochenodeoxycholate, Glycodeoxycholate and Taurodeoxycholate. Bile salts were present in 1.56 mg/mL, 0.56 mg/mL, 1.51 mg/mL, 0.54 mg/mL, 1.51 mg/mL and 0.33 mg/mL, respectively. A reference containing the bile salts in absence of any bacteria was used. After incubation, the supernatant was harvested by centrifugation. Samples were extracted with acetic methanol and analyzed on reverse phase (RP) liquid chromatography mass spectroscopy (LCMS) with high mass resolution. The method was set up to quantify all six above mentioned bile salts. The conversion of conjugated bile salts (CBS) expressed in percent were calculated according to the formula CBS [%]=100 [%]−(A*100 [%]/B). A is the amount of bile salts after 24 h of incubation in presence of bacteria, while B is the amount of bile salts after 24 h of incubation in absence of any bacteria. The higher the CBS value, the more bile salts were converted.

Figure 12:
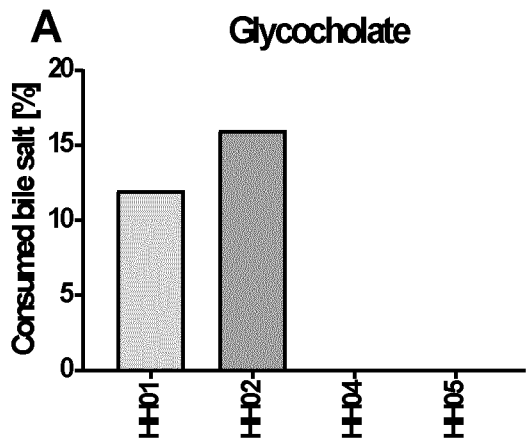
FIG. 12 discloses bar graphs representing the consumed bile salt concentration by lactic acid bacteria (LABs) in simulated bile salt juice. Each column represents one experiment (n=1). For more details see example 7.
Figure 12:
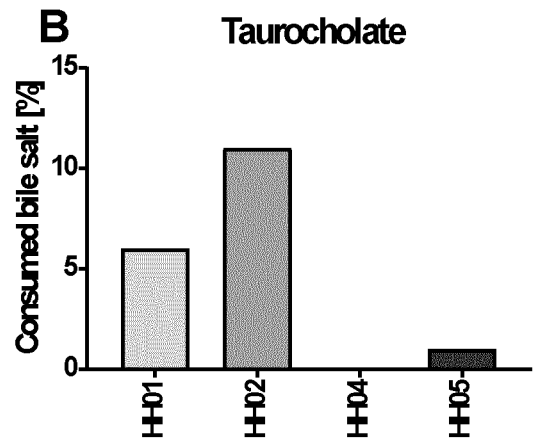
Figure 12:
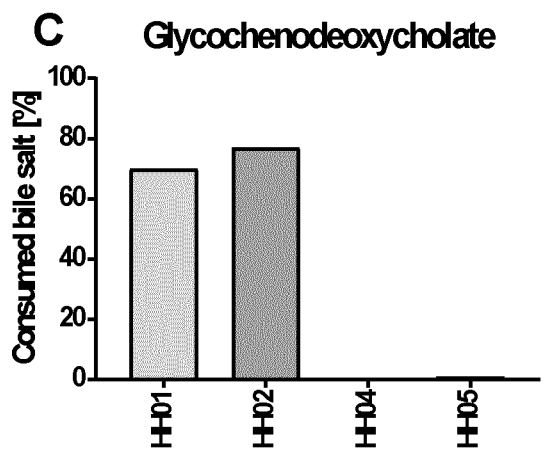
Figure 12:
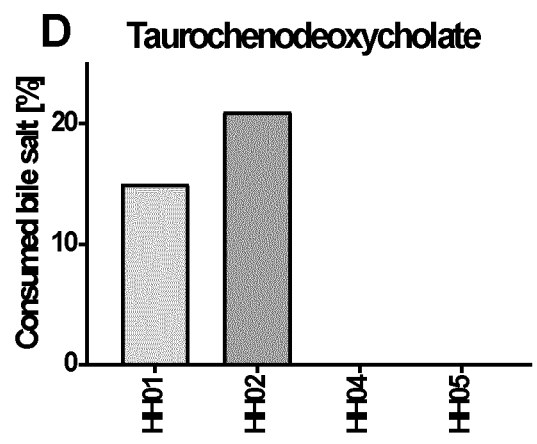
Figure 12:
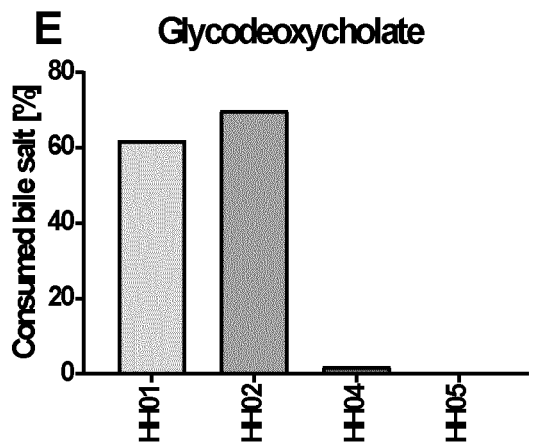
Figure 12:
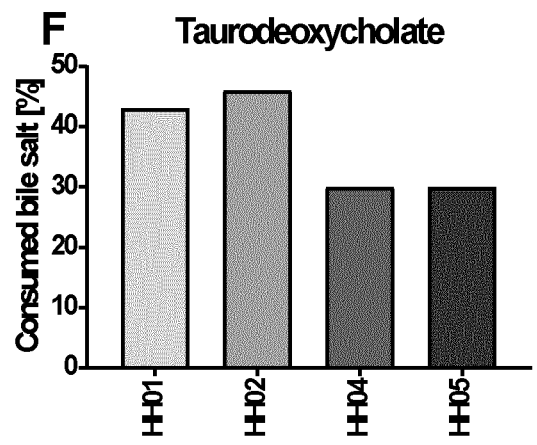

Results are shown in FIG. 12, and show that strains HH01 and HH02 were able to convert partially all bile salts indicating a contribution to decreased fat absorption, while HH04 and HH05 were able to convert partially taurodeoxycholate indicating a positive effect on metabolism.

Example 8. L-Cell Assay for Measuring *Lactobacillus* Stimulated Glucagon-Like Peptide 1 (GLP-1) Release The L-cell assay was performed as described by Gagnon and Brubaker (2015) NCI-H716 Cells. Pp. 221-228 In: Verhoeckx K. et al. (eds) The Impact of Food Bioactives on Health. Springer, Cham. The human L-cell line, NCI-H716 was grown in RPMI-1640 (Roswell Park Memorial Institute) media containing 10% foetal bovine serum and 1% penicillin/streptomycin. The cells (passage between 12-20) were seeded in 24-well plates (200.000 cells/well) and allowed to differentiate for 48 hours. The 24-well plates were precoated with 0.5 g Matrigel/well before cell seeding.

For the glucagon-like peptide 1 (GLP-1) release assay, plates containing the human L-cells were washed twice with Krebs Ringer Buffer containing bovine serum albumin (BSA, 0.2%) before diluted samples of *Lactobacillus* supernatants from HH02 and HH04 or media controls were added for 2 hours in the incubator at 37° C./5% $CO_2$. Phorbol 12-myristate 13-acetate (PMA) (10 μM), and Triton X-100 (0.2%) were included in each test as GLP-1 positive control and for total release of GLP-1, respectively. All test samples contained 25 μM Diprotin A (Sigma-Aldrich), a dipeptidyl peptidase-4 inhibitor. Following incubation all supernatants were removed and stored at −20° C. until analyzed for GLP-1. The cells were analyzed for viability using Presto Blue viability staining (Invitrogen). Supernatants were analyzed for GLP-1 using an active GLP-1 ELISA kit (EGLP-35K, Millipore-Merck). Broths used for the *Lactobacillus* cultivation (Yeast dextrose agar broth (YDA) and for the control bacterial *Staphylococcus epidermidis* ATCC 35984 (S.E) cultivation ((medium 17 with glucose (GM17)) were included as additional controls in the absence of strains.

Figure 13:
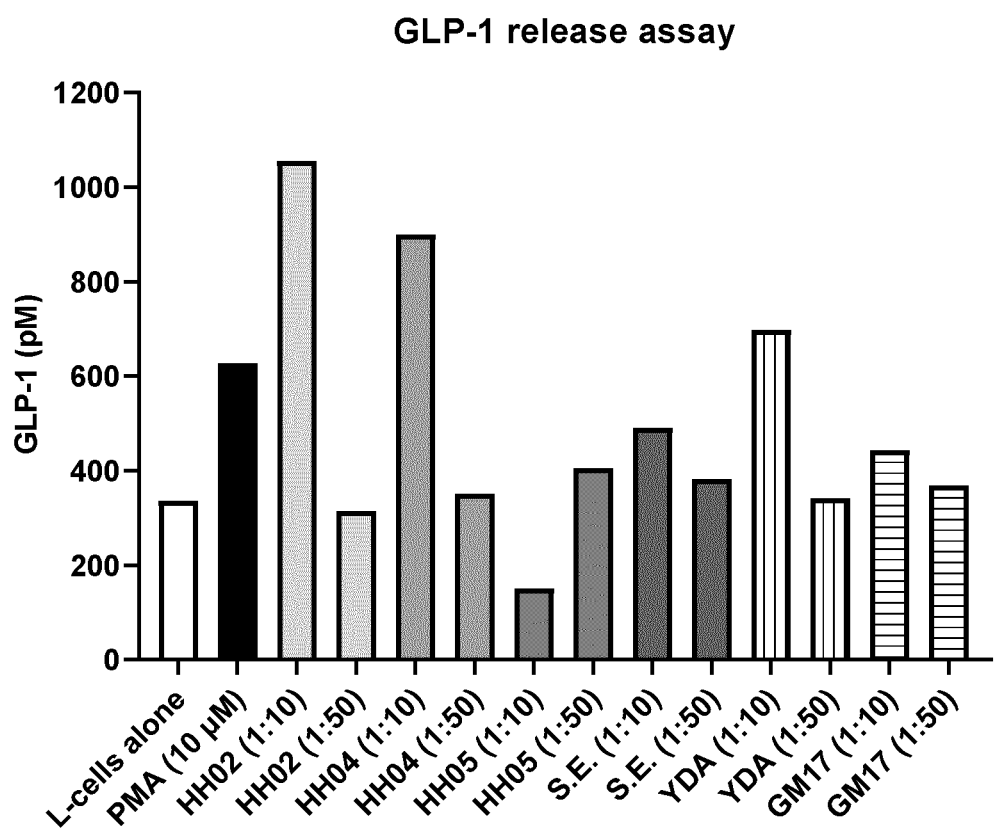
FIG. 13 shows a bar graph representing the mean concentration of Glucagon-like peptide 1 (GLP-1) released by L- cells (NCI-H716) incubated with cell-free growth broth of *Lactobacillus* strains cultivated in YDA medium. Each test sample was diluted 10- and 50 times and added to NCI-H716 cells for 2 hours. Each column represents the mean of 5 individual experiments. For more details, see Example 8.
Figure 14:
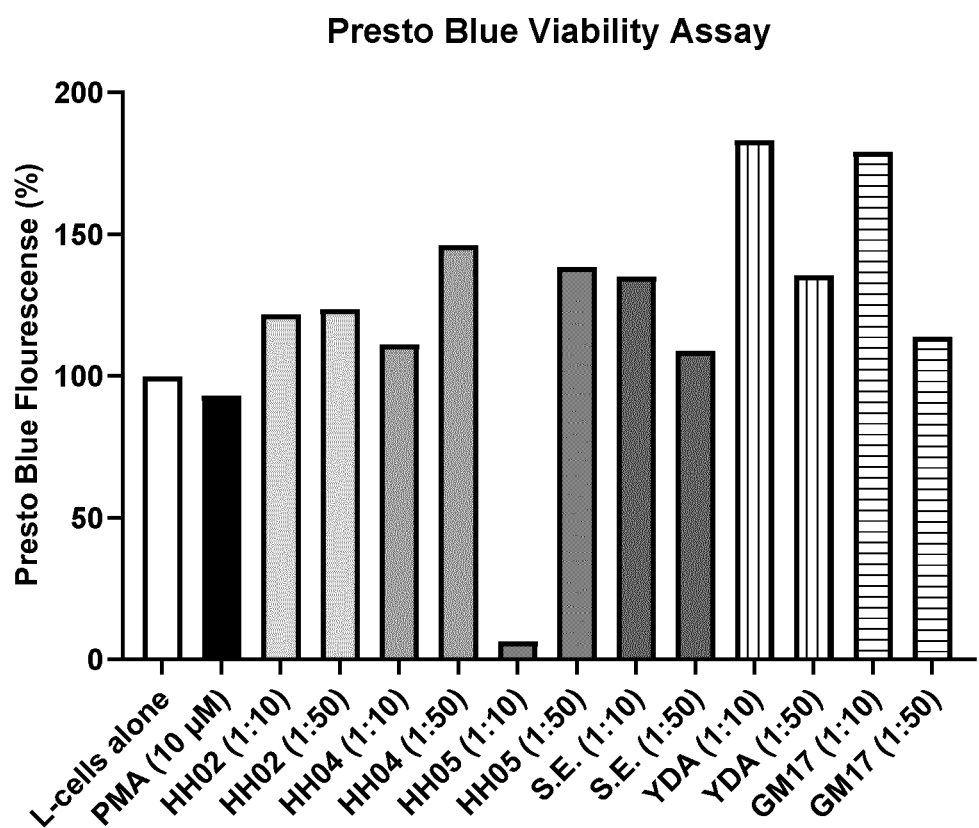
FIG. 14 shows a bar graph representing the NCI-H716 viability (%) after incubation with cell-free culture growth broth (diluted 1:10 and 1:50), fresh culture broth (diluted 1:10 and 1:50) and 10 μM PMA positive control for 2 hours. Cells were added Presto Blue solution and incubated for 25 minutes before Presto Blue florescence was measured at 567 nm (excitation)/587 nm (emission). Each column represents the mean of 5 individual experiments.

Results:

The results showed that cell-free broth from strains HH02 and HH04 if diluted 10 times stimulated the L-cells to release GLP-1. Release of cell-free broth of these strains was higher than YDA medium control diluted 10 times. No release above background level was observed if the cell-free growth broth was tested as 50 times diluted (FIG. 13). Cell-free broth obtained from strain HH02 and HH04 did not affect the viability of NCI-H716 during 2 hours of incubation, demonstrating that GLP-1 release was not due to L-cell burst (FIG. 14).

Example 9. Prophylactic Treatment with *Lactobacillus* in Experimental Colitis Using a Mouse Model In this study, the trinitrobenzene sulfonic acid (TNBS)-induced acute colitis model (Foligne et al, 2007 doi: 10.3748/wjg.v13.i2.236) was used. Colitis was induced in mice by a single intrarectal administration of TNBS whereafter the mice were observed for 2 days. The *Lactobacillus* strains HH01-HH05 described in example 1 were used for this study Study Plan 7 Groups of 15 Balb/c mice were used for the experiment. The mice were transferred to cages on day −19 for acclimatization and had free access to feed and sterile water.

On day −5 to day 1 the mice each received an oral gavage of 100 µL containing vehicle, *Lactobacillus* strains as specified in the scheme below. As vehicle was used PBS pH 7.4 without MgCl$_2$ (Cat. 10010-023, Gibco).

On day 0 the mice in the TNBS respectively the TNBS+ *Lactobacillus* strain groups each received an intrarectal administration of 100 mg/kg 2,4,6-TNBS in ethanol, inducing the colitis.

| Group | Number of mice | *Lactobacillus* straina/vehicle administered day −5 to day 1 | Challenge day 0 |
|---|---|---|---|
| Vehicle control | 15 | Vehicle | Vehicle |
| TNBS | 15 | Vehicle | TNBS |
| TNBS + HH01 | 15 | Vehicle + $10^8$ CFU HH01 | TNBS |
| TNBS + HH02 | 15 | Vehicle + $10^8$ CFU HH02 | TNBS |
| TNBS + HH03 | 15 | Vehicle + $10^8$ CFU HH03 | TNBS |
| TNBS + HH04 | 15 | Vehicle + $10^8$ CFU HH04 | TNBS |
| TNBS + HH05 | 15 | Vehicle + $10^8$ CFU HH05 | TNBS |

The mice were sacrificed on day 2.

Sampling

Figure 15:
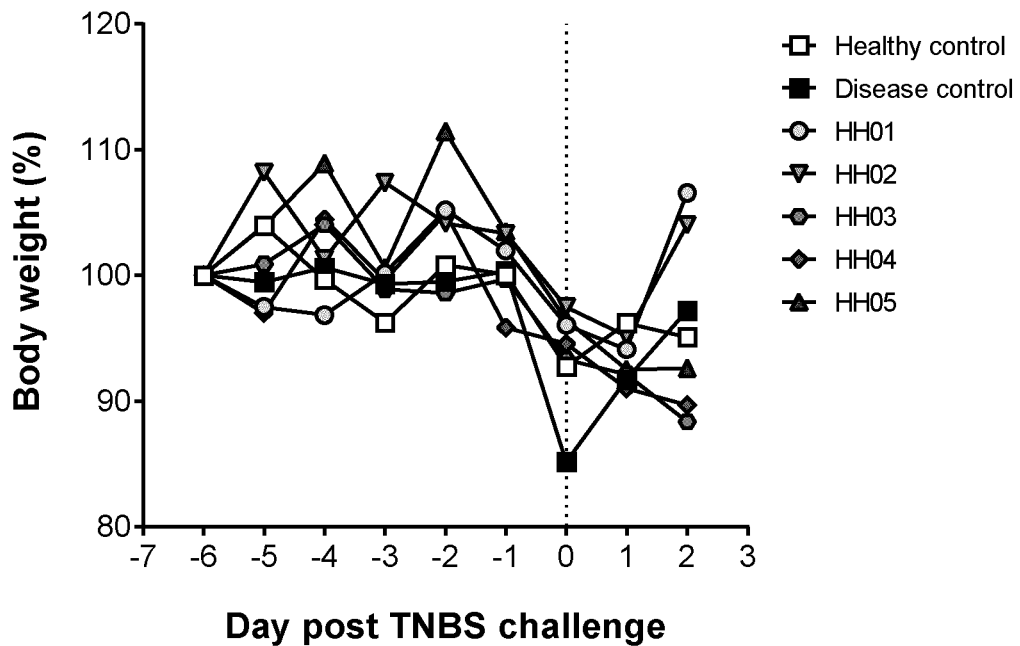
FIG. 15. shows line graph representing the average body weight (% of body weight at day −6) for each group of animals in an acute model of inflammation (colitis) in mice. Each line corresponds to each treatment over the course of the experiment (n=11-15). *Lactobacillus* strain treatment started at day −5. For more details see example 9.

Clinical signs were monitored from day −6 to day 2:

Body weight (see FIG. 15)

Wallace scoring of colon (Foligne et al, 2007 doi: 10.3748/wjg.v13.i2.236).

Figure 16:
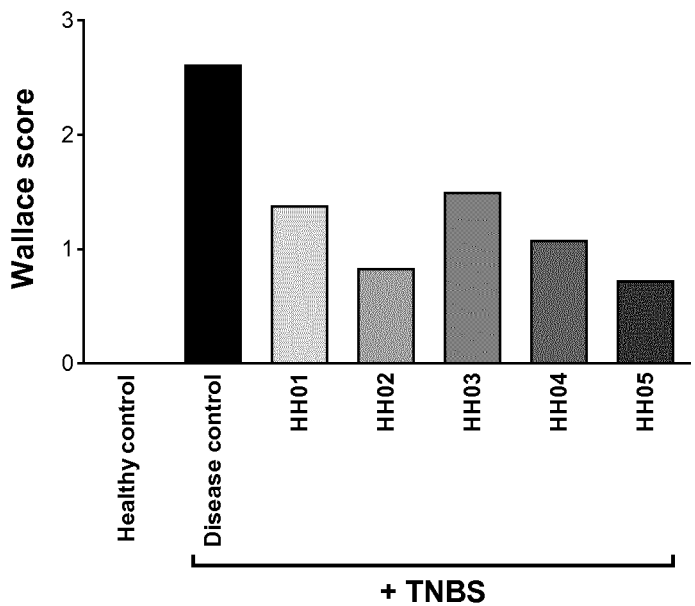
FIG. 16 shows bar graph representing the Wallace score (raw colonic damage score) of each treatment group in an acute model of inflammation (colitis) in mice. Each column represents the mean of n=11-15. The colon was assessed for inflammation and grading was performed macroscopically using a light microscope to evaluate the visual appearance of the colon. This was conducted by 2 blinded observers based on the Wallace scoring method. Criteria for scoring of colonic damage was: 0—no damage; 1—Hyperemia. No ulcers; 2—Hyperemia and thickening of bowel wall. No ulcers; 3—One ulcer without thickening of the bowel wall; 4—Two or more sites of ulceration or inflammation; 5—Two or more major sites of ulceration and inflammation or one site of ulceration/inflammation extending >1 cm along the length of the colon and 6-10—If damage covers >2 cm along the length of the colon, the score was increased by 1 for each additional centimeter. For more details see example 9.

At the end of the study, colon wet weight and colon length were determined (see FIG. 16) and the following samples were collected:

Terminal bleed plasma sample

Rectal sample snap frozen

Figure 17:
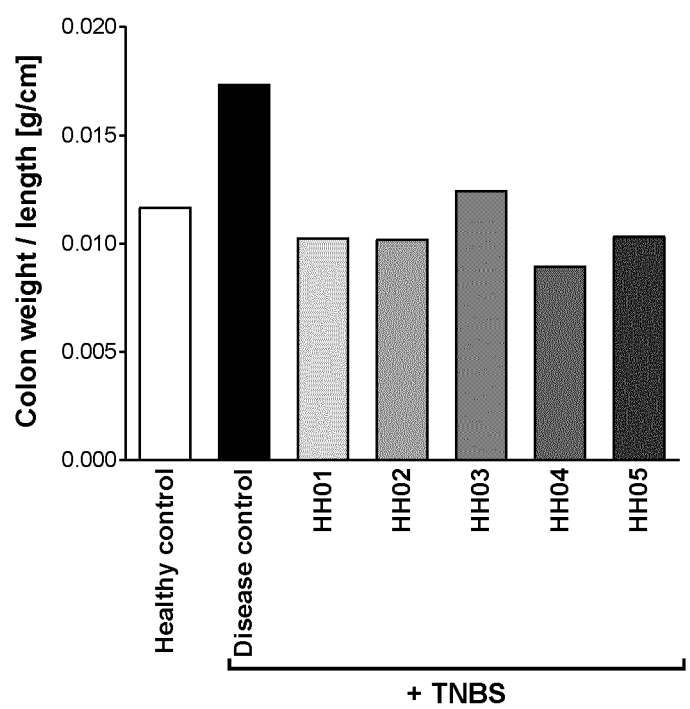
FIG. 17, shows bar graph representing the average colon wet weight (g)/lengths (cm) of each treatment group in an acute model of inflammation (colitis) in mice. Each column represents the mean of n=11-15. For more details see example 9.

Colon samples (see FIG. 17)

Caecum content sample

Spot feces collected on day −6 and 0

Results:

The tested strains showed good anti-inflammatory effect, reflected by the Wallace score.

As expected the vehicle control group did not show any colonic damage, whereas the disease control (TNBS group) had an average damage score of between 2 and 3. The groups that received *Lactobacillus* strain administration of the strains HH01-HH05 showed reduced colonic damage compared to the TNBS (disease control) group, reflected by an average damage score of about 1.

Figure 18:
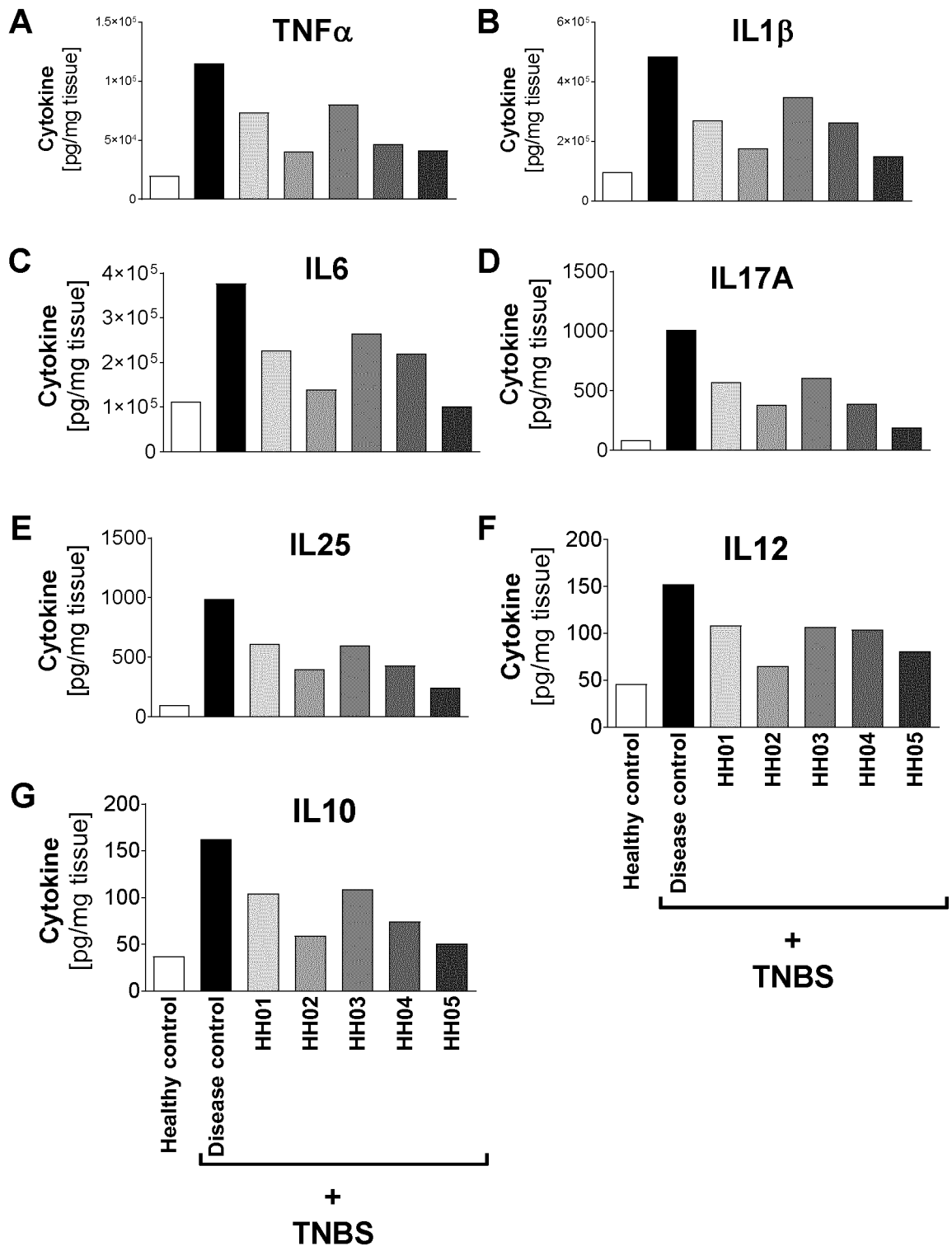
FIG. 18 shows bar graphs representing cytokines in colon tissue in an acute model of inflammation (colitis) in mice. Each column represents the mean of n=11-15. A: TNFα; B: IL1b; C: IL6; D: IL17A, E: IL25, F: IL12 and G: IL10. For more details see example 9.
Figures 19, 20:
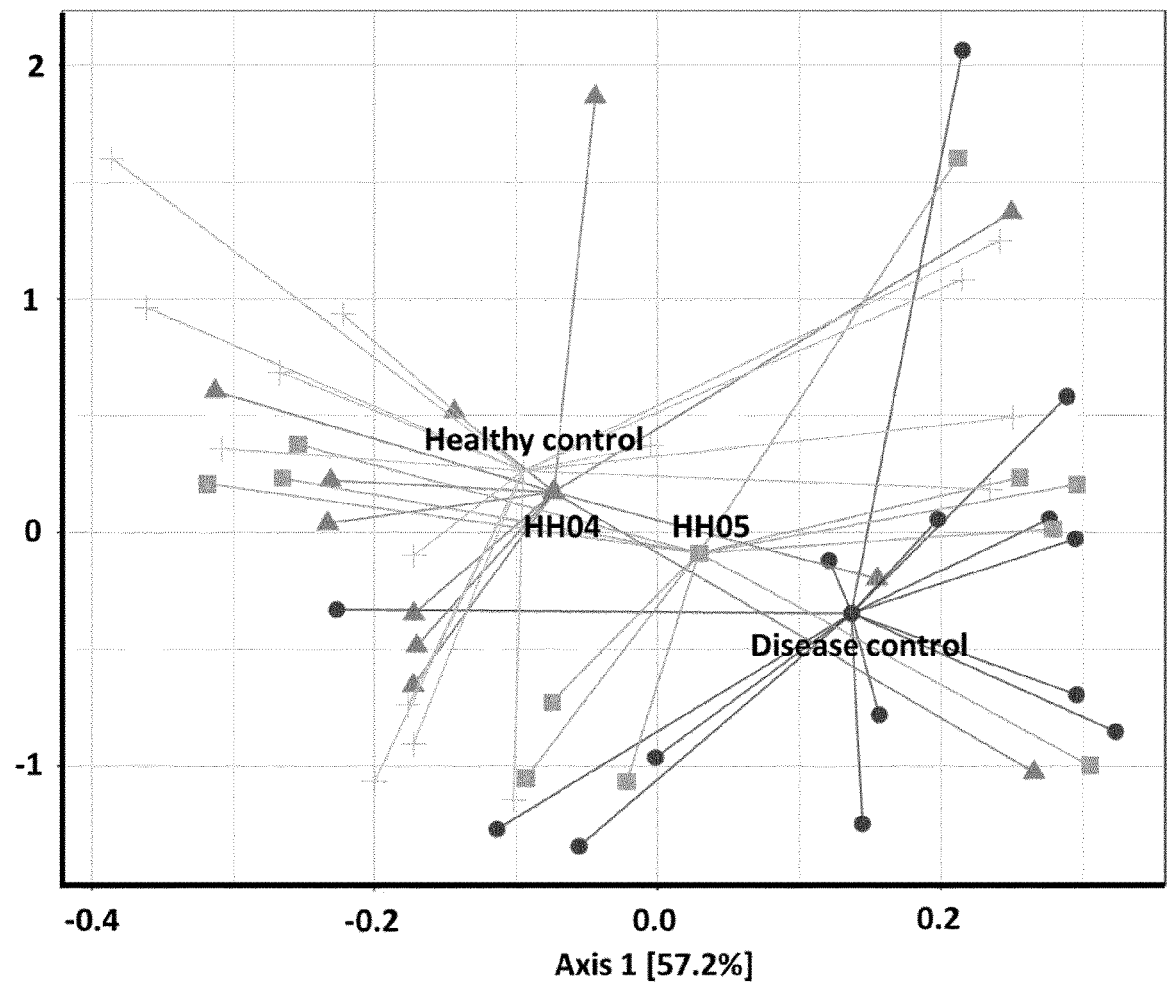
FIG. 19 shows a PCA plot visualizing the effect of treatment on microbial composition (species level)
FIG. 20 shows the percent variance associated with treatment. The analysis was done on genus level.

In addition, the level of the pro-inflammatory cytokines IL12, TNF-α, IL1b, IL25, IL6 and IL17A as well as the regulatory cytokine IL10 were all lower in the *Lactobacillus* strain groups compared to the disease control (see FIG. 18), which corroborated diminished inflammation. Thus, the experiment showed that the *Lactobacillus* strains were capable of reducing colonic inflammation.

Therefore, the overall clinical status was improved by the *Lactobacillus* strains HH01-HH05.

Example 10. Impact of *Lactobacillus* Strain Strains in a Diet-Induced Mouse Model Fed a Classical High Fat Diet The study aimed to demonstrate improved metabolic health, such as alleviating prediabetes, by two *Lactobacillus* strain test stains (HH04 and HH05) in a diet-induced obesity (DIO) mouse model. The study had a prophylactic approach for DIO with administration of the strains by daily oral gavage for 12 weeks simultaneously to receiving a high fat diet (HFD) (for study overview refer to FIG. 21.

Study Overview:

C57BL/6J mice (Jackson Lab. Bar Harbour, Me. USA) were enrolled in 4 batches of 12 mice (3 mice per group) with treatment starting weekly (for 4 weeks). All mice were 8 weeks of age at the start of the experiment (week 0). The mice were transferred to cages 2 weeks before the experiment started for acclimatization. In the acclimatization period the mice had free access to low fat diet (LFD) and water.

The experiment started at week 0, where the mice were transferred to the experimental diet, and received a daily oral gavage of a total volume of 100 µL according to the scheme below. The *Lactobacillus* strains used in this example were strain HH04 and strain HH05 described in ex *Lactobacillus* ample 1.

| Group number | Number of mice | Diet | Daily oral gavage |
|---|---|---|---|
| A | 12 | LFD | Vehicle (PBS, Gibco) |
| B | 12 | HFD | Vehicle (PBS, Gibco) |
| C | 12 | HFD | HH04-$10^8$ CFU |
| D | 12 | HFD | HH05-$10^8$ CFU |

High fat/sucrose diet (HFD) containing 45% of the energy from fat (87% lard, 13% soy bean oil), 35% from carbohydrates (mainly sucrose and maltodextrin), 20% of protein (casein) (D12451, Research Diet Inc., NJ, USA)

Low fat reference diet (D12450H, Research Diet Inc. NJ, USA) containing 10% of energy from fat. Both diets contained 17% of the gross mass from sucrose.

Sampling and Measurements

Body composition of individual mice was assessed by the average of three measures of magnetic resonance (MR) scans (Bruker, calibrated daily when in use) in week 0, 4, 8, and 12 of the experimental protocol.

Fresh feces were collected at the same time as MR scans in the beginning of the light cycle (9 AM±1 hour) prior to daily gavage. The samples were immediately frozen on dry ice and stored at −80° C. until further processing.

Body weight was measured weekly at 8-9 AM.

Figure 22:
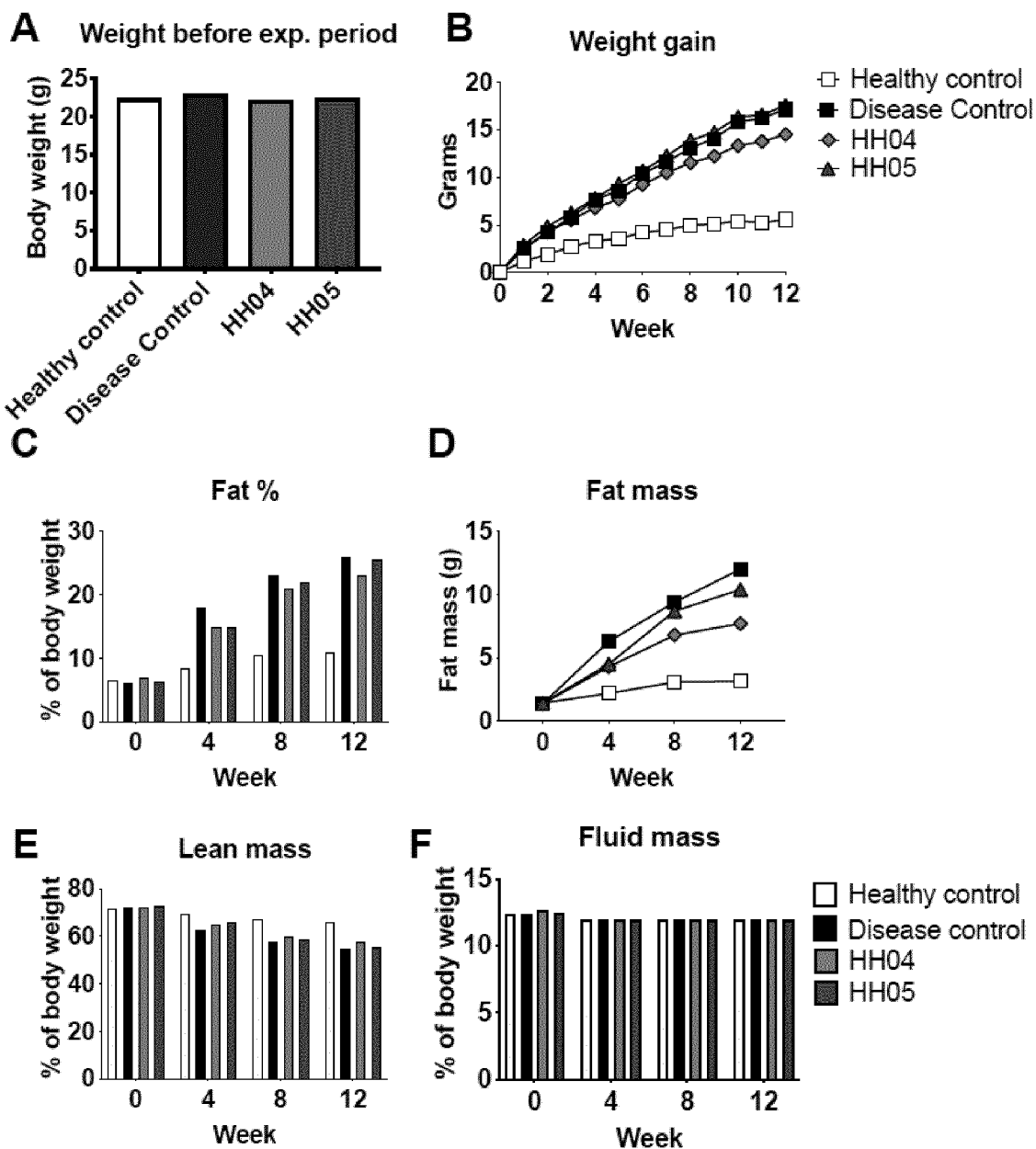
FIG. 22 shows the effect of HH04 and HH05 on weight development and body composition in a diet-induced obesity mouse (DIO) model. Mean of 10-12 mice per group are shown A) Weight after randomization. B) Weight development in experimental groups post initiation of experimental diets and gavage treatment. C) Fat mass as % of total body weight obtained from Magnetic Resonance scans at the depicted time points. D) As in C but depicted as group Mean with connecting lines. E) Lean mass as % of total body weight obtained from Magnetic Resonance scans at the depicted time points. F) Fluid mass as % of total body weight obtained from Magnetic Resonance scans at the depicted time points. More details can be found in example 10.

The weight development and body composition are shown in FIG. 22. Mean of 10-12 mice per group are shown A) Weight after randomization. B) Weight development in individual groups post initiation of experimental diets and gavage treatment. C) Fat mass as % of total body weight obtained from Magnetic Resonance scans at the depicted time points. D) Fat mass in grams depicted as group Mean with connecting lines. E) Lean mass as % of total body weight obtained from Magnetic Resonance scans at the depicted time points. F) Fluid mass as % of total body weight obtained from Magnetic Resonance scans at the depicted time points.

Mice were transferred to new, clean cages with enrichment but no nesting material at (9 AM±1 hour). Feed was measured at the time of transfer and again after 24 h, where the mice were retransferred to clean standard cages (including nesting material). 24 h feces were carefully collected from the bedding and stored at −80° C. until further processing.

Glucose Tolerance Test, Glucose-Stimulated Insulin Secretion and Gut Permeability Test An oral glucose tolerance test was performed in week 10 of the experimental protocol. Mice were fasted at 8 AM for 5 h and gavaged at 10 AM. 5 h fasted blood glucose measurement (OneTouch Vario Flex, LifeScan) and sampling of the blood from the tail vein were executed prior to oral gavage with 4 µL/g lean mass of 50% dextrose solution and 150 µL sulfonic acid solution. Sulfonic acid solution consisted of 1.5 mg fluorescein-5 (6)-sulfonic acid (Invitrogen) dissolved in 150 µL suspension of 0.5% Carboxymethylcellulose Sodium Salt (CMC) (Sigma) in distilled water. Blood glucose was measured from tail vein puncture at time points 0, 15, 30, 60, 90, and 120 min after dextrose challenge and blood samples for insulin and gut permeability were taken in ethylenediaminetetraacetic acid (EDTA) prepared capillary tubes (Sarstedt) at time points 0, 15, 30, 60, and 120 min post challenge.

Mice received 0.5 mL saline (Hospira) after the procedure allowing the mice to rehydrate. Blood samples were centrifuged for 10 min at 1000 rcf at 4° C. For insulin measurements, the first 5 µL of plasma was transferred to 96-well PCR plates on dry ice and kept at −80° C. until downstream processing. The next 5 µL of plasma, used for gut permeability test, was transferred to black 96-well optical-button plates (Nunc) and kept on wet ice until addition of 150 µL of 0.5% CMC in distilled water and thoroughly mixed. The plate was read on Synergy HT Microplate reader (BioTek) at excitation/emission 485/528 nm wavelength.

Insulin levels were measured by Mouse ultrasensitive Insulin ELISA (Alpco) following the manufacturer's protocol and quantified on EnSpire 2300 multilabel reader (PerkinElmer).

Figure 23:
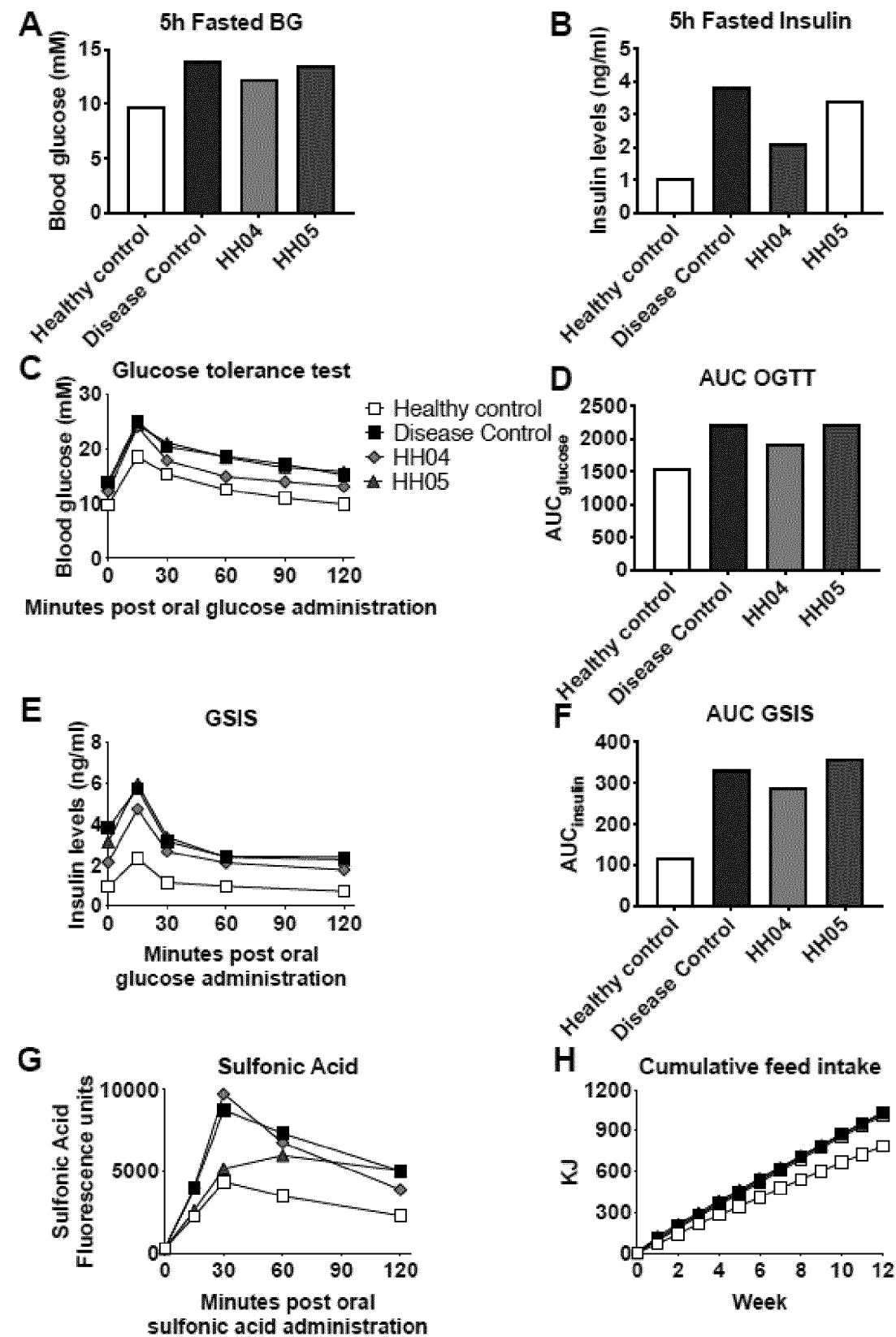
FIG. 23 shows the effect of *Lactobacillus* strains on glucose regulation and gut permeability. A) 5 h fasted Blood Glucose after 10 weeks of HFD feeding and daily gavage treatments. Bars Mean of 10-12 mice per group. B) 5 h fasted insulin after 10 weeks of HFD feeding and daily gavage treatments. Bars Mean of 10-12 mice per group. C, E) Oral Glucose tolerance test in 5 h fasted mice after 10 weeks of HFD feeding and daily gavage treatments. C depicts blood glucose levels during the challenge (2 μg per g lean mass) and E depicts plasma levels of the endogenous insulin response to the glucose challenge. Mean of 10-12 mice per group. D) Area under the curve for OGTT week 10. Bars Mean of 10-12 mice per group. F) Area under the curve for GSIS week 10. Bars Mean of 10-12 mice per group. G) Plasma sulfonic acid fluorescence units post oral challenge (150 μl per mouse, conc: 10 mg/mL) in 5 h fasted mice after 10 weeks of HFD feeding and daily gavage treatments. Mean of 10-12 mice per group. H) Cumulative feed intake per mouse during 12 weeks of HFD feeding and daily gavage treatments. Due to co-housing the intake is in average per mouse per cage with n=4 in each group. Bars Mean. A-G) All mice were gavaged with their respective treatment 3 hours before the oral challenge. More details about the study can be found in example 10.

The effect of *Lactobacillus* strains on glucose regulation and gut permeability is shown in FIG. 23: A) 5 h fasted Blood Glucose after 10 weeks of HFD feeding and daily gavage treatments. Bars Mean of 10-12 mice per group. B) 5 h fasted insulin levels after 10 weeks of HFD feeding and daily gavage treatments. Bars Mean of 10-12 mice per group. C, E) Oral Glucose tolerance test in 5 h fasted mice after 10 weeks of HFD feeding and daily gavage treatments. C depicts blood glucose levels during the challenge (2 µg per g lean mass) and E depicts plasma levels of the endogenous insulin response to the glucose challenge. Mean of 10-12 mice per group. D) Area under the curve for OGTT week 10. Bars Mean of 10-12 mice per group. F) Area under the curve for GSIS week 10. Bars Mean of 10-12 mice per group. G) Plasma sulfonic acid fluorescence units post oral challenge (150 µL per mouse, conc: 10 mg/mL) in 5 h fasted mice after 10 weeks of HFD feeding and daily gavage treatments. Mean of 10-12 mice per group. H) Cumulative feed intake per mouse during 12 weeks of HFD feeding and daily gavage treatments. Due to co-housing the intake is in average per mouse per cage with n=4 in each group. Bars Mean. A-G) All mice were gavaged with their respective treatment 3 hours before the oral challenge.

Necroscopy

Necropsy was carried out in week 12 of the experimental protocol. Mice were fasted from 7 AM and gavaged at 10 AM. Euthanasia was done in alternating order taking one mouse per cage. Euthanasia of Batch 1 started with group B, then C etc. Batch 2 started with group C and so forth for the remaining batches starting with group D and A, respectively. Mice were anesthetized with isoflurane (Fresenius Kabi). Cardiac puncture was done using a 25 G needle and 1 mL syringe coated with EDTA (Sigma-Aldrich). Blood was transferred to Eppendorf tubes containing 1 µL of dipeptidyl peptidase-IV (DPP-IV) inhibitor (Millipore) and 1 µL of a protease inhibitor cocktail (Sigma). The samples were centrifuged at 1000 rcf for 10 min and plasma were aliquoted in triplicates, placed on dry ice and transferred to −80° C. storage until further processing.

Tissue Harvesting

The weight of the liver, pancreas, epididymal white adipose tissue (eWAT), inguinal white adipose tissue (iWAT), retroperitoneal white adipose tissue (rpWAT), mesenchymal white adipose tissue (mWAT) heart, quadriceps, gastrocnemius, brain and colon were measured and the tissues immediately frozen in liquid nitrogen and stored at −80° C. Tissues were dissected by the same operator and taken in the same order for all mice. The brain was frozen in liquid nitrogen <60 sec. post mortem.

Figure 24:
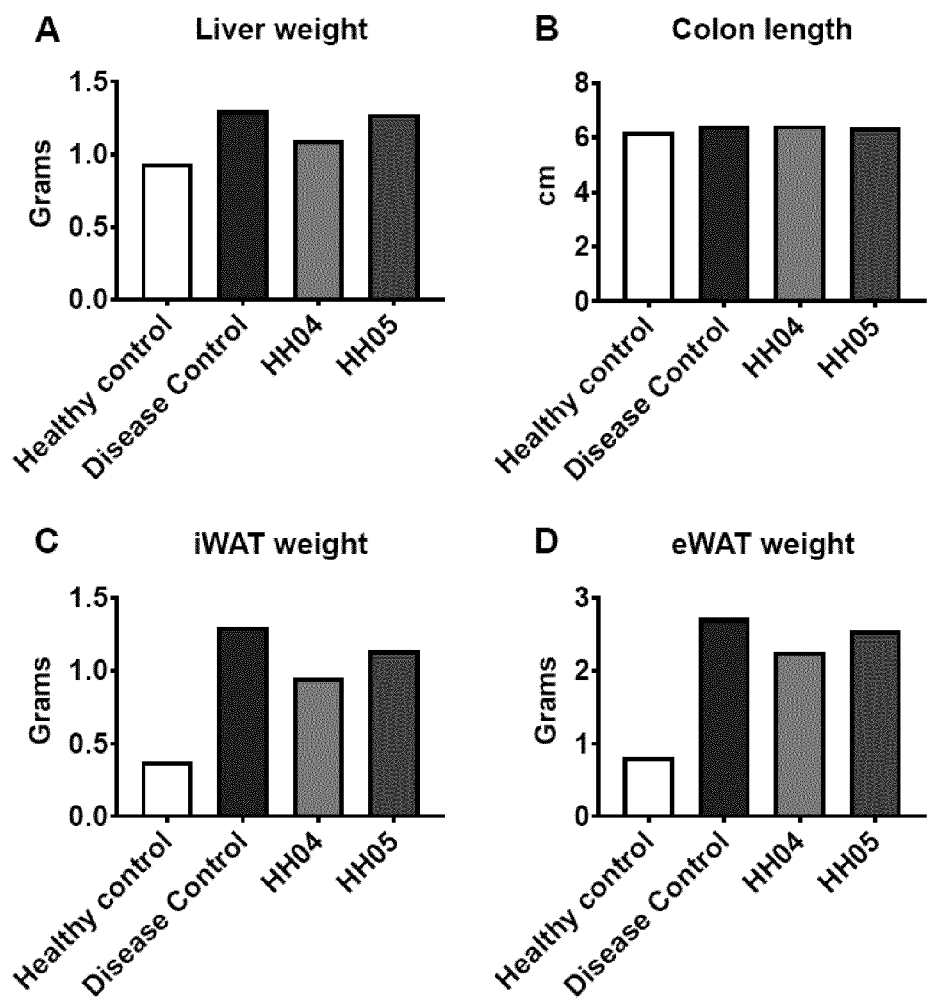
FIG. 24 shows the effect of *Lactobacillus* strains on tissue weights or lengths in a diet-induced obesity mouse model. Bars represent mean value of 10-12 mice pr. group A) Weight of the liver at necropsy after 12 weeks of daily gavage. B) Length of the colon at necropsy after 12 weeks of daily gavage. Bars show mean of 10-12 mice per group. C) Weight of inguinal white adipose tissue (iWAT) at necropsy after 12 weeks of daily gavage. D) Weight of epididymal white adipose tissue (eWAT) at necropsy after 12 weeks of daily gavage. More details about the study can be found in example 10.
Figure 25:
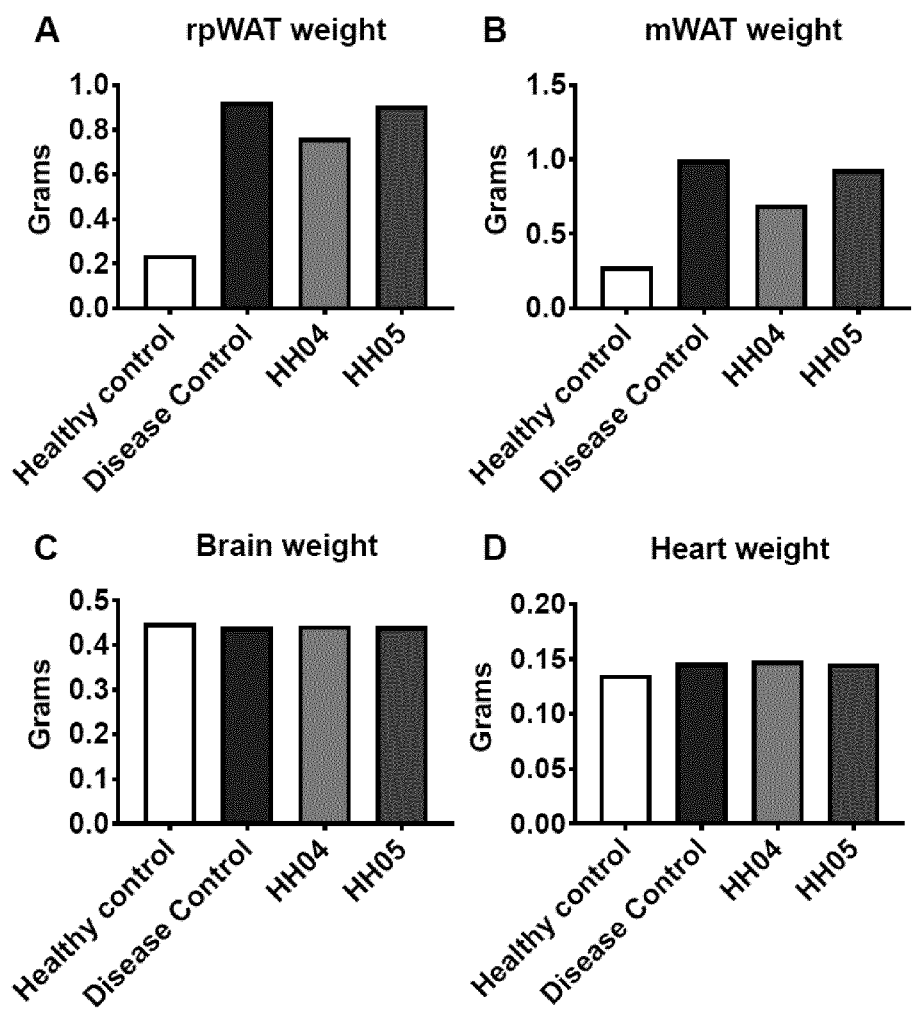
FIG. 25 shows the effect of *Lactobacillus* strains on tissue weights in a diet-induced obesity mouse model. Bars represents mean of 10-12 mice pr. group at necropsy after 12 weeks of daily gavage. A) Weight of retroperitoneal white adipose tissue (rpWAT). B) Weight of mesenchymal white adipose tissue (mWAT). C) Weight of the brain. D) Weight of the heart. More details about the study can be found in example 10.

The effect of *Lactobacillus* strains on tissue weights are shows in FIG. 24, wherein Bars represent mean value of 10-12 mice pr. group A) Weight of the liver at necropsy after 12 weeks of daily gavage. B) Length of the colon at necropsy after 12 weeks of daily gavage. Bars show mean of 10-12 mice per group. C) Weight of iWAT at necropsy after 12 weeks of daily gavage. D) Weight of eWAT at necropsy after 12 weeks of daily gavage; and in FIG. 25, wherein Bars represents mean of 10-12 mice pr. group at necropsy after 12 weeks of daily gavage. A) Weight of rpWAT. B) Weight of mWAT. C) Weight of the brain. D) Weight of the heart.

The length of the small intestine (from stomach to cecum) and colon (from cecum to rectum) were measured and kept on Plexiglas plate cooled by underlying wet ice throughout the handling time. Duodenum was considered the first 5 cm of the small intestine and the remaining small intestine tissue was divided in 3 parts of equal length. The first 3 cm were discarded, and the remaining of the proximal ⅔ of the small intestine was categorized as jejunum. The first 3 cm of the distal ⅓ of the small intestine was discarded and the remaining tissue categorized as ileum. The most proximal cm of duodenum, jejunum, ileum and colon was saved for histology in Carnoy's solution (to preserve mucous layer integrity) prior to emptying the intestinal tissues.

Content of the small intestine, cecum, and colon were isolated by mechanical pressure, frozen on dry ice and subsequently stored at −80° C. Tissue from duodenum, jejunum, ileum, colon, and cecum were snap frozen in liquid nitrogen and stored at −80° C. In Batch 1, tissues for histology from liver, pancreas, eWAT, iWAT, rpWAT, mWAT, heart, quadriceps, and gastrocnemius were preserved in a 4% paraformaldehyde solution for 72 hours followed by preservation in 70% ethanol. In Batch 2-4 tissues for histology from liver, eWAT, iWAT, and mWAT were preserved in a 4% paraformaldehyde solution for 72 hours followed by preservation in 70% ethanol. For all Batches, liver tissue was additionally preserved in O.C.T Compound (Sakura Finetek) to enable histological Oil Red 0 lipid staining.

Plasma Biochemical Analysis

Figure 26:
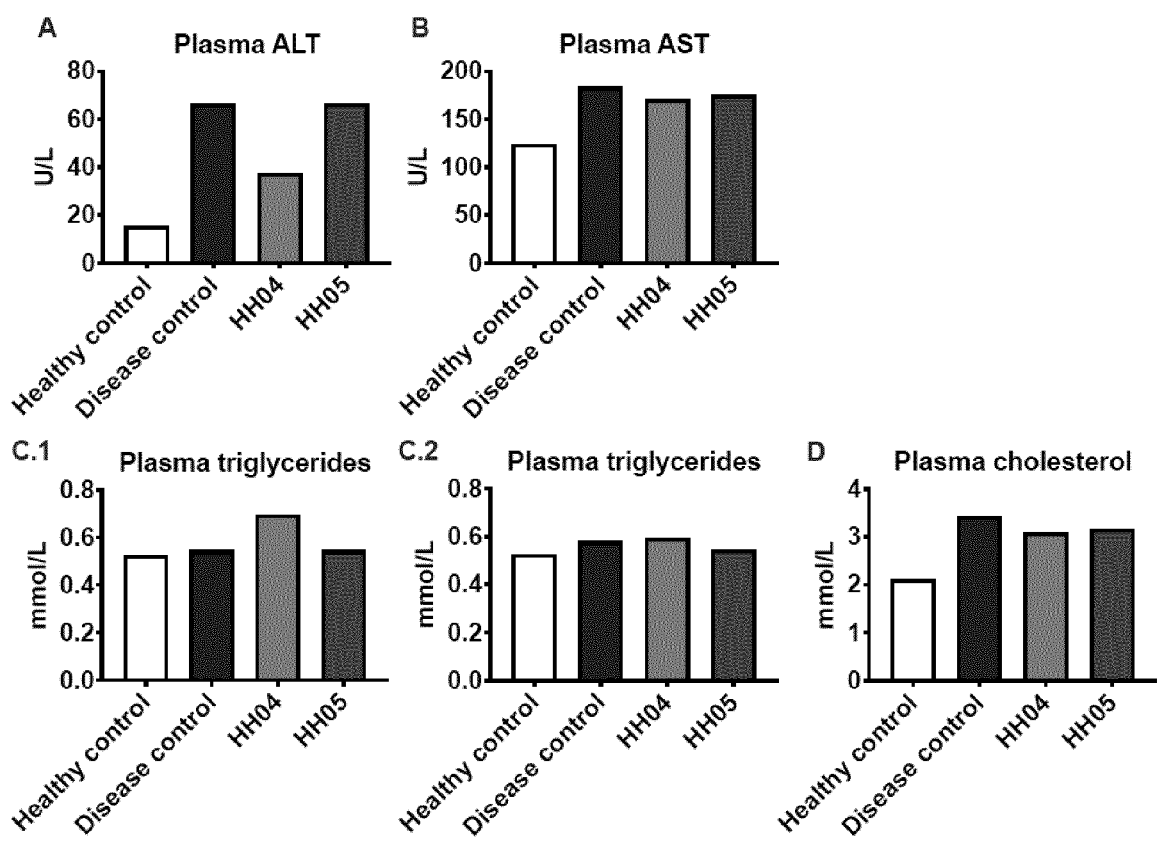
FIG. 26 shows the biochemical analysis of *Lactobacillus* strain effect on plasma markers in a diet-induced obesity mouse model. A) Alanine Aminotransferase. B) Aspartate Aminotransferase. C.1) Triglycerides with all animals included. C.2) Triglycerides where two animals have been excluded after evaluated outside the detection limits of the specific assay. D) Total cholesterol. Each bar represents mean of 10-12 mice per group. More details about the study can be found in example 10.

The effect of *Lactobacillus* strains on plasma biomarkers of liver damage and lipid levels are shown in FIG. 26 wherein bars represent mean value of 10-12 mice pr. group A) Alanine Aminotransferase (ALT), B) Aspartate Aminotransferase (AST), C.1) Triglycerides including all data points, C.2) As C.1, but with two datapoints excluded after evaluation of the detection limit of the used assay. D) Total cholesterol. These analyses were carried out by the medical biochemistry department at Université Laval, Heart and Lung Institute under locally developed procedures meeting the highest criteria for handling and analysis of human and animal samples.

Figure 27:
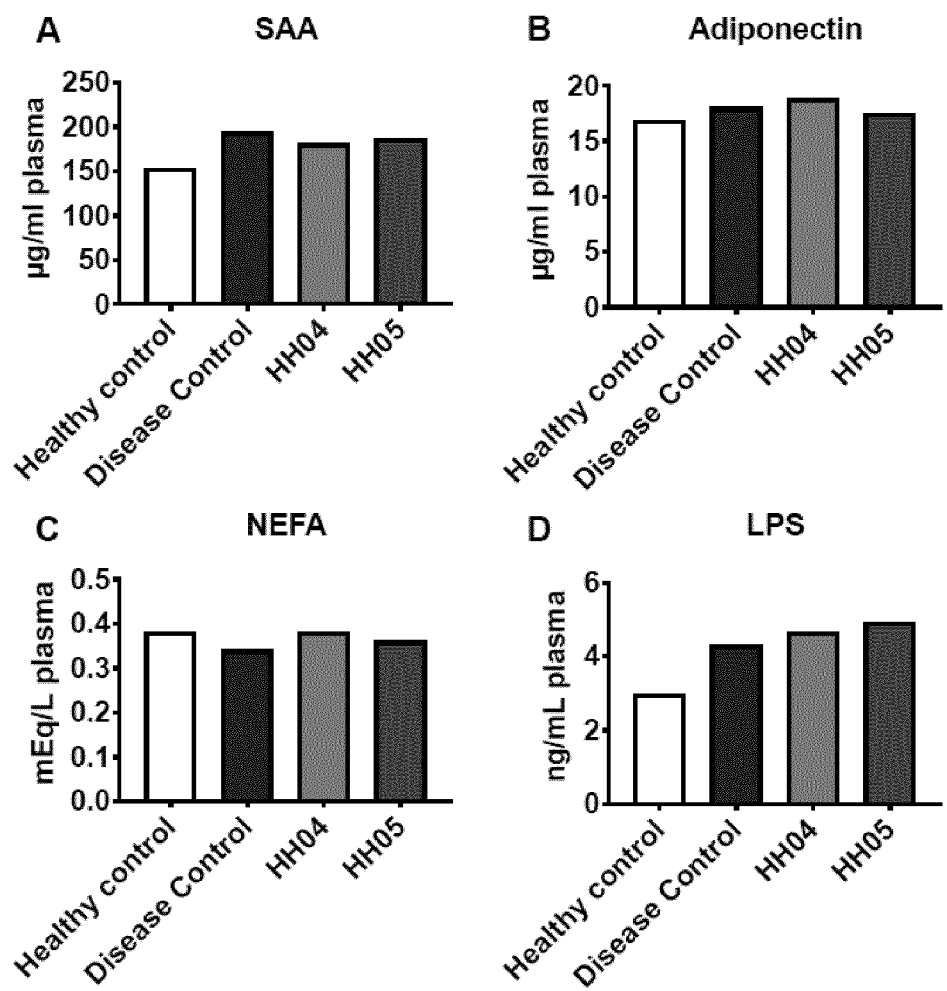
FIG. 27 shows results of *Lactobacillus* strain effect on plasma markers in a diet-induced obesity mouse model. A) Serum Amyloid A. B) Adiponectin. C) Non-esterified fatty acids. D) Lipopolysaccharide. A-E) Each bar represents mean of 10-12 mice per group. More details about the study can be found in example 10.

The effect of *Lactobacillus* strains on other plasma markers are shown in FIG. 27 wherein bars represent mean value of 10-12 mice pr. group A) Serum amyloid A (SAA), B) Adiponectin, C) Non-esterified fatty acids (NEFAs), D) LPS was carried following the ELISA kit manufacturer's protocol.

Liver Lipid Accumulation

Figure 28:
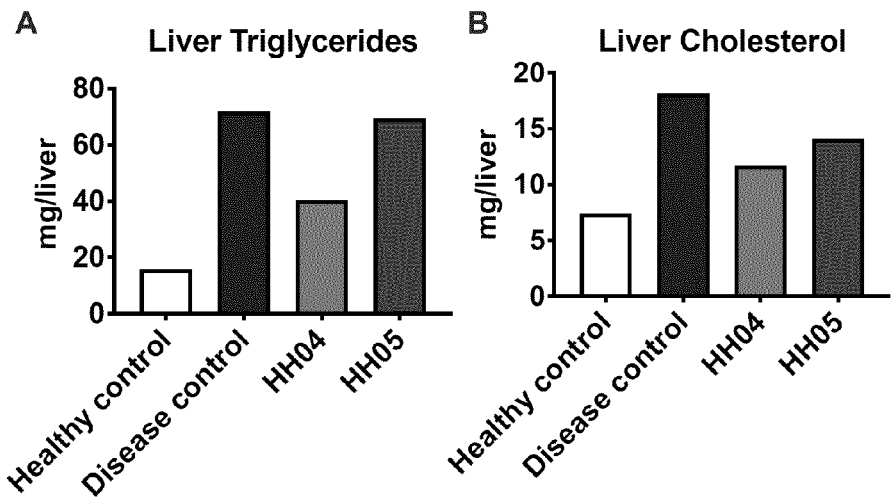
FIG. 28 shows results of *Lactobacillus* strain effect on liver lipid accumulation in a diet-induced obesity mouse model. A) Triglyceride content in liver tissue as mg per liver and B) Cholesterol in liver tissue as mg per liver. Each bar represents mean value of 10-12 mice per group. More details about the study can be found in example 10.

The liver of each mouse was homogenized in liquid nitrogen by cryo-grinding the tissue with mortar and pestle while kept frozen and transferred to new tubes. Lipids were extracted from 50 mg of the powdered tissue. The effect of *Lactobacillus* strains on hepatic lipid accumulation were measured by calorimetric assays and are shown in FIG. 28 wherein bars represent mean value of 10-12 mice per group A) Triglyceride and B) Cholesterol.

Intestinal Cytokine Quantification

Figure 29:
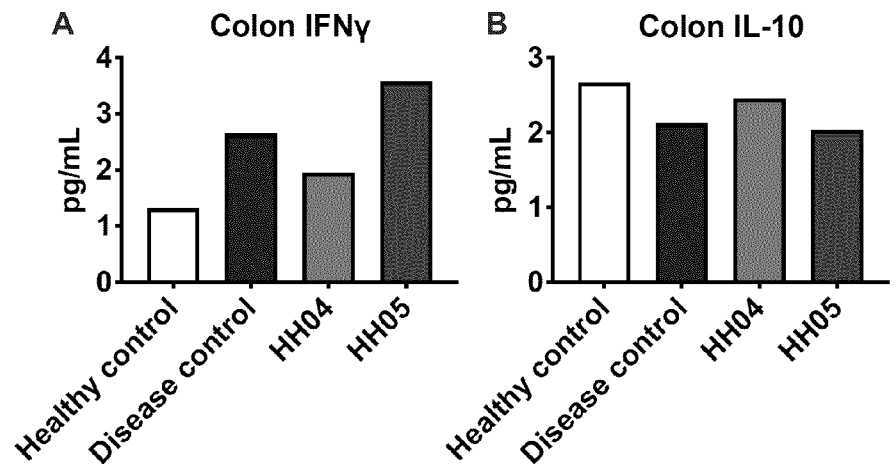
FIG. 29 shows results of *Lactobacillus* strain effect on colon cytokines in a diet-induced obesity mouse model. A) Cytokine Interferon γ (IFNγ) levels in colon tissue and B) Cytokine Interleukin-10 (IL-10) levels in colon tissue. Each bar represents mean value of 10-12 mice per group. More details can be found in example 10.

Cytokine levels were measured in homogenized colon tissue using the Bio-Plex 200 Luminex system following the manufacturer's instructions. The effect of *Lactobacillus* strains on cytokine levels in the colon are shown in FIG. 29 of A) Interferon-gamma (IFNγ) and B) IL-10 wherein bars represent mean value of 10-12 mice per group.

Gut Microbiota Analysis

Bacterial DNA was extracted from the frozen fecal samples and the hypervariable V3-V4 16S rRNA region was amplified and sequenced using the Illumina MiSeq platform.

The sequence data was pre-processed, tag identified and trimmed, paired-end reads were merged, truncated at a quality score of 4, and requiring at least 100 bp overlap with a merged read length between 300 and 600 bp in length. Sequences were strictly dereplicated, discarding clusters with less than 5 sequences. Sequences were clustered at 97% sequence similarity, using the most abundant strictly dereplicated reads as centroids and discarding suspected chimeras based on internal comparison. Taxonomic assignment of OTUs is done using the database from Ribosomal Database Project.

Quantitative PCR with primers specific to the HH04 or HH05 strains were used to quantify the amount of probiotic DNA present in samples from intestinal content. The relative amounts in arbitrary units are shown in FIG. 30 wherein bars indicate mean of 10-12 samples per group where A) HH04 amounts in fecal samples from the indicated groups, B) HH04 amounts in small intestine content, C) HH05 in fecal samples, and D) HH05 in small intestine samples.

Figure 30:
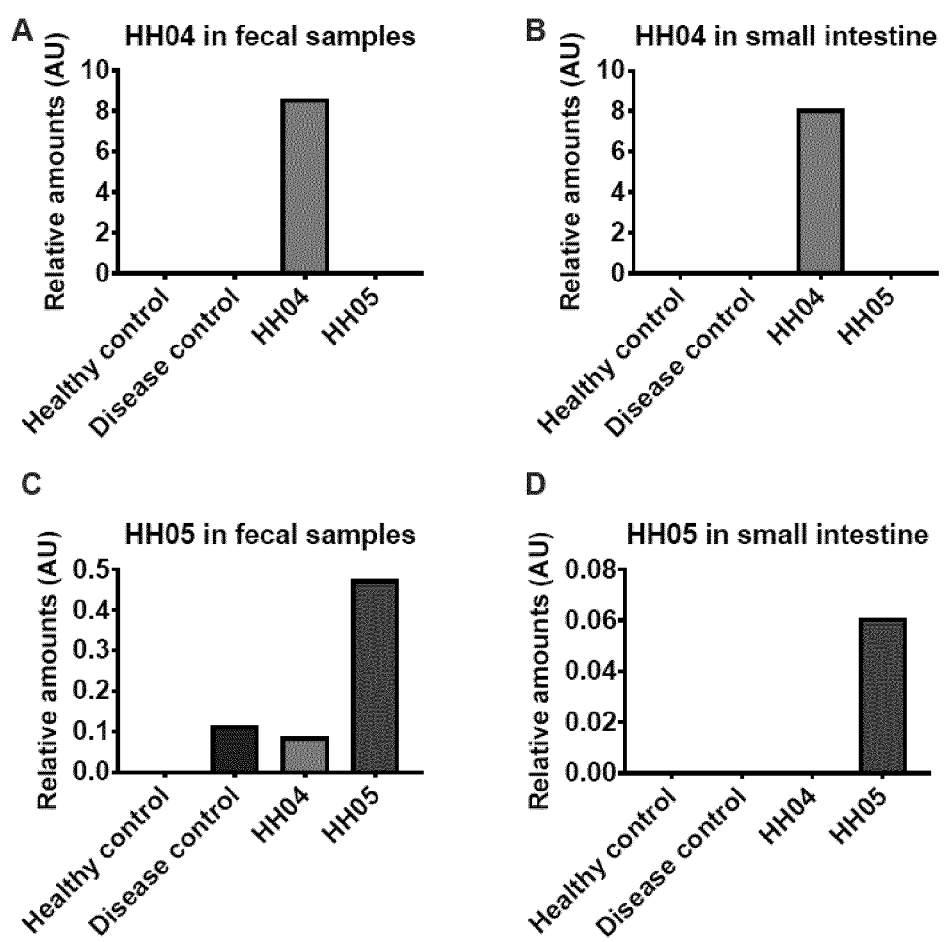
FIG. 30 shows results of *Lactobacillus* strain effect on gut microbiota composition in a diet-induced obesity mouse model. A) DNA from HH04 *Lactobacillus* strain strain found in fecal samples. B) DNA from HH04 probiotic strain found in small intestine content. C) DNA from HH05 *Lactobacillus* strain strain found in fecal samples. D) DNA from HH05 *Lactobacillus* strain strain found in small intestine content. E) Principal coordinate analysis (PCoA) using weighted unifrac distances clutering the fecal microbiota composition from the end of the study within the indicated groups. Larger points indicate group mean of 10-12 mice per group. F) Principal coordinate analysis (PCoA) using weighted unifrac distances clutering the small intestine microbiota composition from the end of the study within the indicated groups. Larger points indicate group mean of 10-12 mice per group. More details about the study can be found in example 10.
Figure 30:
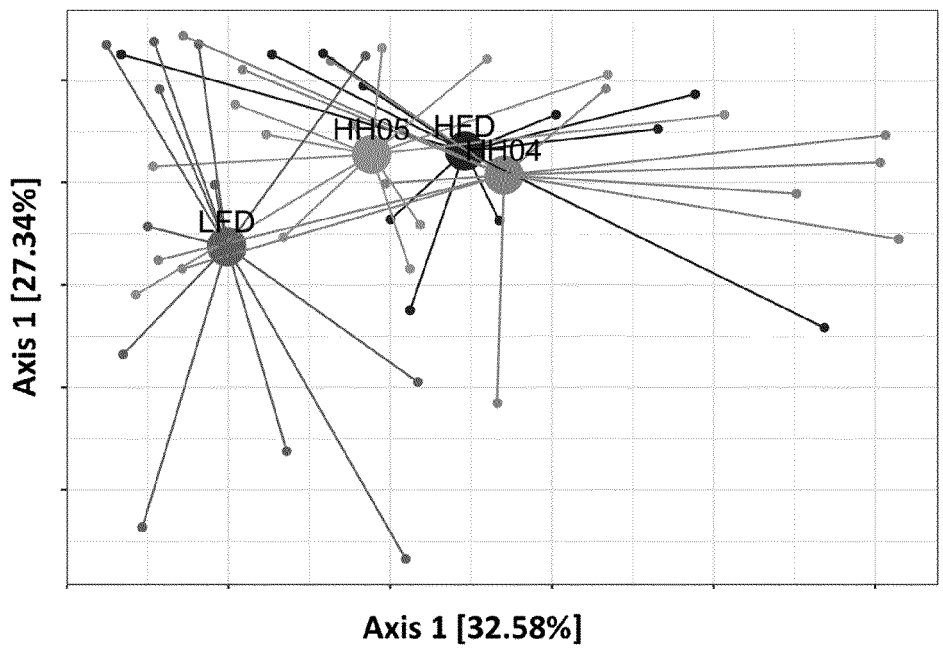
Figure 30:
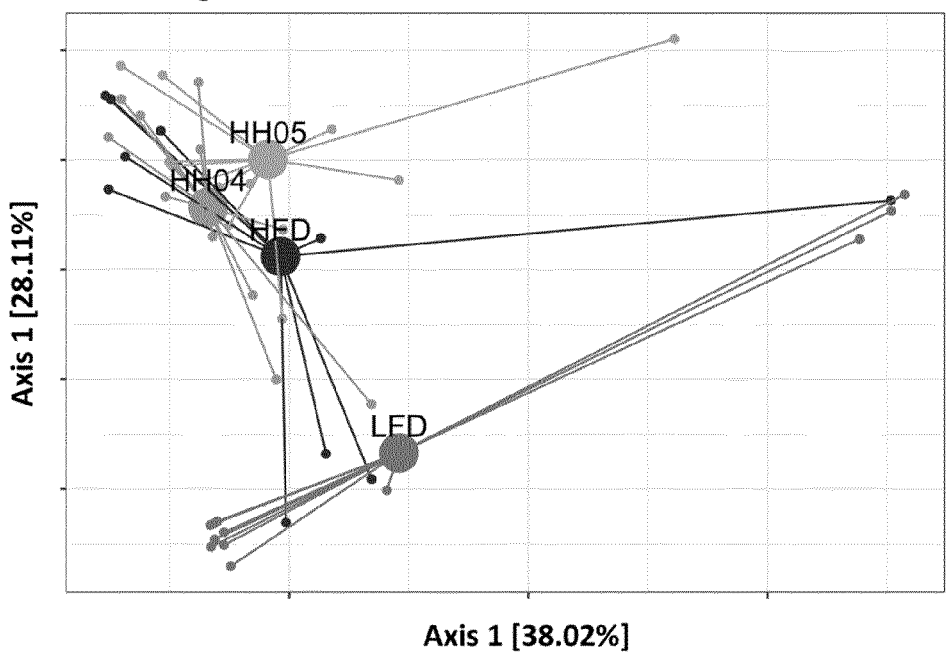

The effect of probiotics on gut microbiota composition is shown in FIG. 30 where E) is principal coordinate analysis (PCoA) of weighted UniFrac distances of fecal microbiota composition with large points indicating mean of each group and small points indicating individual samples. F) as E, but of microbiota composition of small intestine content.

Results—Weight Development

The body weight distribution was similar in all groups before the change from LFD acclimatization diet to HFD in week 0 in the HFD experimental groups. Daily oral gavage with HH04 in group C significantly reduced weight gain on a high fat diet compared to group B from week 6 and onwards. The group D gavaged with HH05 did now exhibit the same effects on body weight gain. Group A on low fat diet gained significantly less weight than the group B from week 2 throughout the study period.

There was no difference in fat mass in week 0 between the groups. Gavage with HH04 resulted in lower fat percentage on a high fat diet in group C in week 4, 8 and 12 compared to the group B. The results suggest the lower weight gain was caused by lower gain in fat mass. Group A similarly showed significantly lower fat percentage in week 4, 8 and 12 compared to the group B. The group D exhibited no difference in fat percentage compared to group B at any timepoints throughout the study period. The absolute amount of fat in grams was significantly lower in group A in week 4, 8 and 12 and in week 8 and 12 in the group C compared to the Group B. Group D had similar absolute fat mass as the group B at all measured timepoints.

The lean mass as percentage of total body weight was equal between the groups in week 0. The lean mass percentage was significantly increased in the groups C and A in week 4, 8 and 12 compared to the Group B. These results further support that the lower weight gain was specific to lower gain of fat mass. These results support the conclusion that HH04 has a significant impact on body composition and that daily administration of this strain can reduce the fat content.

Results—Effect of *Lactobacillus* Strains on Glucose Regulation and Gut Permeability.

The 5 h fasted blood glucose was significantly lower in the groups A and C compared to the control group B. Insulin levels after 5 h fasting were significantly lower in groups A and C compared to the group B. Group D showed no difference in fasting blood glucose or insulin levels compared to the group B.

Group A had lower blood glucose levels than the group B throughout the entire oral glucose tolerance test. Group C exhibited lower blood glucose levels than group B 30, 60 and 90 min after the glucose challenge, which suggests a better glucose tolerance. The areas under the curves from the oral glucose tolerance test similarly suggested an overall improved glucose tolerance in the groups A and C. Group D showed no improvement in blood glucose values during the oral glucose test nor lower areas under the curves.

Group C had lower glucose-stimulated insulin secretion the first 15 min after a glucose challenge compared to group B, suggesting improved insulin sensitivity after oral gavage of HH04. In contrast, group A shows no statistical difference in insulin levels compared to the group B after the oral glucose challenge. Group A secreted less insulin than group B upon the glucose challenge the first hour of the test while group D was no different than the group B throughout the test. The areas under the curves of the insulin levels during the oral glucose tolerance test showed a significant difference between the Group A and B with no difference to the remaining groups.

Results—Effect of *Lactobacillus* Strains on Tissue Weights

The liver weight was lower between the group B and the groups A and C, respectively.

The iWAT mass, a subcutaneous adipose depot, was lower in groups A and C compared with group B with no difference to the group D.

The mWAT mass, a visceral fat depot, was significantly lower in groups A and C compared with group B. No difference was observed between the groups B and D.

The weight of the brain and heart were not different between any of the groups independent of diet or *Lactobacillus* strain administration.

Results—Effect of *Lactobacillus* Strains on Plasma Lipids and Liver Health Biomarkers Alanine aminotransferase (ALT), a commonly used biomarker for liver damage, was lowered in group C treated with HH04 compared to the disease control group B.

Aspartate aminotransferase (AST), an alternative liver disease biomarker was less changed between the groups than ALT levels, but tended to be reduced by HH04 (group C) compared to the disease control group B.

Circulating triglyceride levels were not different between the groups.

Total circulating cholesterol levels were increased in the disease control compared to the healthy control (group B and C) and reduced by treatment of either HH04 or HH05 (group C and D).

Results—Effect of *Lactobacillus* Strains on Liver Lipid Accumulation

The accumulation of triglycerides and cholesterol in the liver tissue is an indicator of obesity and non-alcoholic fatty liver disease (NAFLD), as observed in the increased lipid levels found in group B compared to group A. Both triglycerides and cholesterol levels were lowered in group C compared to group B while group D had similar lipid accumulation.

Results—Effect of *Lactobacillus* Strains on Intestinal Inflammation

The classically pro-inflammatory cytokine interferon gamma (IFNγ) was increased in group B compared to group A. The level of IFNγ was reduced in group C compared to group B. The anti-inflammatory cytokine IL-10 was increased in group B compared to group A.

Results—Effect of *Lactobacillus* Strains on Gut Microbiota Composition

The HH04 DNA was only found in mice treated with this *Lactobacillus* strain and in similar amounts in fecal and small intestine samples. HH05 DNA was found in small amounts in fecal samples of vehicle control and HH04 treated mice but was far more abundant on the mice treated with HH05. In small intestine content HH05 was only found in mice treated with this *Lactobacillus* strain. The overall fecal microbiota composition was largely affected by the diet. The fecal microbiota composition of HH05 treated mice clustered in between vehicle treated HFD fed and LFD fed mice, where HH04 treated mice had fecal microbiota resembling that of the control. The microbiota composition of the small intestine was also largely affected by the diet, and both HH04 and HH05 treated mice clustered apart from the control and thus had a different microbial composition. Indicating that the *Lactobacillus* strain treatment moderately modulates the gut microbiota composition.

Conclusion

On a classical high fat diet the *Lactobacillus* strain HH04 reduced gain in body weight and fat mass while increasing the percentage of lean mass. In addition, HH04 decreased 5 h fasting glucose and insulin levels and increased glucose tolerance and insulin sensitivity compared to the high fat control. *Lactobacillus* strain HH04 also lowered the mass of the subcutaneous fat depot iWAT and visceral fat depot mWAT and liver lipid accumulation and shifted intestinal inflammation towards more anti-inflammatory profile.

HH05 reduces cholesterol levels in circulation and changes the gut microbiota in combination with a classical high fat diet.

Figure 21:
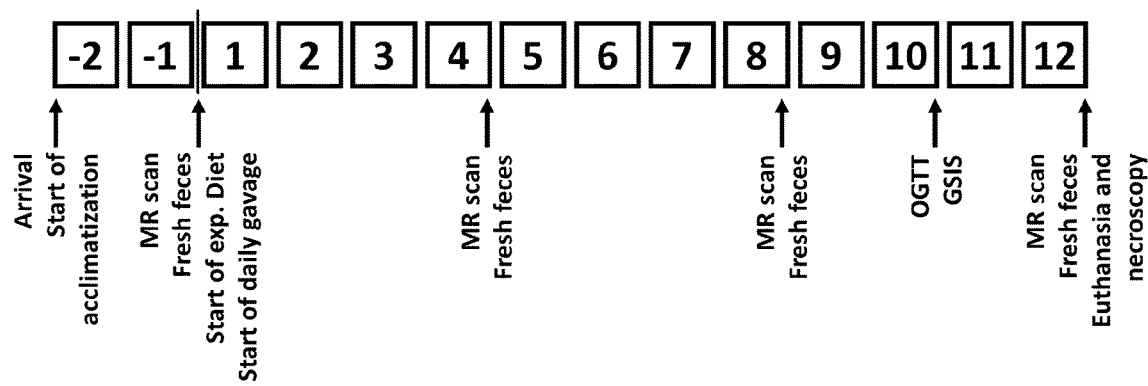
FIG. 21 shows the study overview of the mouse study described in example 10.

Example 11. Impact of *Lactobacillus* Strain Strains in a Diet-Induced Mouse Model Fed a Modified High Fat Diet The study aimed to demonstrate improved metabolic health, such as prediabetes, by three *Lactobacillus* strain test stains (HH02, HH04 and HH05) in a diet-induced obesity (DIO) mouse model using a modified Western diet designed to induce inflammation resembling human obese phenotype. The study was identical to the study shown in Example 10 except for the diet and addition of the *Lactobacillus* strain strain HH02. The study overview are shown in FIG. 21.

Study Overview:

The study was designed and carried out as described in Example 10 except for the following addition of group E and change of diet to induce an obesity phenotype featuring enhanced inflammation:

| Group number | Number of mice | Diet | Daily oral gavage |
| --- | --- | --- | --- |
| A | 12 | LFD | Vehicle (PBS, Gibco) |
| B | 9 | Mod. HFD | Vehicle (PBS, Gibco) |
| C | 12 | Mod. HFD | HH04-$10^8$ CFU |
| D | 12 | Mod. HFD | HH05-$10^8$ CFU |
| E | 12 | Mod. HFD | HH02-$10^8$ CFU |

Modified Western diet (HFD) containing 43% of the energy from fat (butterfat), 42% from carbohydrates (mainly sucrose and fructose), 15% of protein (mixed sources) (D12079 mod*, Ssniff Spezialdiaten, Germany)

Low fat reference diet (Ssniff Spezialdiaten, Germany) matched to the modified WD containing 14% of energy from fat.

Figure 31:
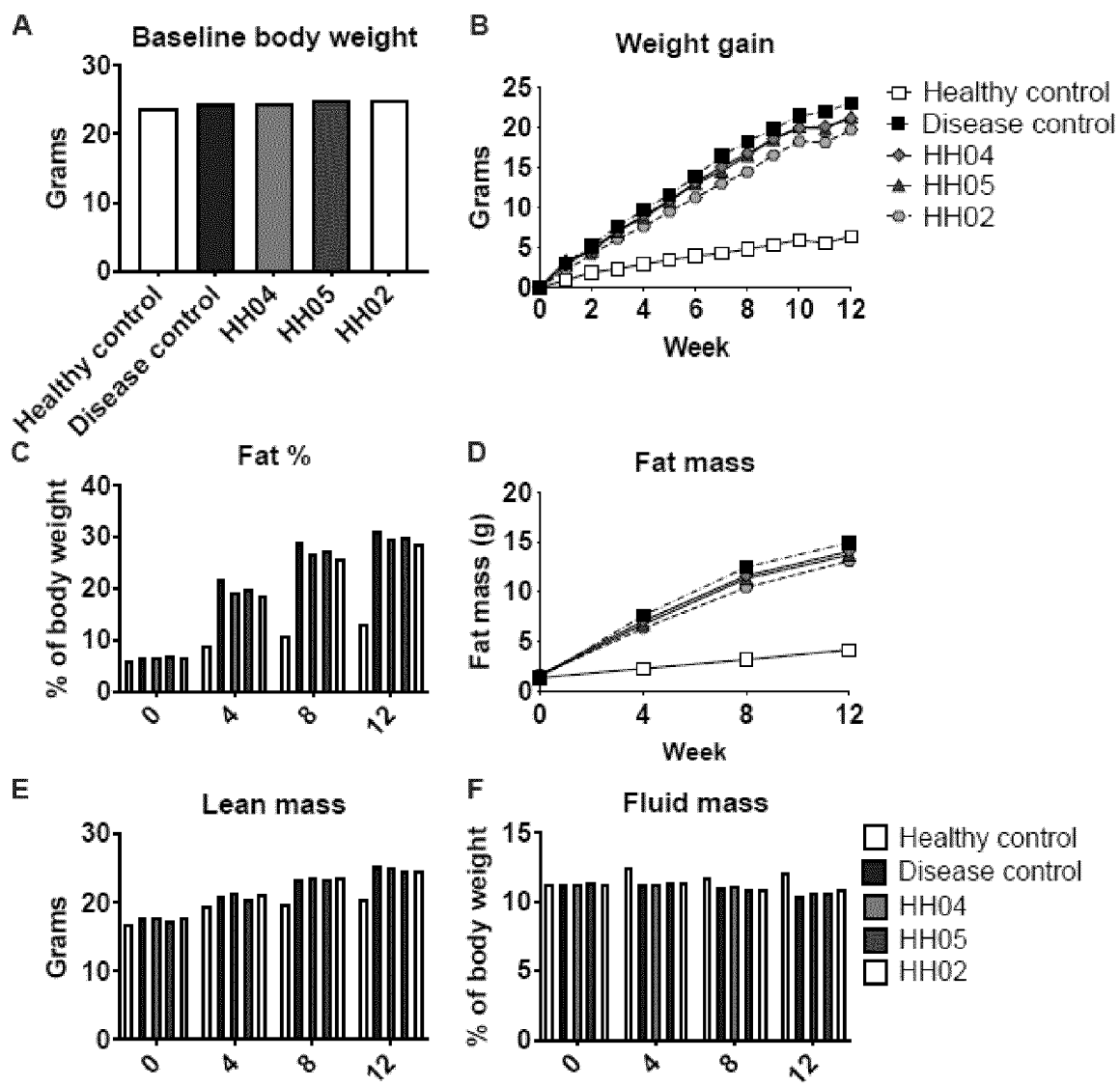
FIG. 31 shows the effect of HH04, HH05, and HH02 on weight development and body composition in a diet-induced obesity mouse (DIO) model. Mean of 10-12 mice per group are shown A) Weight after randomization. B) Weight development in individual groups post initiation of experimental diets and gavage treatment. C) Fat mass as % of total body weight obtained from Magnetic Resonance scans at the depicted time points. D) Fat mass development as grams depicted as group mean with connecting lines. E) Lean mass as gram obtained from Magnetic Resonance scans at the depicted time points. F) Fluid mass as % of body weight obtained from Magnetic Resonance scans at the depicted time points. More details can be found in example 11.

Sampling and Measurements:

Weight development and body composition is shown in FIG. 31. Mean of 9-12 mice per group are shown A) Body weight after randomization prior to the start of experimental diets and treatments. B) Weight development in individual groups post initiation of experimental diets and gavage treatment. C) Fat mass as % of total body weight obtained from Magnetic Resonance scans at the depicted time points. D) Fat mass in grams depicted as group mean with connecting lines. E) Lean mass in grams obtained from Magnetic Resonance scans at the depicted time points. F) Fluid mass as % of total body weight obtained from Magnetic Resonance scans at the depicted time points.

Glucose Tolerance Test and Glucose-Stimulated Insulin Secretion

An oral glucose tolerance test was performed in week 10 of the experimental protocol. Mice were fasted at 8 AM for 5 h and gavaged at 11 AM. 5 h fasted blood glucose measurement (OneTouch Vario Flex, LifeScan) and sampling of the blood from the tail vein were executed prior to oral gavage with 1.5 µg dextrose pr. g lean mass. Blood glucose was measured from tail vein puncture at time points 0, 15, 30, 60, 90, and 120 min after dextrose challenge and blood samples for insulin and c-peptide were taken in EDTA prepared capillary tubes (Sarstedt) at time points 0, 15, 30, 60, and 120 min post challenge. Mice received 0.5 mL saline (Hospira) after the procedure allowing the mice to rehydrate.

Figure 32:
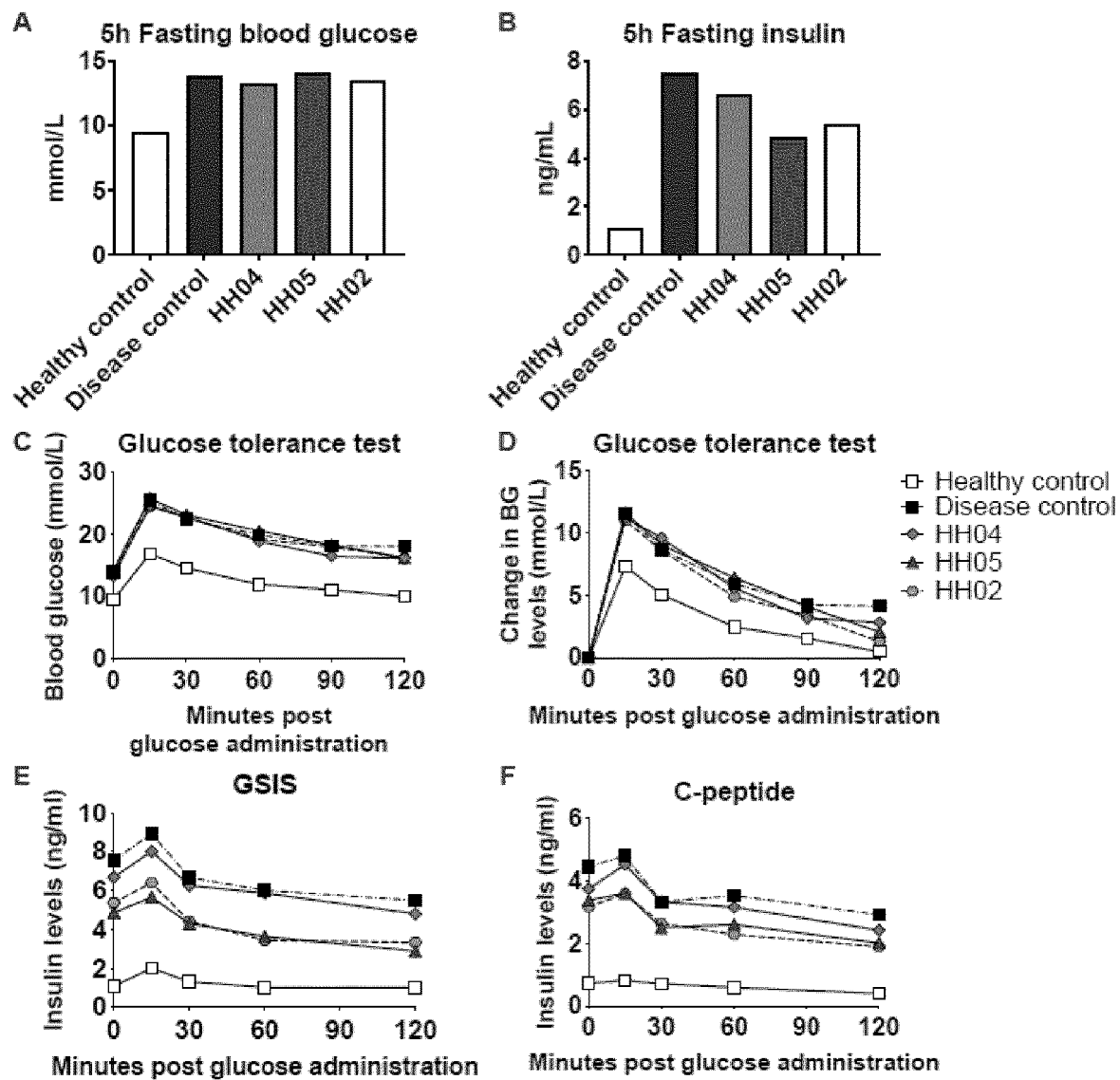
FIG. 32 shows the effect of *Lactobacillus* strains of HH04, HH05, and HH02 on glucose regulation. A) 5 h fasted blood glucose after 10 weeks of modified WD feeding and daily gavage treatments. Bars mean of 10-12 mice per group. B) 5 h fasting insulin levels after 10 weeks of mod. WD feeding and daily gavage treatments. C) Oral Glucose tolerance test in 5 h fasted mice after 10 weeks of mod. WD feeding and daily gavage treatments during the challenge (1.5 μg dextrose per g lean mass). D) As C, but showing change in blood glucose values from fasting values during the challenge. E) Plasma levels of the endogenous insulin response to the glucose challenge. F) C-peptide levels in plasma during the challenge A-F) Data represents mean of 10-12 mice per group. More details about the study can be found in example 11.

The effect of *Lactobacillus* strains on glucose regulation and gut permeability is shown in FIG. 32: A) 5 h fasted Blood Glucose after 10 weeks of WD feeding and daily gavage treatments. Bars show mean of 9-12 mice per group. B) 5 h fasted insulin level after 10 weeks of WD feeding and daily gavage treatments. Bars mean of 9-12 mice per group. C) Oral Glucose tolerance after 10 weeks of WD feeding and daily gavage treatments showing absolute blood glucose values. D) As C but depicting change in blood glucose from baseline during the challenge. E) Plasma levels of the endogenous insulin response to the glucose tolerance test. F) C-peptide levels during the glucose tolerance test.

Necroscopy and Tissue Harvesting

Necropsy was carried out after 12 weeks of the experimental protocol. Mice were fasted from 8 AM and gavaged at 11 AM. Euthanasia was done in alternating order taking one mouse Cardiac puncture was done using a 25 G needle and 1 mL syringe coated with EDTA (Sigma-Aldrich. The or weights were measured and the tissues immediately frozen in liquid nitrogen and stored at −80° C. Tissues were dissected by the same operator and taken in the same order for all mice.

Figure 33:
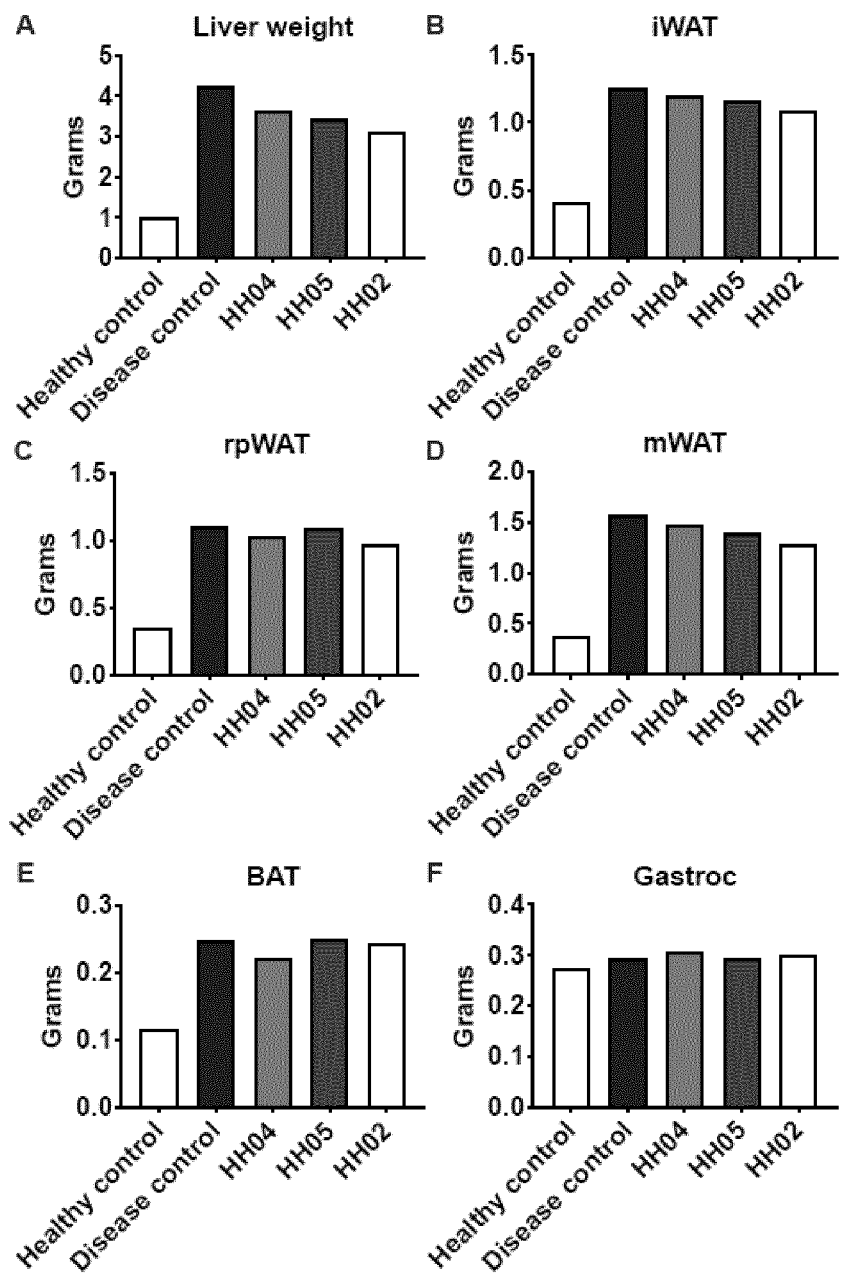
FIG. 33 shows the effect of *Lactobacillus* strains of HH04, HH05, and HH02 on tissue weights in a diet-induced obesity mouse model. Bars represent mean value of 10-12 mice per group A) Weight of the liver at necropsy after 12 weeks of daily gavage. B) Weight of the inguinal white adipose tissue (iWAT) at necropsy after 12 weeks of daily gavage. C) Weight of the retroperitoneal white adipose tissue (rpWAT) at necropsy after 12 weeks of daily gavage. D) Weight of the mesenchymal white adipose tissue (mWAT) at necropsy after 12 weeks of daily gavage. E) Weight of the intreascapular brown adipose tissue (BAT) at necropsy after 12 weeks of daily gavage. F) Weight of the gastrocnemius muscles at necropsy after 12 weeks of daily gavage. More details about the study can be found in example 11.

The effect of *Lactobacillus* strains on tissue weights are shows in FIG. 33, wherein bars represent mean value of 9-12 mice per group A) Liver weight in grams B) inguinal white adipose tissue (iWAT) weight, C) retroperitoneal white adipose tissue (rpWAT) weight, D) mesenchymal adipose white tissue (mWAT) weight, E) intrascapular brown adipose tissue (BAT) weight, and F) gastrocnemius muscle (Gastroc) weight.

Plasma Biochemical Analysis

Figure 34:
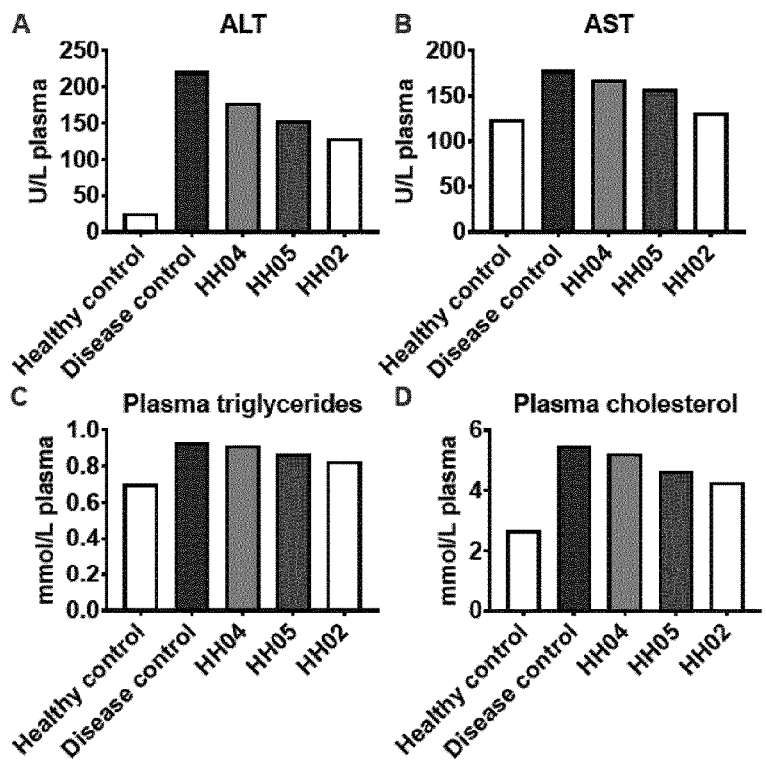
FIG. 34 shows results of *Lactobacillus* strain effect on plasma markers in a diet-induced obesity mouse model. A) Alanine aminotransferase. B) Aspartate aminotransferase. C) Triglycerides. D) Total cholesterol. A-D) Each bar represents mean of 10-12 mice per group. More details about the study can be found in example 11.

The effect of *Lactobacillus* strains on plasma biomarkers of liver damage and lipid levels are shown in FIG. 34 wherein bars represent mean value of 9-12 mice pr. group. These analyses were carried out by the medical biochemistry department at Université Laval, Heart and Lung Institute under locally developed procedures meeting the highest criteria for handling and analysis of human and animal samples. A) Alanine aminotransferase (ALT) biomarker of liver damage, B) Aspartate aminotransferase (AST) biomarker of liver damage, C) Plasma triglyceride levels, D) Plasma total cholesterol levels.

Figure 35:
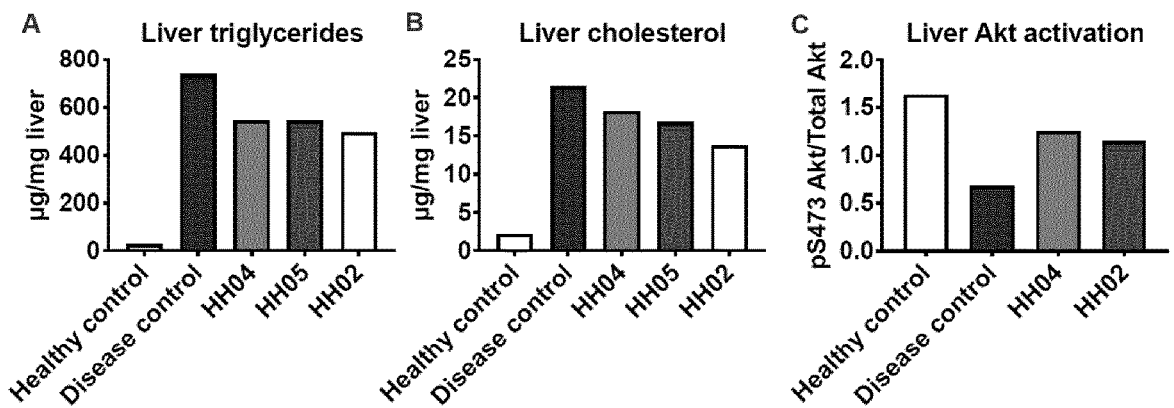
FIG. 35 shows results of *Lactobacillus* strain effect on liver lipid accumulation in a diet-induced obesity mouse model. A) Triglyceride content in liver tissue as μg per mg liver and B) Cholesterol in liver tissue as μg per mg liver. C)

Liver Lipid Accumulation and Activation of Insulin Signaling Pathway in Liver Tissue The liver of each mouse was homogenized in liquid nitrogen by cryo-grinding the tissue with mortar and pestle while kept frozen and transferred to new tubes. Lipids were extracted from 50 mg of the powdered tissue. The effect of *Lactobacillus* strains on hepatic lipid accumulation were measured by calorimetric assays and are shown in FIG. 35 wherein bars represent mean value of 9-12 mice per group. A) Total triglyceride amount in the liver tissue, and B) Total cholesterol content in the liver tissue.

The protein levels of phosphorylated (activated) and total Akt in the liver tissue of 3-4 insulin-stimulated mice per group (Group A,B,C,E) was quantified by Western Blot using pS473 Akt and pan Akt antibodies (Cell Signaling) and quantified using BioRad software. The effect of *Lactobacillus* strains on the sensitivity of insulin-stimulation in activation of the Akt pathway is shown in FIG. 35C) Ratio of activated (pS473 Akt) to total Akt protein levels in liver tissue expressed in arbitrary units.

Tissue Cytokine Quantification

Cytokine levels were measured in homogenized liver and colon tissue using the Bio-Plex 200 Luminex system following the manufacturer's instructions. The levels are shown in FIG. 36 bars represent mean value of 9-12 mice per group. A) Tumor necrosis factor alpha (TNFα) levels in liver tissue, B) Interferon gramma (IFNγ) levels in liver tissue, C) Tumor necrosis factor alpha (TNFα) levels in colon tissue, D) Interferon gramma (IFNγ) levels in colon tissue.

Gut Microbiota Analysis

Bacterial DNA was extracted from the frozen fecal samples and the hypervariable V3-V4 16S rRNA region was amplified and sequenced using the Illumina MiSeq platform.

The sequence data was pre-processed, tag identified and trimmed, paired-end reads were merged, truncated at a quality score of 4, and requiring at least 100 bp overlap with a merged read length between 300 and 600 bp in length. Sequences were strictly dereplicated, discarding clusters with less than 5 sequences. Sequences were clustered at 97% sequence similarity, using the most abundant strictly dereplicated reads as centroids and discarding suspected chimeras based on internal comparison. Taxonomic assignment of OTUs is done using the database from Ribosomal Database Project.

The effect of *Lactobacillus* strains on gut microbiota composition is shown in FIG. 37 showing principal coordinate analysis (PCoA) of weighted UniFrac distances of fecal microbiota composition with large points indicating mean of each group and small points indicating individual samples.

Results—Effect of *Lactobacillus* Strains on Weight Development

The body weights of the groups were similar at the start of the study prior to the initiation of the daily treatment by oral gavage and experimental diets. The groups treated with HH04 or HH05 gained slightly less weight during the study period when fed a modified WD where the group treated with HH02 gained less weight during the study.

The fat % was similar in all groups at the beginning of the study period and feeding of modified WD increased the fat %. The groups treated with either HH04, HH05, or HH02 had slightly lower fat % during week 4, 8, and 12 of the study while the lean and fluid mass was unchanged from the control group.

Results—Effect of *Lactobacillus* Strains on Glucose Regulation

The blood glucose levels after 5 hours of fasting was increased when mice were fed a modified WD for 10 weeks with no effect of the *Lactobacillus* strain treatments. The corresponding 5 h fasting insulin levels were however slightly decreased in mice treated with HH04 and markedly decreased in mice treated with HH05 or HH02 indicating an improved glucose homeostasis by these treatments.

During an oral glucose challenge there were small improvements in the groups treated with the *Lactobacillus* strains, most pronounced in the group treated with HH02. The corresponding glucose-stimulated insulin secretion (GSIS) was strongly reduced, pointing towards improved insulin sensitivity, in mice treated with HH02 or HH05 and with a minor reduction in the HH04 treated group. C-peptide levels further supported the reduced insulin production during a glucose challenge, especially by strains HH02 and HH05 with some effects from strain HH04.

Results—Effect of *Lactobacillus* Strains on Tissue Weights

The liver weight was highly increased by the feeding of a modified WD, which was reduced by the *Lactobacillus* strain treatments of either HH02, HH04 or HH05. Various white adipose tissues were tending to be decreased by the *Lactobacillus* strain treatments, most pronounced in the HH02 treated mice. The brown adipose tissue tended to be reduced in the group treated with HH04 while there was no difference in muscle mass by any of the *Lactobacillus* strain treatments.

Results—Effect of *Lactobacillus* Strains on Plasma Lipids and Liver Health Biomarkers The marker of liver damage ALT was highly increased by feeding of a modified WD. This was improved by the treatment of *Lactobacillus* strains, most pronounced by HH02 treatment. Similar observations were made on another marker of liver damage, AST. Levels of circulating triglycerides and cholesterol were reduced in mice treated with HH05 or HH02, respectively. The accumulation of triglycerides and cholesterol in the liver tissue observed in modified WD fed mice was reduced by treatment of either HH02, HH04 or HH05. Activation of the Akt pathway observed by increased ratio of phosphorylated Akt to total Akt protein levels was decreased in mice fed a modified WD in the liver tissue. This indication of insulin resistance in the liver was counteracted by HH04 or HH02 treatment, as observed by an increased Akt activation.

Results—Effect of *Lactobacillus* Strains on Inflammation in Liver and Intestinal Tissue Mice fed a modified WD had increased levels of pro-inflammatory cytokines TNFα and IFNγ in liver tissue with no effect of *Lactobacillus* strain treatment. In colonic tissue mice treated with HH05 or HH02 had reduced cytokine levels.

Results—Effect of *Lactobacillus* Strains on Gut Microbiota Composition

The overall fecal microbiota composition was largely affected by the diet. The fecal microbiota composition of HH02, HH04, or HH05 treated mice clustered apart from the control, although this effect was smaller than the distance from the LFD to the WD control groups. This indicates, that the *Lactobacillus* strain treatments induce moderate effects on the gut microbiota composition.

Conclusion

The study indicates that the diet affects the efficacy of *Lactobacillus* strains. In the current study where mice were fed an inflammation-promoting modified WD mice treated with HH04 showed small effects on body weight and liver weight reduction yet, HH04-treated mice secreted less insulin during a glucose tolerance test, indicating improved insulin sensitivity. This was further supported by reduced liver damage markers measured in plasma, reduced liver lipid and cholesterol accumulation and an augmented insulin signaling in the liver tissue.

Treatment with HH05 greatly reduced fasting and glucose-stimulated insulin pointing towards an improved insulin sensitivity. In addition, liver weight, liver damage markers, triglyceride and cholesterol levels of the liver were reduced by HH05 treatment. Circulating cholesterol levels were also reduced by HH05 treatment concomitant with reductions of colonic inflammation.

HH02-treated mice showed reduced body weight gain during the study. During a glucose tolerance test, mice treated with HH02 returned to their baseline blood glucose faster than the control group and greatly reduced fasting and glucose stimulated insulin levels pointing towards a large improvement of insulin sensitivity. The HH02 treatment decreased liver and mesenchymal adipose tissue weight in addition to lower levels of circulating cholesterol and triglycerides. Markers of liver damage were also greatly reduced and associated with increased insulin sensitivity in the liver tissue. In colon tissue, pro-inflammatory cytokine levels were reduced.

Example 12. Reproducibility of Probiotic Effects in Two Different Diet-Induced Mouse Models The study aimed to demonstrate reproducibility of improved metabolic health, such as prediabetes, by three probiotic test stains (HH02, HH04 and HH05) in two different diet-induced obesity (DIO) mouse models using a classical HFD and a modified Western diet. The study was identical to the studies shown in Example 10 and Example 11 aiming to reproduce observed findings. In addition, performance of HH02 in the classical HFD model were tested for the first time. The study overview is shown in FIG. 21.

Study Overview:

The study was designed and carried out as described in Example 10 and 11 including the same probiotic treatments in mice fed either of the two high fat diets simultaneously:

| Group number | Number of mice | Diet | Daily oral gavage |
| --- | --- | --- | --- |
| A | 9 | LFD | Vehicle (PBS, Gibco) |
| B | 9 | HFD | Vehicle (PBS, Gibco) |
| C | 9 | HFD | HH04-$10^8$ CFU |
| D | 9 | HFD | HH05-$10^8$ CFU |
| E | 9 | HFD | HH02-$10^8$ CFU |
| F | 9 | Mod. WD | Vehicle (PBS, Gibco) |
| G | 9 | Mod. WD | HH04-$10^8$ CFU |
| H | 9 | Mod. WD | HH05-$10^8$ CFU |
| I | 9 | Mod. WD | HH02-$10^8$ CFU |

High fat/sucrose diet (HFD) containing 45% of the energy from fat (87% lard, 13% soy bean oil), 35% from carbohydrates (mainly sucrose and maltodextrin), 20% of protein (casein) (D12451, Ssniff Spezialdiaten, Germany)

Modified Western diet (Mod. WD) containing 43% of the energy from fat (butterfat), 42% from carbohydrates (mainly sucrose and fructose), 15% of protein (mixed sources) (D12079 mod*, Ssniff Spezialdiaten, Germany)

Low fat reference diet (Ssniff Spezialdiaten, Germany) matched to the mod. WD containing 14% of energy from fat.

Sampling and Measurements:

Weight development and body composition is shown in FIG. 38. Mean of 8-9 mice per group are shown A) Body weight after randomization prior to the start of experimental diets and treatments for groups fed LF or HFD diet during the study (A-E). B) Body weight after randomization prior to the start of experimental diets and treatments for groups fed LF or Mod. WD diet during the study (A, F-I). C) Weight development in individual groups fed LFD or HFD (A-E) post initiation of experimental diets and gavage treatment. D) Weight development in individual groups fed LFD or Mod. WD (A, F-I) post initiation of experimental diets and gavage treatment. E) Fat mass as % of total body weight obtained from Magnetic Resonance scans at the depicted time points for groups fed LFD or HFD (A-E). F) Fat mass as % of total body weight obtained from Magnetic Resonance scans at the depicted time points for groups fed LFD or Mod. WD (A, F-I). G) Fat mass in grams depicted as group mean with connecting lines for groups fed LFD or HFD (A-E). H) Fat mass in grams depicted as group mean with connecting lines for groups fed LFD or Mod. WD (A, F-I). I) Lean mass in grams obtained from Magnetic Resonance scans at the depicted time points in groups fed LFD or HFD (A-E). J) Lean mass in grams obtained from Magnetic Resonance scans at the depicted time points in groups fed LFD or Mod. WD (A, F-I).

Glucose Tolerance Test and Glucose-Stimulated Insulin Secretion

An oral glucose tolerance test was performed in week 10 of the experimental protocol. Mice were fasted at 8 AM for 5 h and gavaged at 11 AM. 5 h fasted blood glucose measurement (OneTouch Vario Flex, LifeScan) and sampling of the blood from the tail vein were executed prior to oral gavage with 1.5 µg dextrose pr. g lean mass. Blood glucose was measured from tail vein puncture at time points 0, 15, 30, 60, 90, and 120 min after dextrose challenge and blood samples for insulin and c-peptide were taken in EDTA prepared capillary tubes (Sarstedt) at time points 0, 15, 30, 60, and 120 min post challenge. Mice received 0.5 mL saline (Hospira) after the procedure allowing the mice to rehydrate.

The effect of probiotics on glucose regulation and gut permeability is shown in FIG. 39: A) 5 h fasted Blood Glucose after 10 weeks of HFD feeding and daily gavage treatments. Bars show mean of 9-12 mice per group fed LFD or HFD (A-E). B) 5 h fasted Blood Glucose after 10 weeks of HFD feeding and daily gavage treatments. Bars show mean of 9-12 mice per group fed LFD or Mod. WD (A, F-I). C) 5 h fasted insulin level after 10 weeks of HFD feeding and daily gavage treatments. Bars mean of 9-12 mice per group fed LFD or HFD (A-E). D) 5 h fasted insulin level after 10 weeks of HFD feeding and daily gavage treatments. Bars mean of 9-12 mice per group fed LFD or Mod. WD (A, F-I). E) Oral Glucose tolerance after 10 weeks of HFD feeding and daily gavage treatments showing change in blood glucose from baseline during the challenge in groups fed LFD or HFD (A-E). F) Oral Glucose tolerance after 10 weeks of HFD feeding and daily gavage treatments showing change in blood glucose from baseline during the challenge in groups fed LFD or Mod. WD (A, F-I). G) Plasma levels of the endogenous insulin response to the glucose tolerance test in groups fed LFD or HFD (A-E). H) Plasma levels of the endogenous insulin response to the glucose tolerance test in groups fed LFD or Mod. WD (A, F-I). I) C-peptide levels during the first 30 min of the glucose tolerance test in groups fed LFD or HFD (A-E). J) C-peptide levels during the first 30 min of the glucose tolerance test in groups fed LFD or Mod. WD (A, F-I).

Results—Effect of Probiotics on Weight Development

The body weight of the groups was similar at the start of the study prior to the initiation of the daily treatment by oral gavage and experimental diets. The groups fed HFD (as Example 10) and treated with HH04 gained less weight during the study. The groups fed Mod. WD did not reduce weight gain regardless of probiotic treatment. As observed in Example 10, the group fed HFD and treated HH04 reduced fat mass gain. No probiotic treatment reduced fat mass increase when the mice were fed a Mod. WD. The lean mass gain was unaffected by probiotic treatments irrespective of the diet.

Results—Effect of Probiotics on Glucose Regulation

The blood glucose levels after 5 hours of fasting was increased in mice fed either HFD or Mod. WD, and this was unaffected by probiotic treatment. Insulin levels after 5 hours of fasting was increased when mice were fed an HFD and reduced in mice that were additionally treated with HH04. Mice fed mod. WD already exhibited increased fasting insulin levels. Mice treated additionally with HH05 significantly reduced the fasting insulin levels, where mice treated with HH02 had a great lowering of the fasting insulin values.

During an oral glucose tolerance test after 10 weeks of feeding HFD, the mice treated with HH04 had lowered blood glucose values during the test similar to the findings in Example 10, which shows improved glucose tolerance. Mice fed mod. WD had a performed worse in the glucose tolerance test, but this was reduced by treatment of either HH05 or HH02. The glucose-stimulated insulin secretion, as observed by both the insulin and c-peptide levels during the test were reduced in the mice fed HH04 when fed HFD compared to its control group. When fed a mod. WD mice treated with HH02 reduced both insulin and c-peptide levels indicating a markedly improved insulin sensitivity in these mice. Mice fed mod. WD and treated with HH05 exhibited reduced c-peptide levels compared to the control.

Conclusion:

The beneficial effects of the different probiotic strains are dependent on the diet of which the mice are fed. The effects of each probiotic strain on body weight and glucose regulation on the two experimental diets observed in Example 10 and Example 11 were overall reproduced in the current study. In summary, strain HH04 showed body weight and fat mass reducing effects on a normal HFD, which translate into improved glucose regulation. Strain HH05 shows beneficial effects of different glucose tolerance test readouts when the mice are fed the inflammation-promoting mod. WD. The HH02 strain shows an immense lowering of insulin resistance and thereby improving glucose regulation when mice are fed an inflammation-promoting modified WD.

Deposit of Biological Material

The following biological material has been deposited under the terms of the Budapest Treaty with the Leibniz-Institut DSMZ-Deutsche Sammlung von Mikroorganismen and Zellkulturen GmbH, Inhoffenstrasse 7B, D-38124 Braunschweig, Germany and given the following accession number:

*Lactobacillus reuteri* (HH01); Accession Number: DSM 17648; Date of Deposit: Dec. 10, 2005; Origin of Country: Germany.

*Lactobacillus reuteri* (HH02); Accession Number: DSM 32910; Date of Deposit: Apr. 9, 2018; Origin of Country: Germany.

*Lactobacillus rhamnosus* (HH03); Accession number: DSM 32911; Date of Deposit: Apr. 9, 2018; Origin of Country: Germany.

*Lactobacillus paracasei* ssp. *tolerans* (HH04); Accession number: DSM 32851; Date of Deposit Apr. 7, 2018; Origin of Country: Germany.

*Lactobacillus paracasei* ssp. *paracasei* (HH05); Accession number: DSM 32853; Date of deposit: Apr. 7, 2018; Origin of Country: Germany.

The strains have been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention claimed is:

1. A *Lactobacillus* strain selected from DSM 32910, DSM 32911, DSM 32851 and DSM 32853, wherein the strain is in freeze-dried from or spray-dried form.

2. The *Lactobacillus* strain according to claim 1, wherein the strain has the ability of improving or alleviating one or more prediabetes symptoms selected from insulin resistance, high-blood glucose, low-grade inflammation and gut barrier function.

3. The *Lactobacillus* strain according to claim 1, wherein the strain survives in the gastrointestinal (GI) tract.

4. The *Lactobacillus* strain according to claim 1, wherein the strain is DSM 32851.

5. A composition comprising a *Lactobacillus* strain according to claim 1.

6. The composition according to claim 5, wherein the composition comprises $10^6$-$10^{14}$ colony forming units (CFU) of total *Lactobacillus* strain per gram of the composition.

7. A dietary supplement comprising a *Lactobacillus* strain according to claim 1.

8. A method of improving the metabolic health of an individual, the method comprising administering to the individual in need of improving the metabolic health a *Lactobacillus* strain according to claim 1.

9. The method of claim 8, wherein improving the metabolic health is selected from alleviating prediabetes, preventing or alleviating type 2 diabetes, alleviating insulin resistance, improving liver health, reducing gut inflammation, improving gut barrier function, lowering blood glucose level, and preventing or reducing weight gain from a high fat diet.

10. The method of claim 8 wherein the individual is a human.

11. The composition according to claim 5, wherein the composition comprises $10^7$-$10^{13}$ colony forming units (CFU) of total *Lactobacillus* strain per gram of the composition.

12. The composition according to claim 5, wherein the composition comprises $10^8$-$10^{12}$ colony forming units (CFU) of total *Lactobacillus* strain per gram of the composition.

13. The composition according to claim 5, wherein the composition comprises the *Lactobacillus* strain deposited as DSM 32851 and one or more *Lactobacillus* strains selected from the strains deposited as DSM 17648, DSM 32910, DSM 32911 and DSM 32853.

14. The composition according to claim 5, wherein the composition comprises the Lactobacillus strain deposited as DSM 32910 and one or more *Lactobacillus* strains selected from the strains deposited as DSM 17648, DSM 32911, DSM 32851 and DSM 32853.

15. The *Lactobacillus* strain according to claim 1, wherein the strain is in freeze-dried form.

16. The *Lactobacillus* strain according to claim 1, wherein the strain is in spray-dried form.

17. The *Lactobacillus* strain according to claim 1, wherein the strain is DSM 32910.

18. The *Lactobacillus* strain according to claim 1, wherein the strain is DSM 32911.

19. The *Lactobacillus* strain according to claim 1, wherein the strain is DSM 32853.

* * * * *